(12) United States Patent
Miyata

(10) Patent No.: US 9,293,714 B2
(45) Date of Patent: Mar. 22, 2016

(54) MATERIAL FOR ORGANIC ELECTROLUMINESCENCE DEVICE AND ORGANIC ELECTROLUMINESCENCE DEVICE USING THE SAME

(71) Applicant: SAMSUNG DISPLAY CO., LTD., Yongin, Gyeonggi-Do (KR)

(72) Inventor: Yasuo Miyata, Yokohama (JP)

(73) Assignee: SAMSUNG DISPLAY CO., LTD., Yongin, Gyeonggi-do (KR)

( * ) Notice: Subject to any disclaimer, the term of this patent is extended or adjusted under 35 U.S.C. 154(b) by 0 days.

(21) Appl. No.: 14/569,312

(22) Filed: Dec. 12, 2014

(65) Prior Publication Data

US 2015/0179950 A1    Jun. 25, 2015

(30) Foreign Application Priority Data

Dec. 20, 2013   (JP) .................................. 2013-264115

(51) Int. Cl.
| | | |
|---|---|---|
| *C07F 7/08* | (2006.01) | |
| *C07D 487/06* | (2006.01) | |
| *H01L 51/00* | (2006.01) | |
| *H01L 51/50* | (2006.01) | |

(52) U.S. Cl.
CPC .......... *H01L 51/0061* (2013.01); *C07D 487/06* (2013.01); *C07F 7/0812* (2013.01); *H01L 51/0072* (2013.01); *H01L 51/0073* (2013.01); *H01L 51/0074* (2013.01); *H01L 51/0094* (2013.01); *H01L 51/006* (2013.01); *H01L 51/0052* (2013.01); *H01L 51/0054* (2013.01); *H01L 51/0081* (2013.01); *H01L 51/5056* (2013.01); *H01L 2251/308* (2013.01)

(58) Field of Classification Search
CPC ............................ C07D 487/06; C07F 7/0812
See application file for complete search history.

(56) References Cited

U.S. PATENT DOCUMENTS

| 8,188,315 B2 | 5/2012 | Hwang et al. |
| 8,628,864 B2 | 1/2014 | Abe et al. |

FOREIGN PATENT DOCUMENTS

| EP | 2 284 920 A1 | 2/2011 |
| JP | 2013-033804 A | 2/2013 |
| WO | WO 2010/110553 A2 | 9/2010 |
| WO | WO 2012/091471 A2 | 7/2012 |

*Primary Examiner* — Shawquia Jackson
(74) *Attorney, Agent, or Firm* — Lee & Morse, P.C.

(57) ABSTRACT

A material for an electroluminescence (EL) device, the material including a compound represented by following Formula 1:

[Formula 1]

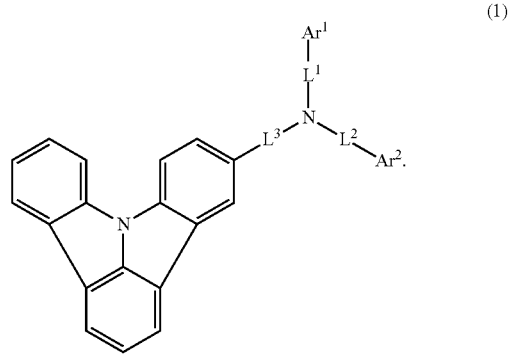

(1)

19 Claims, 1 Drawing Sheet

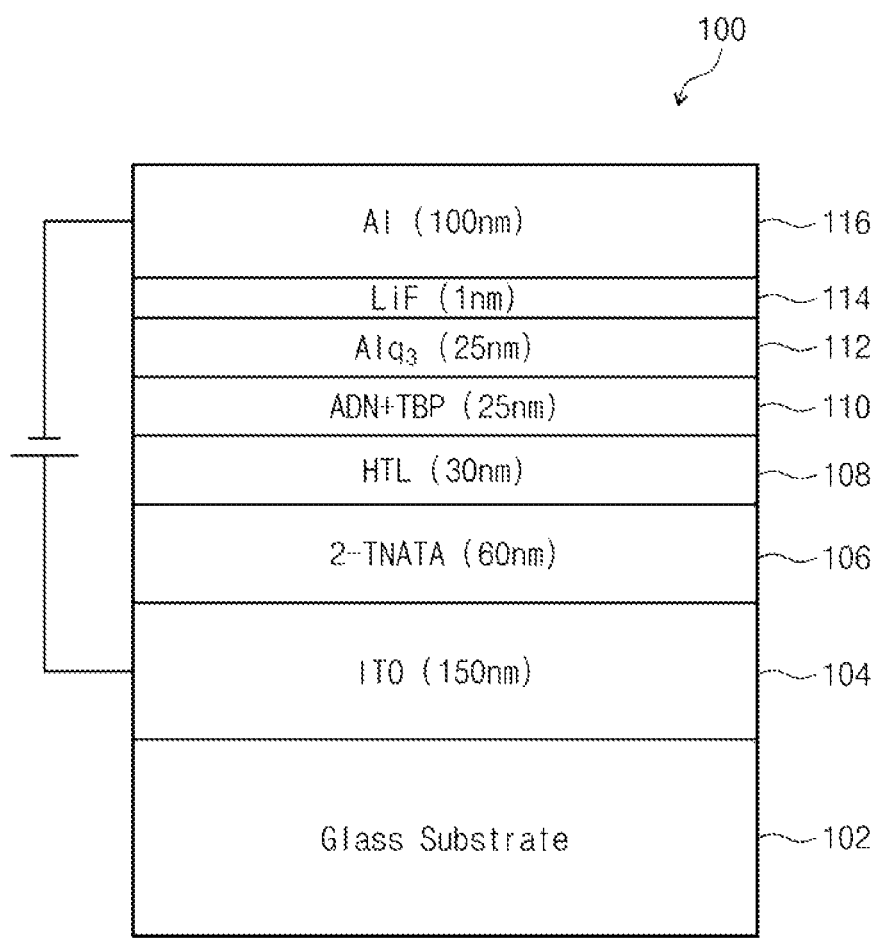

MATERIAL FOR ORGANIC ELECTROLUMINESCENCE DEVICE AND ORGANIC ELECTROLUMINESCENCE DEVICE USING THE SAME

CROSS-REFERENCE TO RELATED APPLICATION

Japanese Patent Application No. 2013-264115, filed on Dec. 20, 2013, in the Japanese Patent Office, and entitled: "Material for Organic Electroluminescence Device and Organic Electroluminescence Device Using the Same," is incorporated by reference herein in its entirety.

BACKGROUND

1. Field

Embodiments relate to a material for an organic electroluminescence device and an organic electroluminescence device using the same.

2. Description of the Related Art

In recent years, organic electroluminescence (EL) displays are one type of image displays that have been actively developed. Unlike a liquid crystal display and the like, the organic EL display is so-called a self-luminescent display that recombines holes and electrons injected from an anode and a cathode in an emission layer to thus emit light from a light-emitting material including an organic compound of the emission layer, thereby performing display.

SUMMARY

Embodiments are directed to a material for an electroluminescence (EL) device, the material including a compound represented by following Formula 1:

[Formula 1]

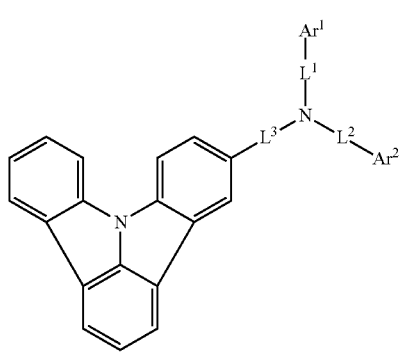

(1)

In Formula 1, $Ar^1$ and $Ar^2$ may independently be a substituted or unsubstituted aryl group, or a substituted or unsubstituted heteroaryl group, and $L^1$, $L^2$, and $L^3$ may independently be a single bond, a substituted or unsubstituted aryl group, or a substituted or unsubstituted heteroaryl group. At least one of $Ar^1$, $Ar^2$, $L^1$, $L^2$, and $L^3$ may be a substituted or unsubstituted heteroaryl group.

At least one of $Ar^1$ and $Ar^2$ may be a substituted or unsubstituted heteroaryl group, and $L^1$, $L^2$, and $L^3$ may independently be a single bond, a substituted or unsubstituted aryl group having 6 to 18 ring carbon atoms.

$Ar^1$ and $Ar^2$ may independently be a substituted or unsubstituted aryl group having 6 to 24 ring carbon atoms, a substituted or unsubstituted carbazolyl group, a substituted or unsubstituted dibenzofuryl group, or a substituted or unsubstituted dibenzothienyl group.

Embodiments are also directed to an organic electroluminescence (EL) device comprising a material that includes a compound represented by the following Formula 1:

[Formula 1]

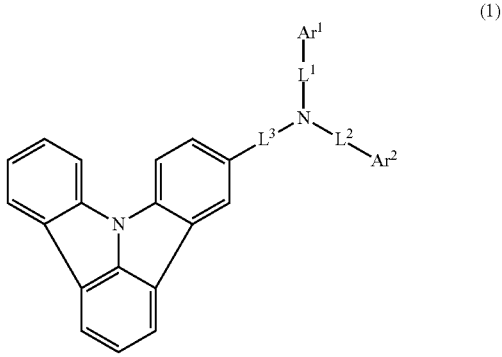

(1)

The material may be a hole transport material.

The material may be in a layer disposed between an emission layer and an anode.

BRIEF DESCRIPTION OF THE DRAWINGS

Features will become apparent to those of skill in the art by describing in detail example embodiments with reference to the attached drawing, in which:

FIG. 1 illustrates a schematic diagram of an organic EL device 100 according to an example embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

The material for an organic EL device according to an example embodiment includes an amine compound represented by the following Formula 1.

[Formula 1]

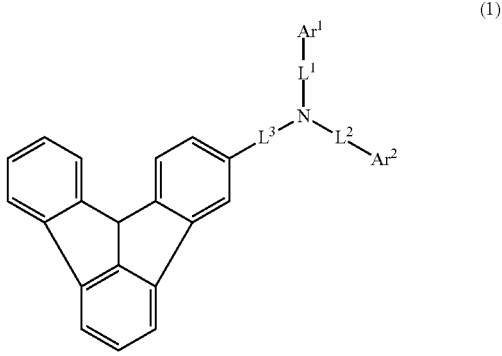

(1)

According to the present example embodiment, in Formula 1, $Ar^1$ and $Ar^2$ are independently a substituted or unsubstituted aryl group, or a substituted or unsubstituted heteroaryl group. $L^1$, $L^2$, and $L^3$ are independently a single bond, a substituted or unsubstituted aryl group, or a substituted or unsubstituted heteroaryl group.

In an example embodiment, at least one of $Ar^1$, $Ar^2$, $L^1$, $L^2$, and $L^3$ is a substituted or unsubstituted heteroaryl group. In an example embodiment, at least one of $Ar^1$ and $Ar^2$ is a substituted or unsubstituted heteroaryl group.

In Formula 1, examples of the aryl group in the "substituted or unsubstituted aryl group" of $Ar^1$ and $Ar^2$ include a phenyl group, a naphthyl group, an anthracenyl group, a phenanthryl group, a biphenyl group, a terphenyl group, a quaterphenyl group, a quinquephenyl group, a sexiphenyl group, a fluorenyl group, a triphenylenyl group, a biphenylenyl group, a pyrenyl group, a benzofluoranthenyl group, a chrysenyl group, etc. In an example embodiment, the aryl group may be an aryl group having 6 to 24 ring carbon atoms, for example, the phenyl group, the naphthyl group, the anthracenyl group, the phenanthryl group, the biphenyl group, the terphenyl group, the quaterphenyl group, the fluorenyl group, the triphenylenyl group, the biphenylenyl group, the pyrenyl group, the benzofluoranthenyl group, or the chrysenyl group.

In Formula 1, examples of the heteroaryl group in the "substituted or unsubstituted heteroaryl group" of $Ar^1$ and $Ar^2$ include a benzothiazolyl group, a thiophenyl group, a thienothiophenyl group, a thienothienothiophenyl group, a benzothiophenyl group, a benzofuryl group, a dibenzothiophenyl group, a dibenzofuryl group, a carbazolyl group, a phenoxazyl group, a phenothiazyl group, a pyridyl group, a pyrimidyl group, a triazile group, a quinolinyl group, a quinoxalyl group, etc. In an example embodiment, the heteroaryl group may be the carbazolyl group, the dibenzofuryl group, or the dibenzothienyl group.

In Formula 1, examples of the aryl group in the "substituted or unsubstituted aryl group" and examples of the heteroaryl group in the "substituted or unsubstituted heteroaryl group" of $L^1$, $L^2$ and $L^3$ may be the same as described above. In an example embodiment, $L^1$, $L^2$ and $L^3$ may independently be a single bond, or a substituted or unsubstituted aryl group having 6 to 18 ring carbon atoms. Examples of the aryl group having 6 to 18 ring carbon atoms include a phenyl group, a naphthyl group, an anthracenyl group, a phenanthryl group, a biphenyl group, a terphenyl group, a fluorenyl group, a triphenylenyl group, a biphenylenyl group, a pyrenyl group, a chrysenyl group, etc.

In an example embodiment, examples of the substituent at the aryl group or the heteroaryl group used as $Ar^1$, $Ar^2$, $L^1$, $L^2$, and $L^3$ include an aryl group, a heteroaryl group, an alkyl group, an alkoxy group, a triarylsilyl group, and a trialkylsilyl group. As the aryl group and the heteroaryl group, the same groups as described above may be used.

In Formula 1, examples of the alkyl group substituted at the aryl group or the heteroaryl group used as $Ar^1$, $Ar^2$, $L^1$, $L^2$, and $L^3$ may include an alkyl group having 1 to 30 carbon atoms, for example, a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, a n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantly group, a 2-ethyldecyl group, a 2-butyldecyl group, a 2-hexyldecyl group, a 2-octyldecyl group, an n-undecyl group, an n-dodecyl group, a 2-ethyldocecyl group, a 2-butyldodecyl group, a 2-hexyldodecyl group, a 2-octyldodecyl group, an n-tridecyl group, an n-tetradecyl group, an n-pentadecyl group, an n-hexadecyl group, a 2-ethylhexadecyl group, 2-butylhexadecyl group, a 2-hexylhexadecyl group, a 2-octylhexadecyl group, an n-heptadecyl group, an n-octadecyl group, an n-nanodecyl group, an n-icosyl group, a 2-ethylicosyl group, a 2-butylicosyl group, a 2-hexylicosyl group, a 2-octylicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc.

In Formula 1, examples of the alkoxy group substituted at the aryl group or the heteroaryl group used as $Ar^1$, $Ar^2$, $L^1$, $L^2$ and $L^3$ include an alkoxy group having 1 to 30 carbon atoms, for example, a methoxy group, an ethoxy group, an n-propoxy group, an i-propoxy group, an n-butoxy group, an s-butoxy group, a t-butoxy group, an i-butoxy group, a 2-ethylbutoxy group, a 3,3-dimethylbutoxy group, an n-pentyloxy group, an i-pentyloxy group, a neopentyloxy group, a t-pentyloxy group, a cyclopentyloxy group, a 1-methylpentyloxy group, a 3-methylpentyloxy group, a 2-ethylpentyloxy group, a 4-methyl-2-pentyloxy group, an n-hexyloxy group, a 1-methylhexyloxy group, a 2-ethylhexyloxy group, a 2-butylhexyloxy group, a cyclohexyloxy group, a 4-methylcyclohexyloxy group, a 4-t-butylcyclohexyloxy group, an n-heptyloxy group, a 1-methylheptyloxy group, a 2,2-dimethylheptyloxy group, a 2-ethylheptyloxy group, 2-butylheptyloxy group, an n-octyloxy group, a t-octyloxy group, a 2-ethyloctyloxy group, a 2-butyloctyloxy group, a 2-hexyloctyloxy group, a 3,7-dimethyloctyloxy group, a cyclooctyloxy group, an n-nonyloxy group, an n-decyloxy group, an adamantyloxy group, a 2-ethyldecyloxy group, a 2-butyldecyloxy group, a 2-hexyldecyloxy group, a 2-octyldecyloxy group, an n-undecyloxy group, an n-dodecyloxy group, a 2-ethyldodecyloxy group, a 2-butyldodecyloxy group, a 2-hexyldodecyloxy group, a 2-octyldodecyloxy group, an n-tridecyloxy group, an n-tetradecyloxy group, an n-pentadecyloxy group, an n-hexadecyloxy group, a 2-ethylhexadecyloxy group, a 2-butylhexadecyloxy group, a 2-hexylhexadecyloxy group, a 2-octylhexadecyloxy group, an n-heptadecyloxy group, an n-octadecyloxy group, an n-nonadecyloxy group, an n-icosyloxy group, a 2-ethylicosyloxy group, a 2-butylicosyloxy group, a 2-hexylicosyloxy group, a 2-octylicosyloxy group, an n-henicosyloxy group, an n-docosyloxy group, an n-tricosyloxy group, an n-tetracosyloxy group, an n-pentacosyloxy group, an n-hexacosyloxy group, an n-heptacosyloxy group, an n-octacosyloxy group, an n-nonacosyloxy group, an n-triacontyloxy group, etc.

In Formula 1, examples of the aryl group of the triarylsilyl group substituted at the aryl group or the heteroaryl group used as $Ar^1$, $Ar^2$, $L^1$, $L^2$, and $L^3$ include the same groups as described above, and may include a triphenylsilyl group, etc.

In Formula 1, examples of the alkyl group of the trialkylsilyl group substituted at the aryl group or the heteroaryl group used as $Ar^1$, $Ar^2$, $L^1$, $L^2$, and $L^3$ may include the same groups as described above, and may include a trimethylsilyl group, a triethylsilyl group, a triisopropylsilyl group, a t-butyldimethylsilyl group, etc.

According to an example embodiment, the compound represented by Formula 1 has the above-described structure and has a molecular weight of, for example, less than or equal to about 1,000 for application in a vacuum deposition process.

According to an example embodiment, the material for an organic EL device includes an amine moiety combined at position 5 of an indolo[3,2,1-jk]carbazolyl moiety with high electron tolerance as a hole transport material. An organic EL device including the material may be driven at a low voltage, and may have high efficiency and long life.

The material for an organic EL device according to an example embodiment may include one or more compounds having the following structures.

[Formula 3]

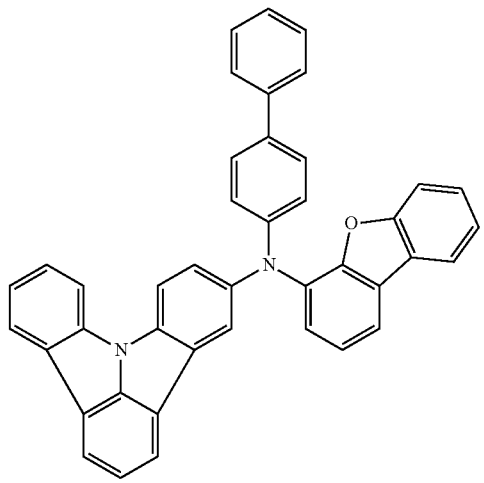

1

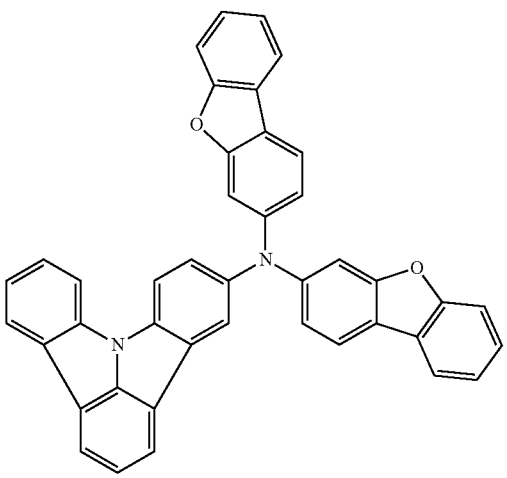

3

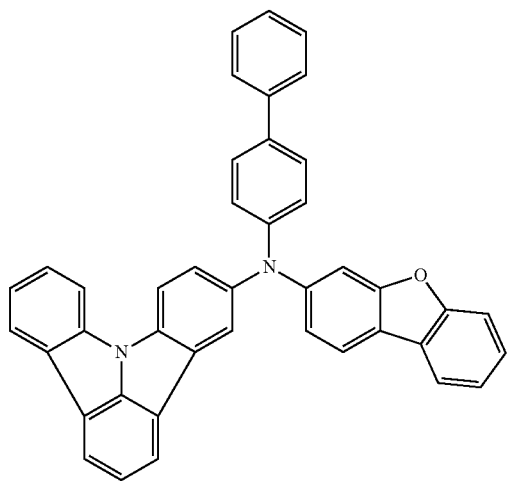

2

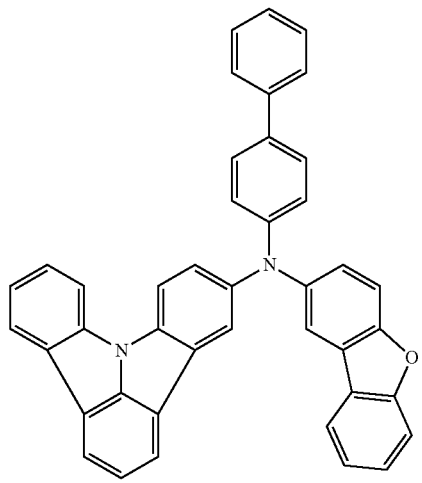

4

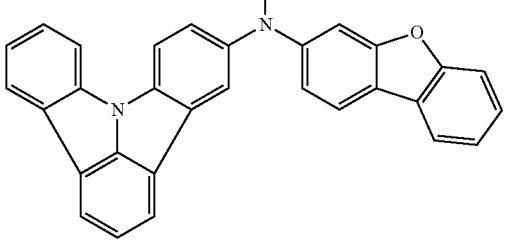

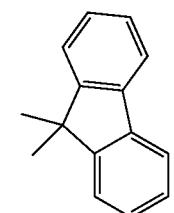

5

6
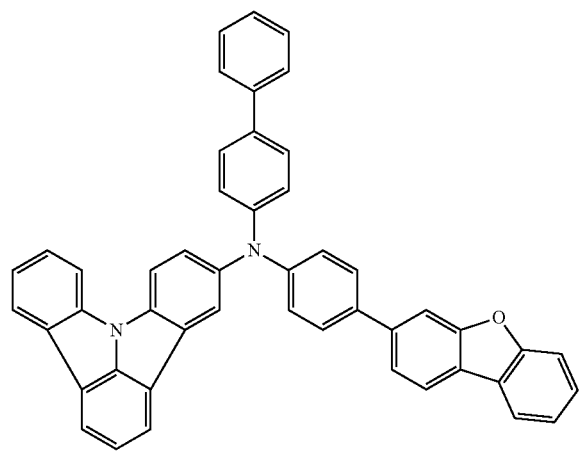
7
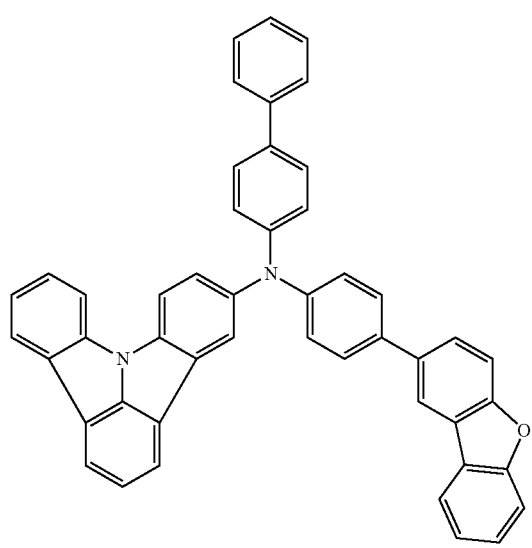
8
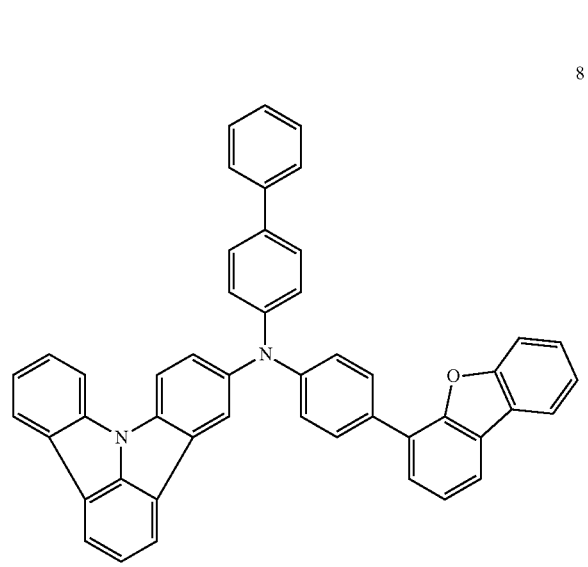
5
10
15
20
25
30
35
The material for an organic EL device according to an example embodiment may include one or more compounds having the following structures.
[Formula 4]
9
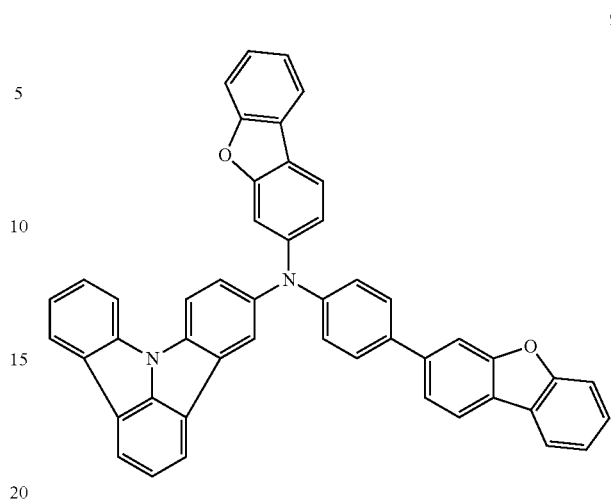
10
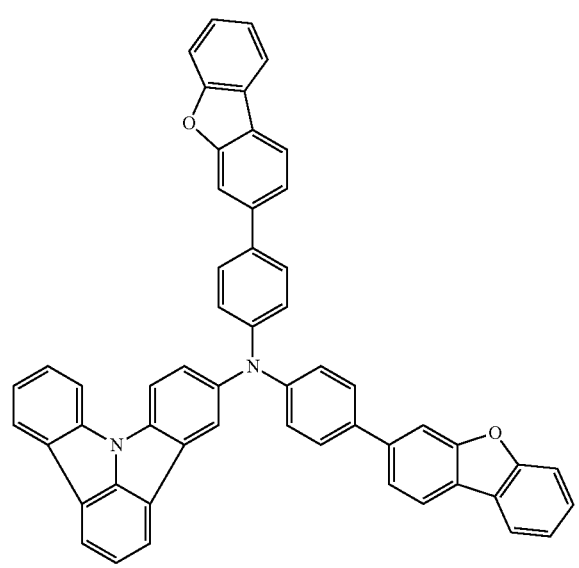

11
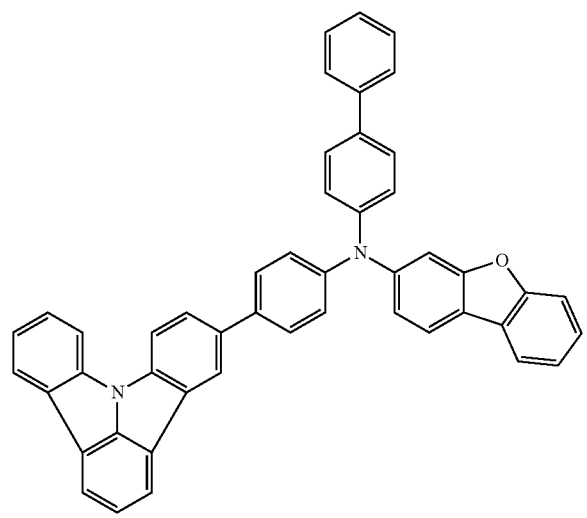
12
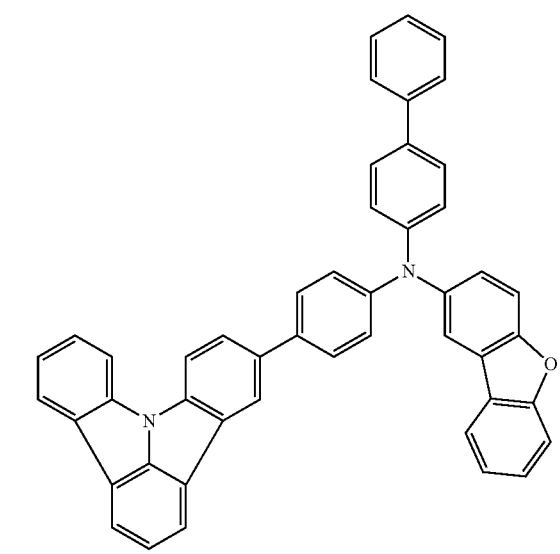
13
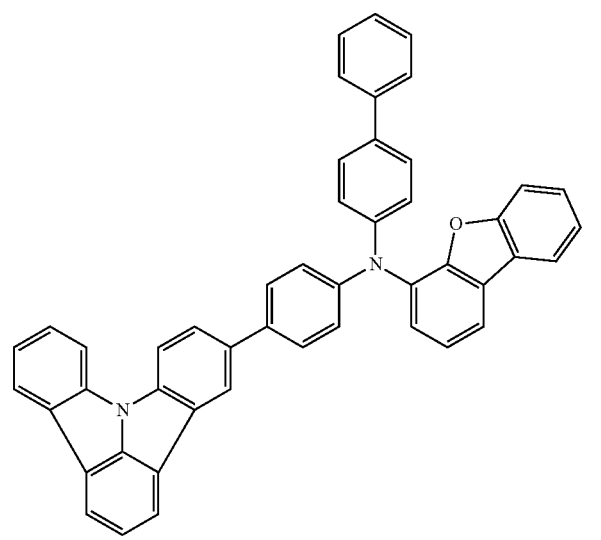
14
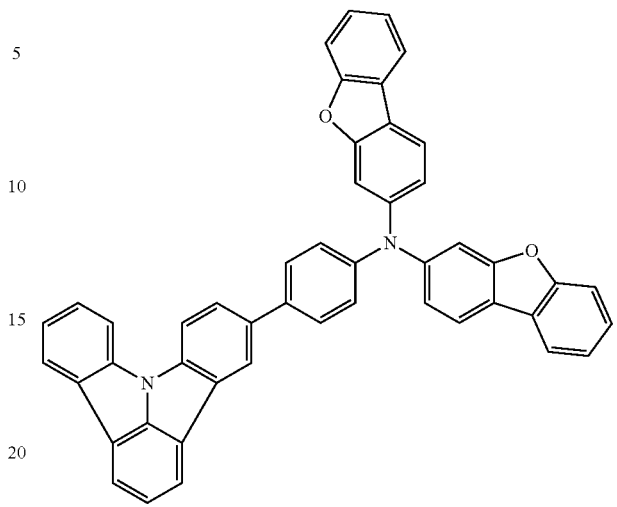
15
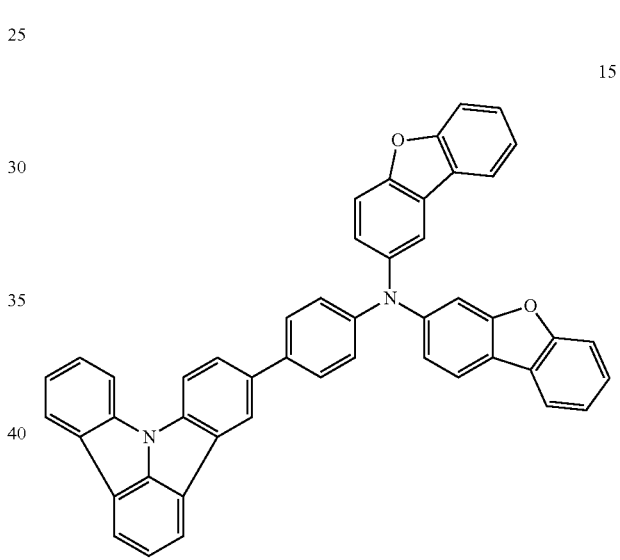
16
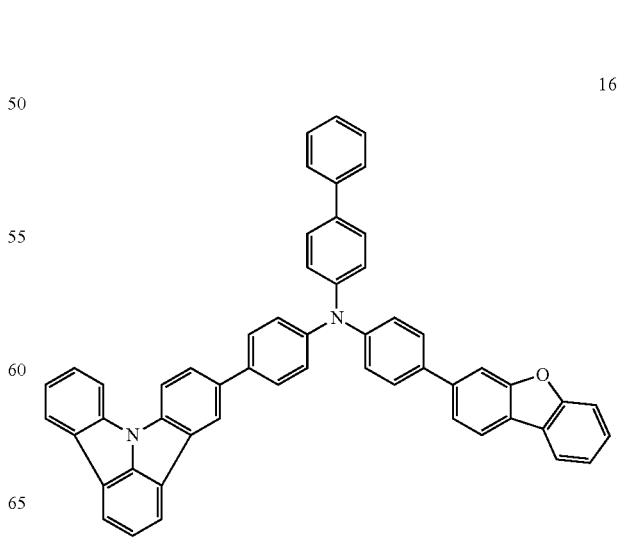

17
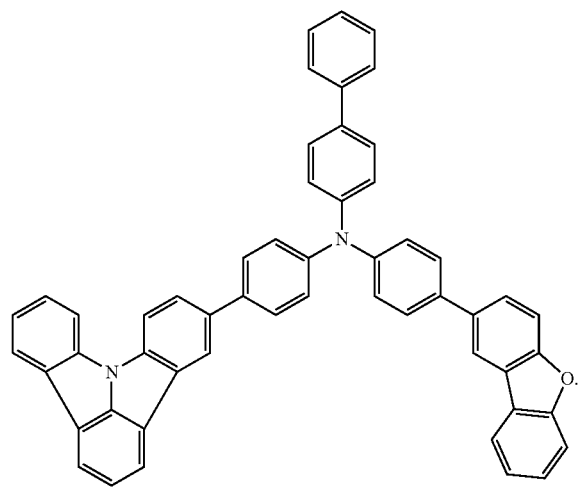
The material for an organic EL device according to an example embodiment may include one or more compounds having the following structures.
[Formula 5]
18
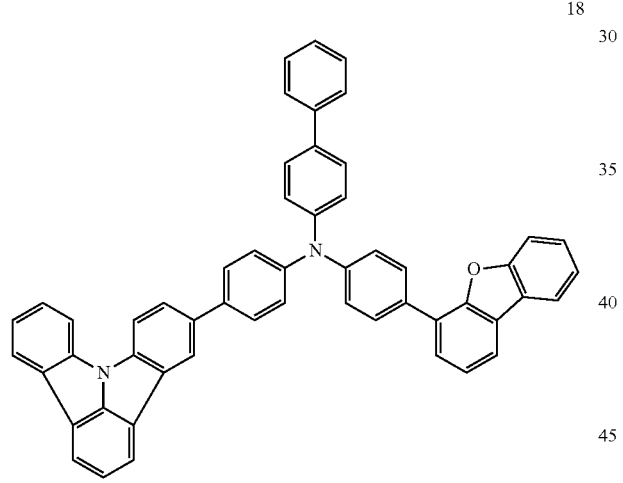
19
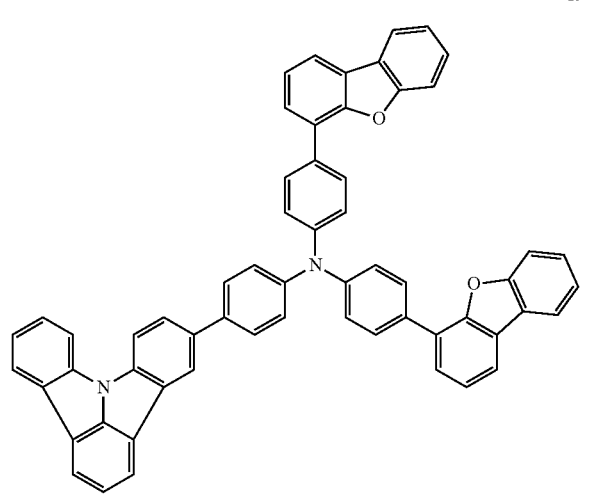
20
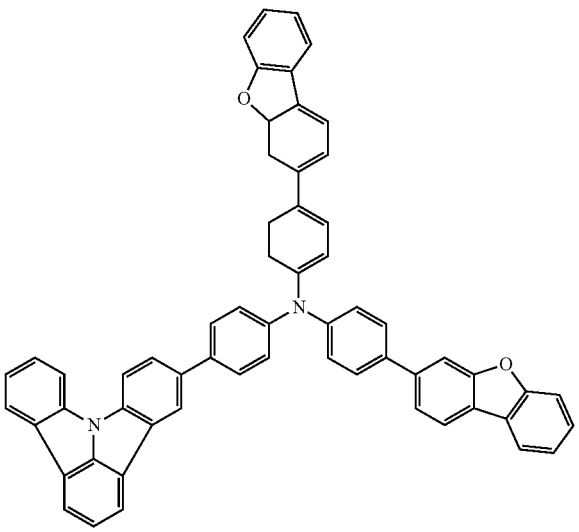
21
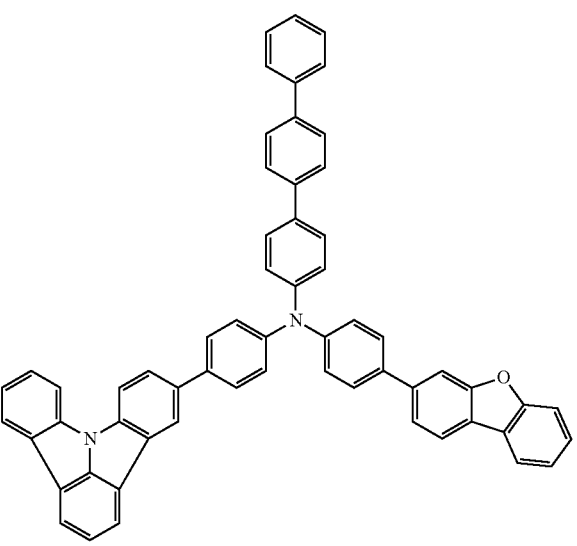

[Formula 6]
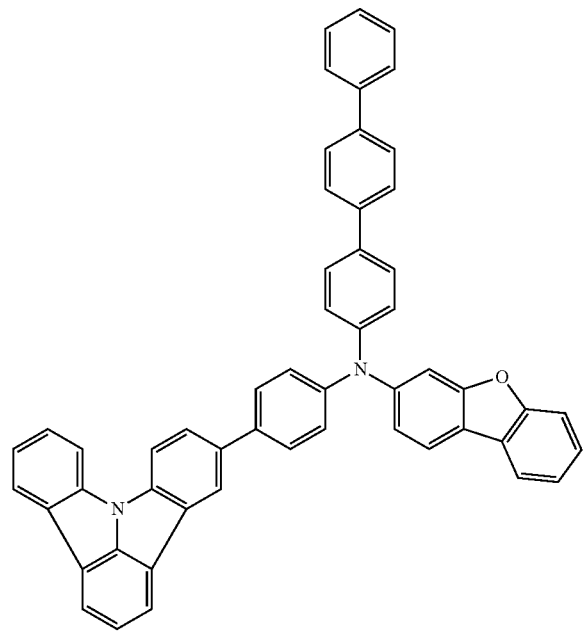
22
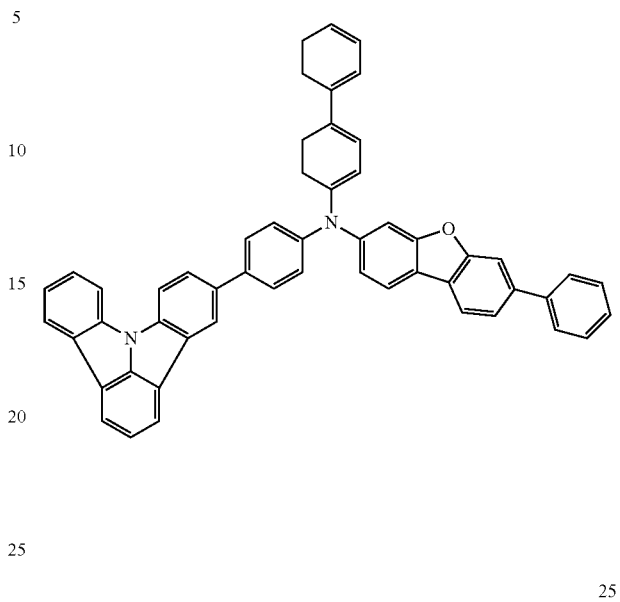
24
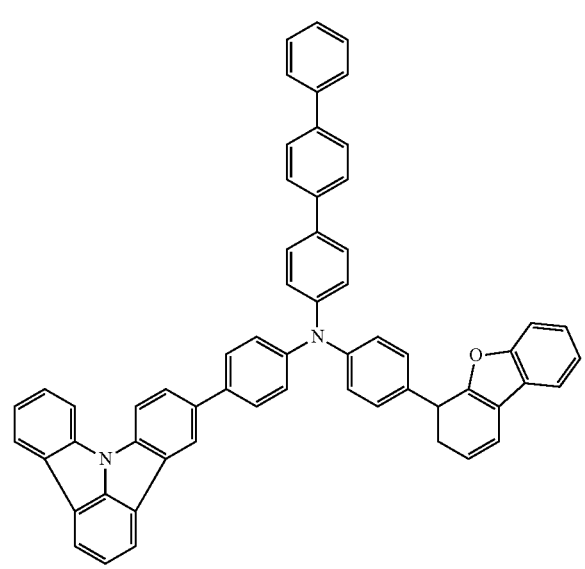
23
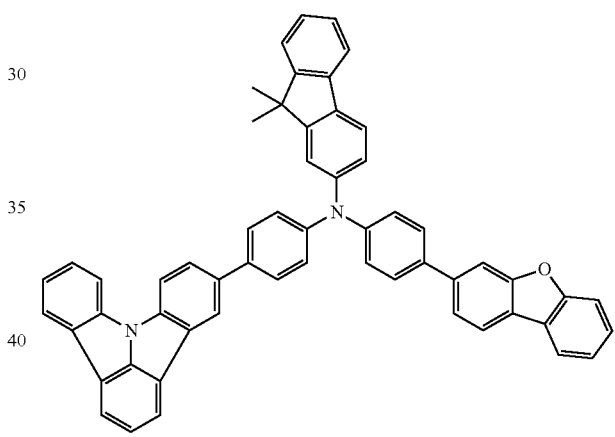
25
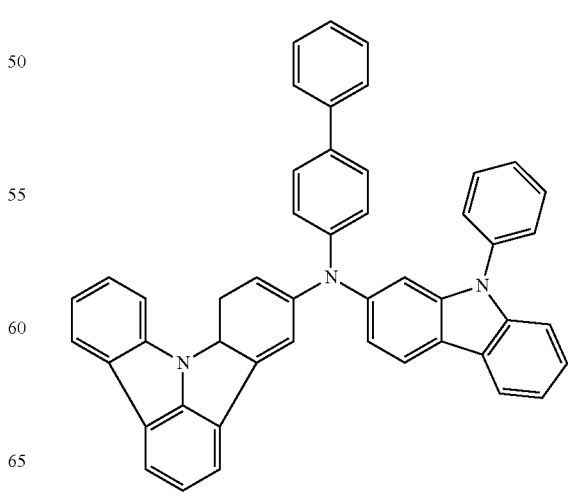
26
The material for an organic EL device according to an example embodiment may include one or more compounds having the following structures.

27
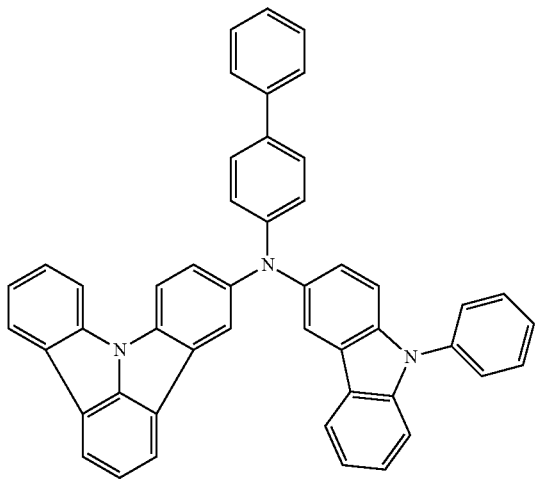
28
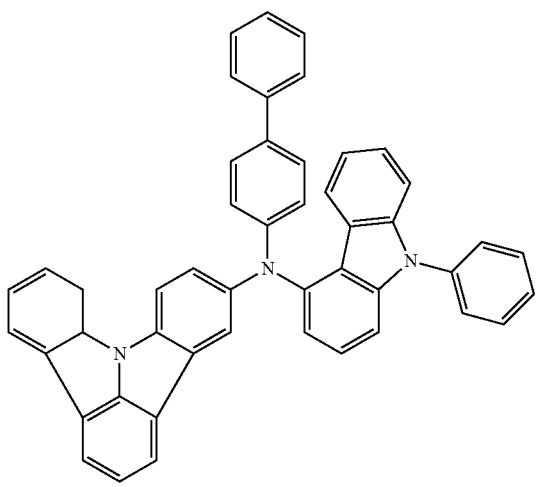
29
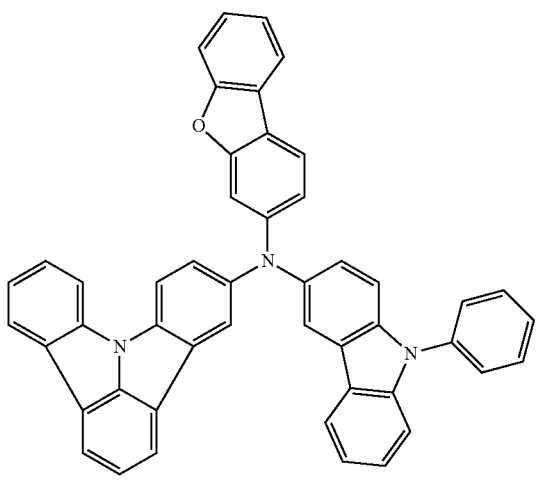
30
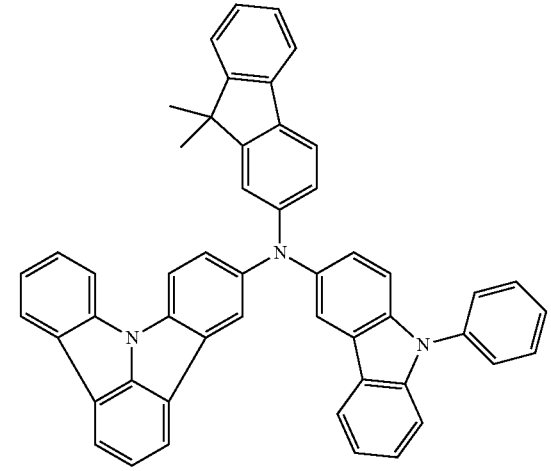
31
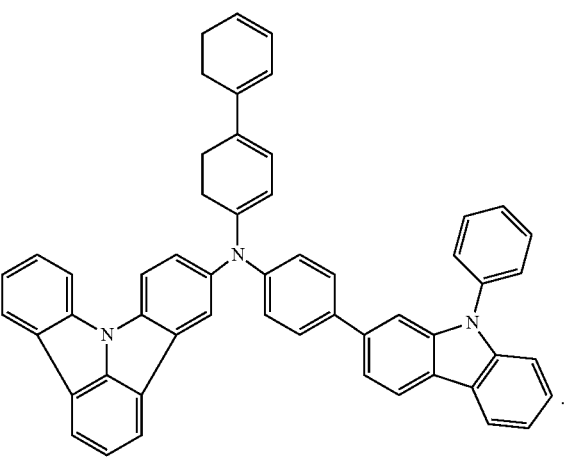
The material for an organic EL device according to an example embodiment may include one or more compounds having the following structures.
[Formula 7]
32
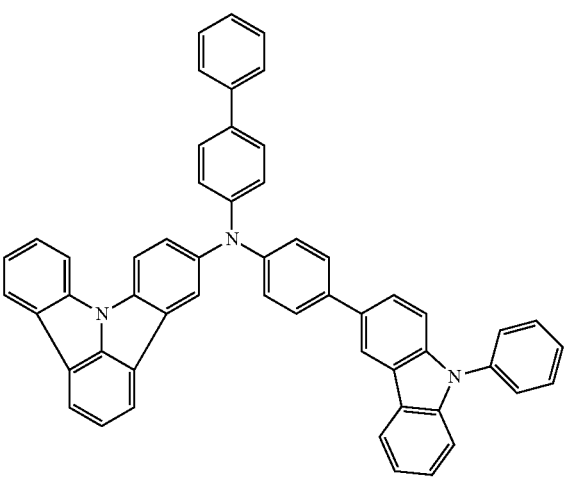

33
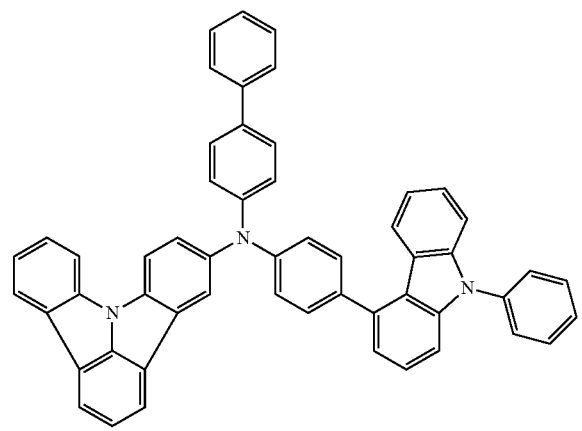
34
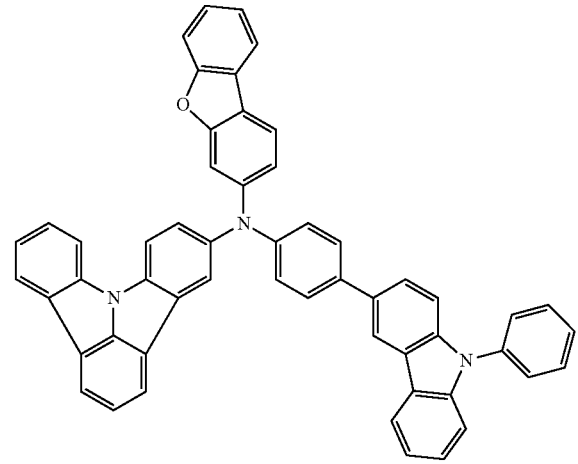
35
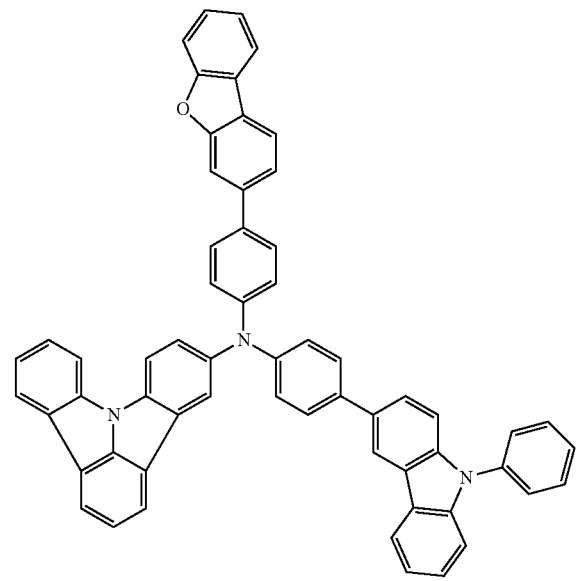
36
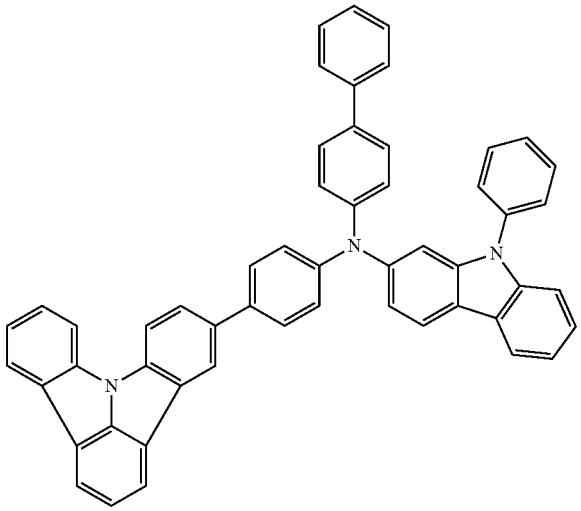
37
38
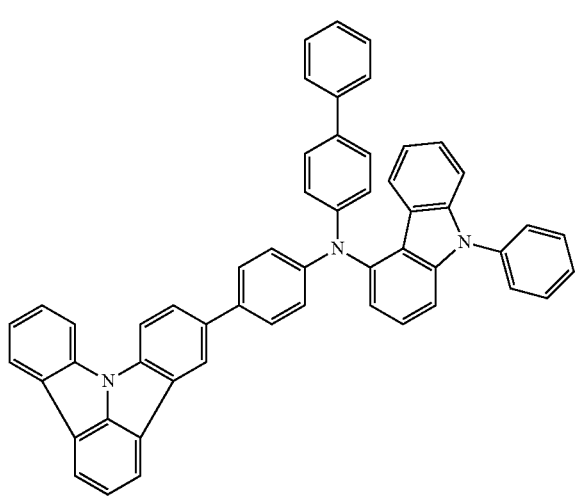

39
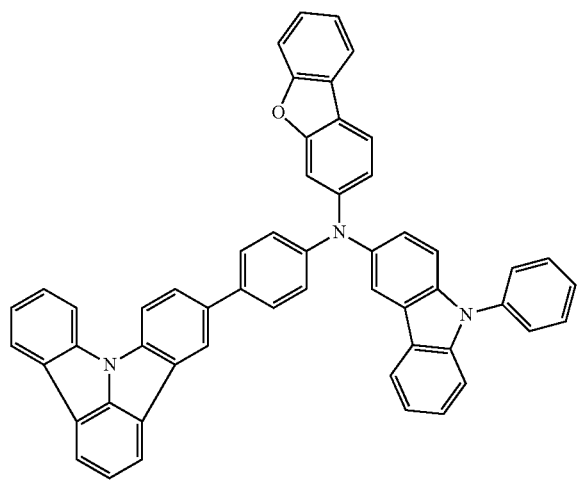
40
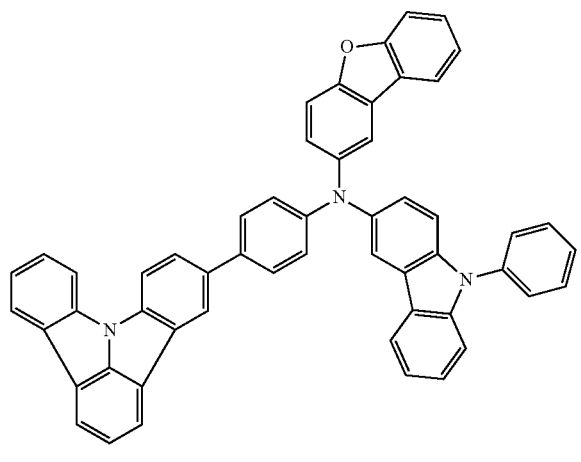
The material for an organic EL device according to an example embodiment may include one or more compounds having the following structures.
[Formula 8]
41
42
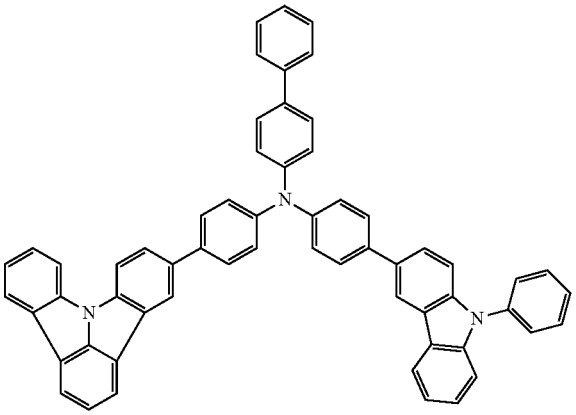
43
44
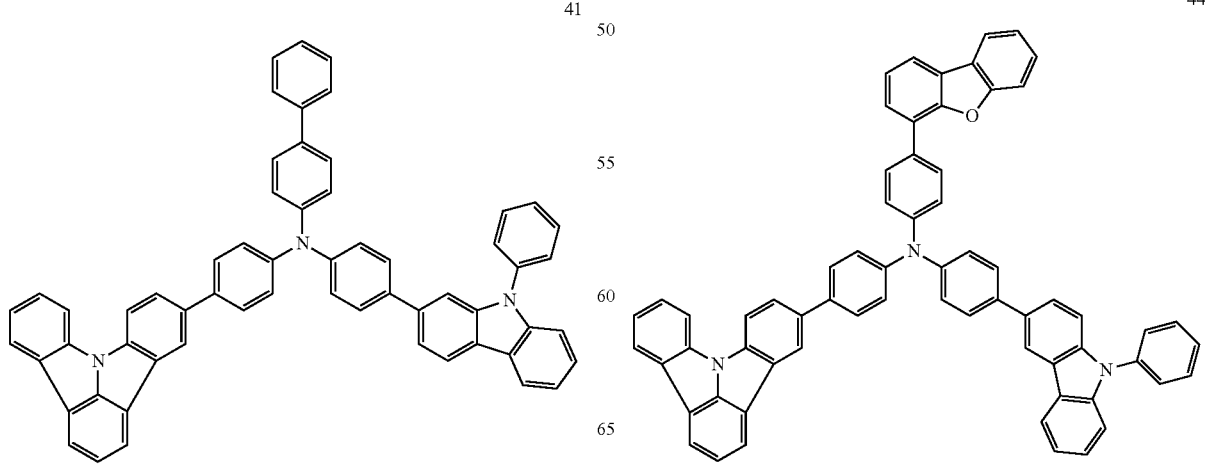

45
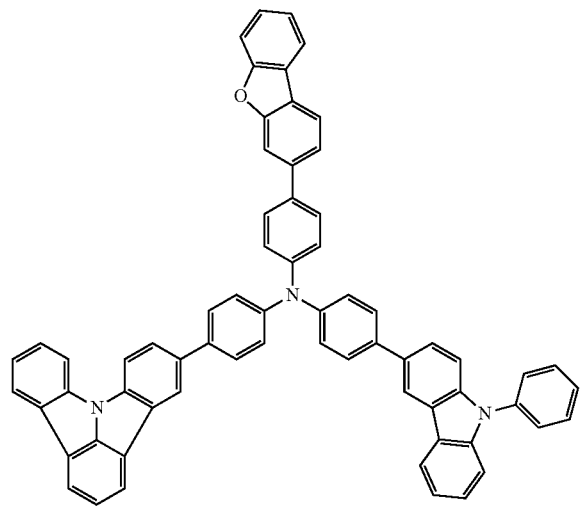
46
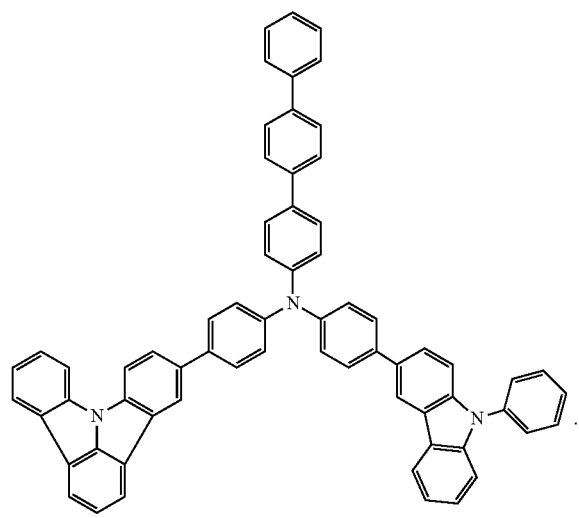
[Formula 9]
47
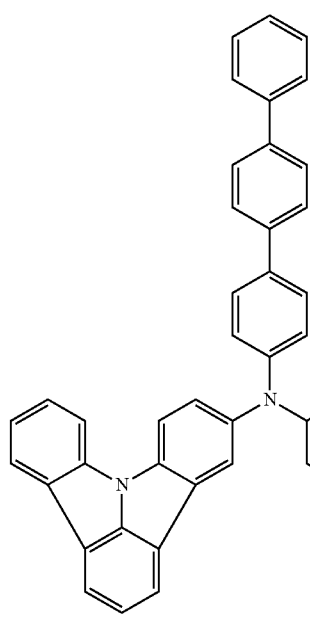
48
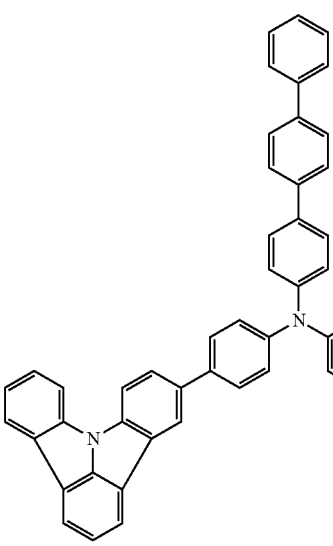
The material for an organic EL device according to an example embodiment may include one or more compounds having the following structures.

49
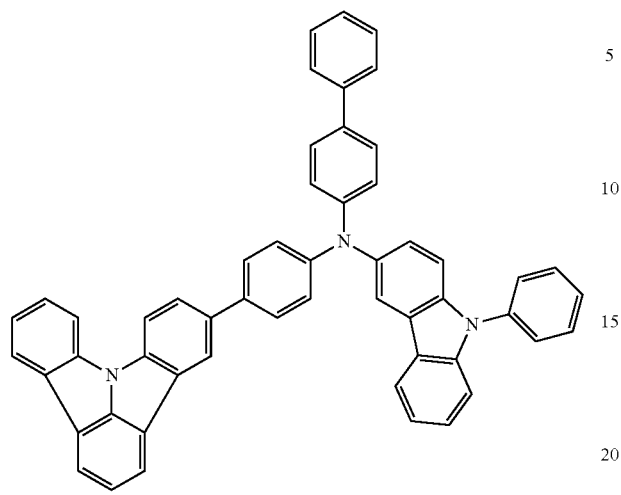
50
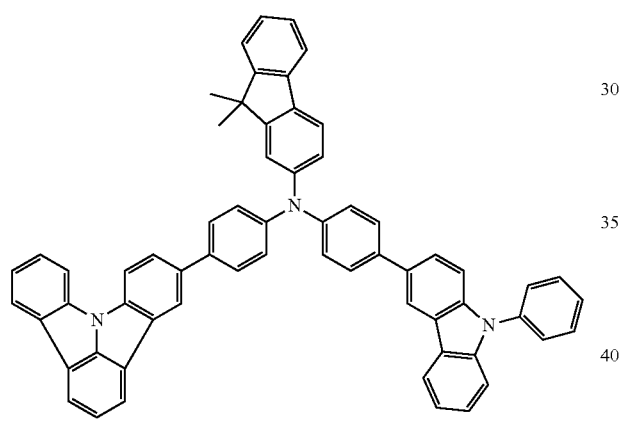
51
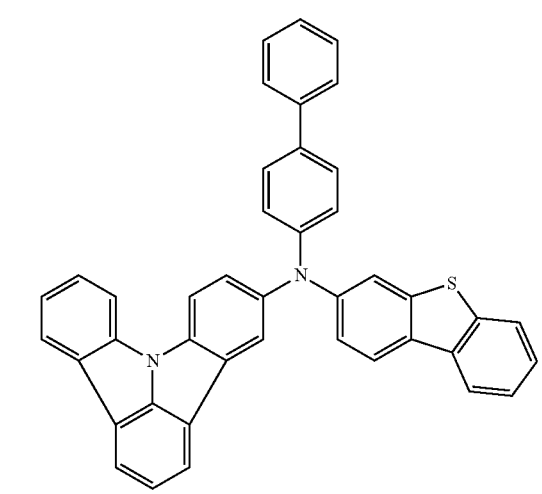
52
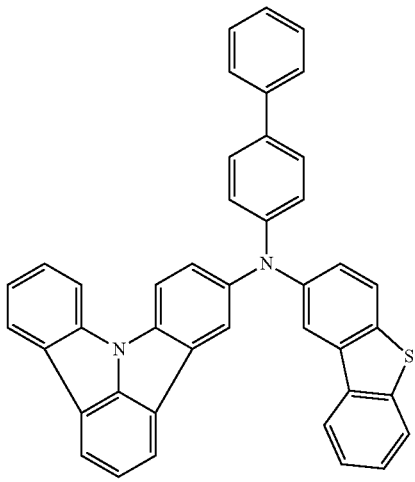
53
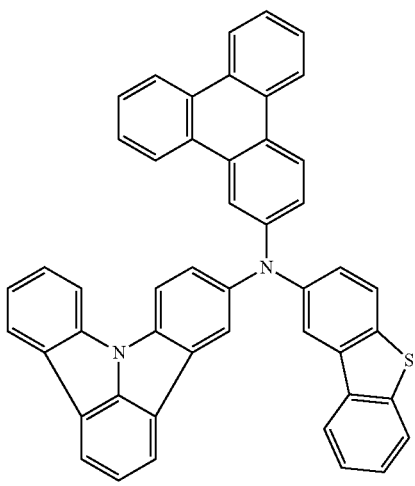
54
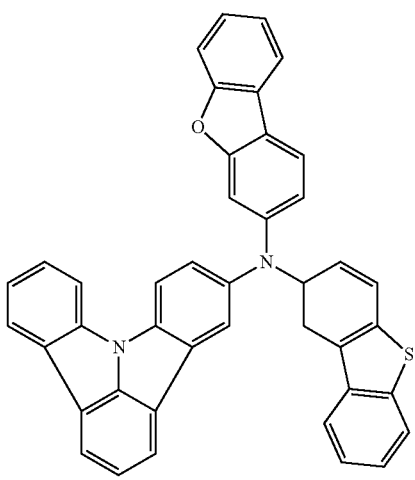

55
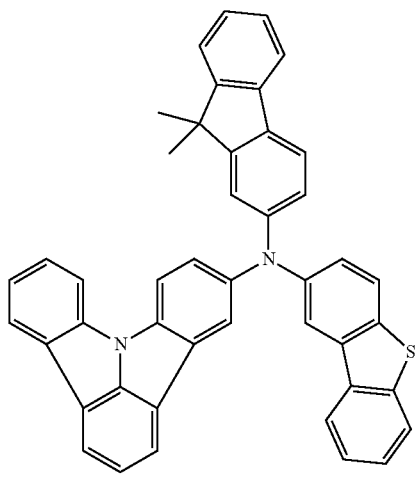
The material for an organic EL device according to an example embodiment may include one or more compounds having the following structures.
[Formula 10]
56
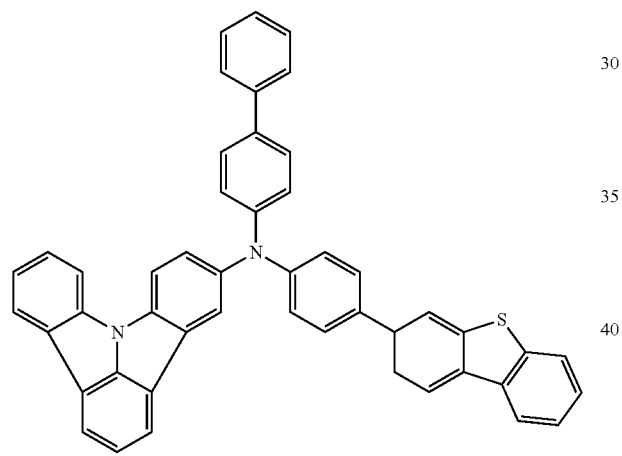
57
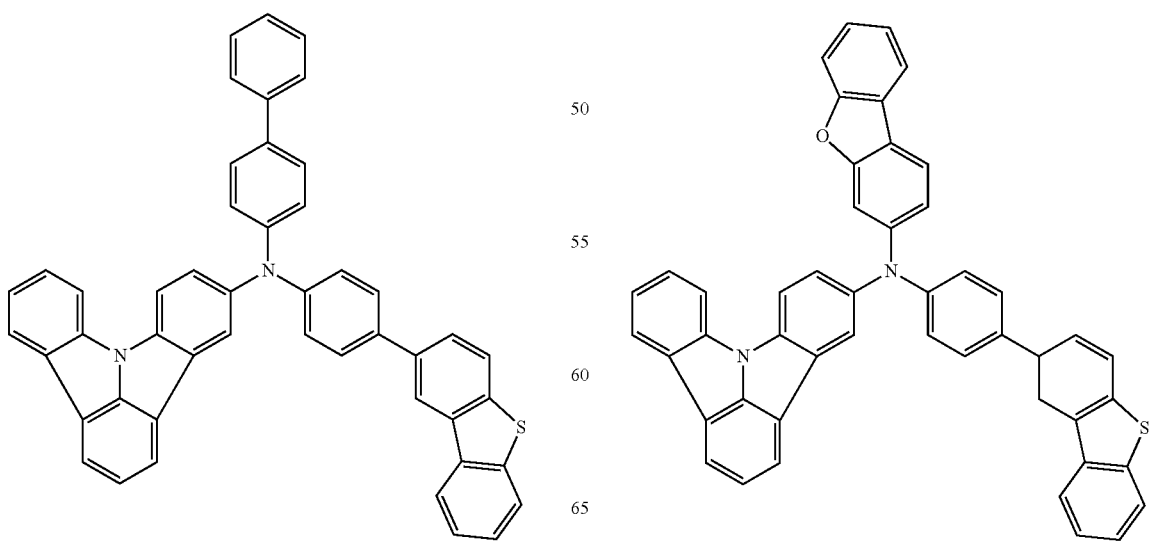
58
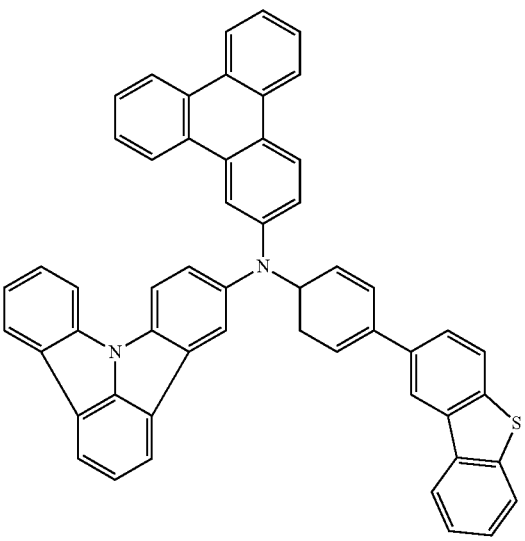
59
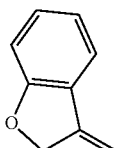

27
-continued
60
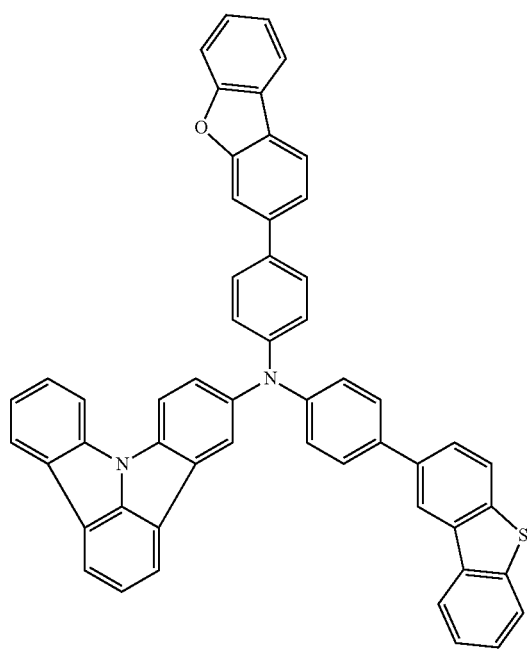
28
-continued
62
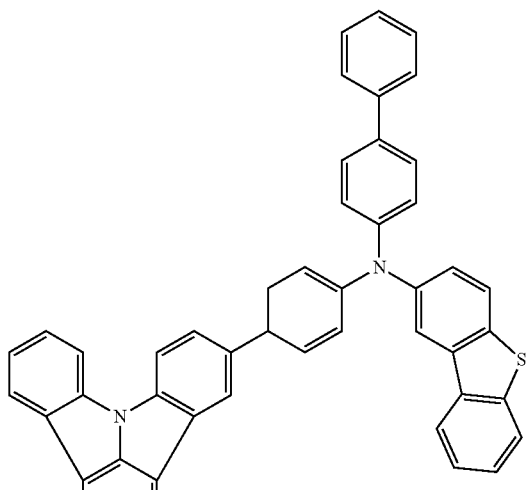
61
63
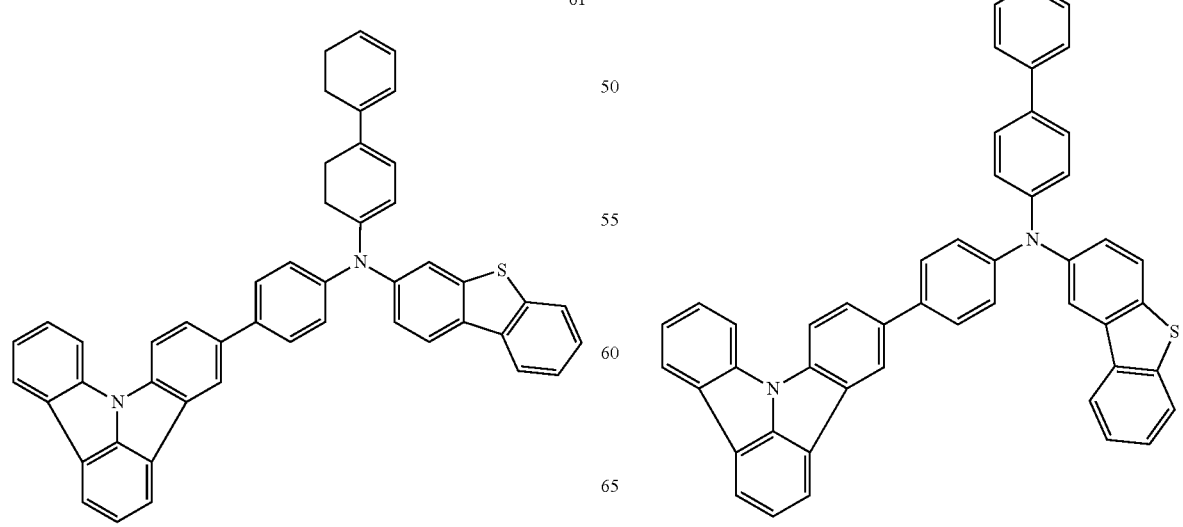

64
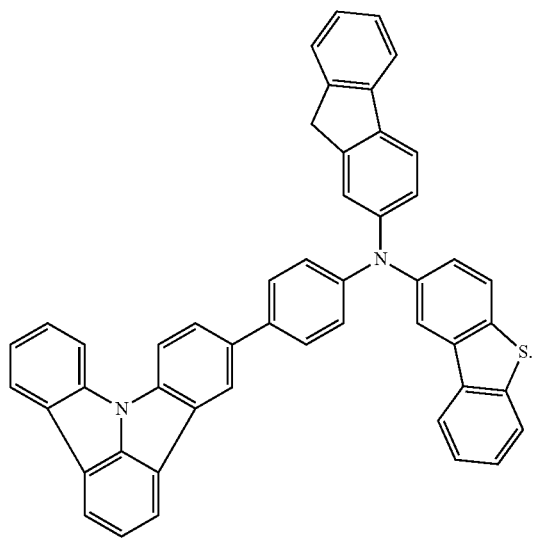
The material for an organic EL device according to an example embodiment may include one or more compounds having the following structures.
[Formula 11]
65
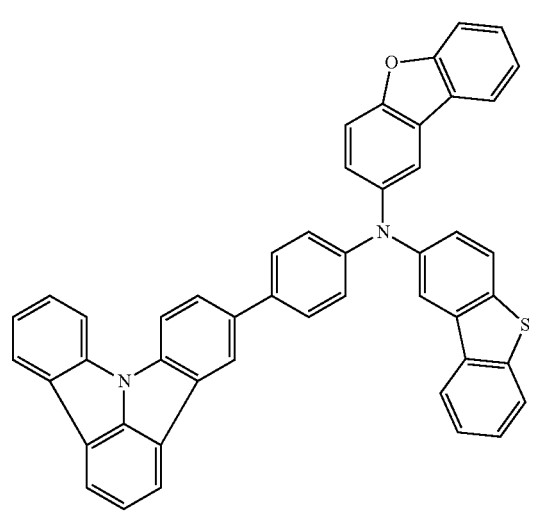
66
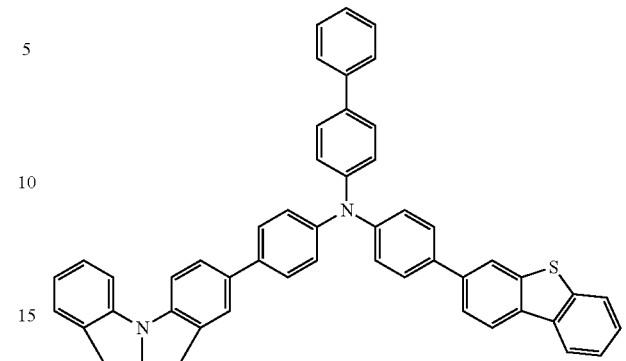
67
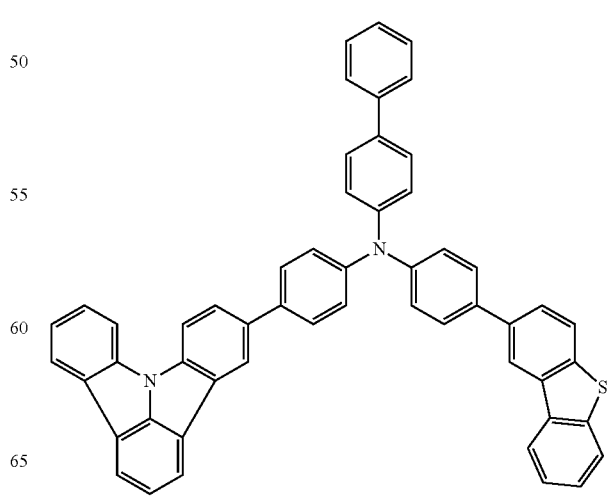
68

69
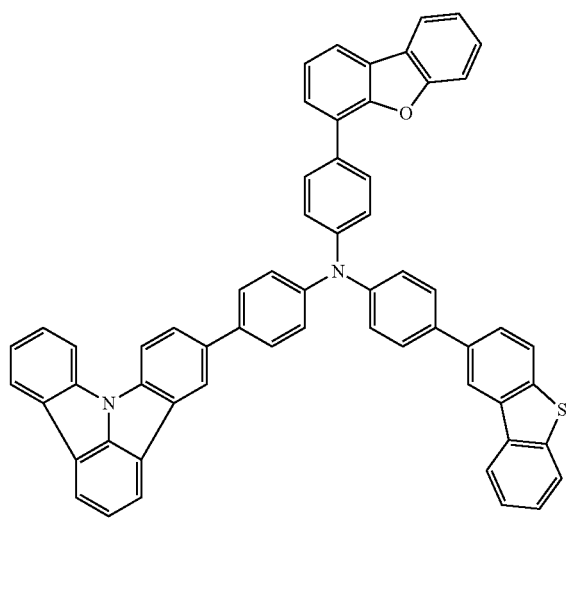
71
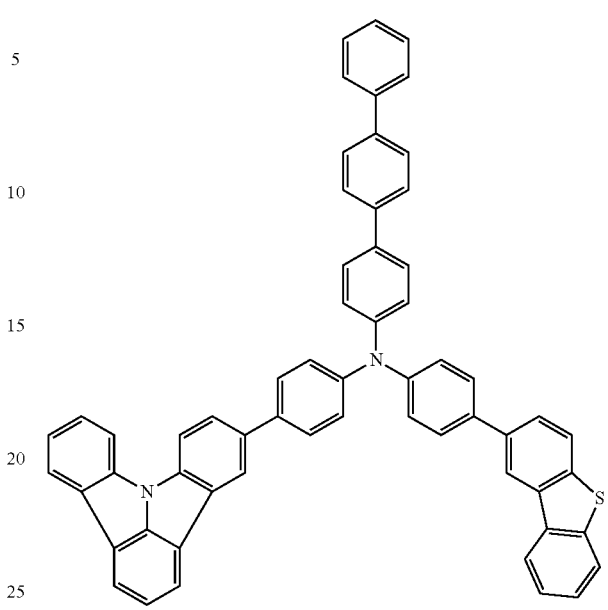
70
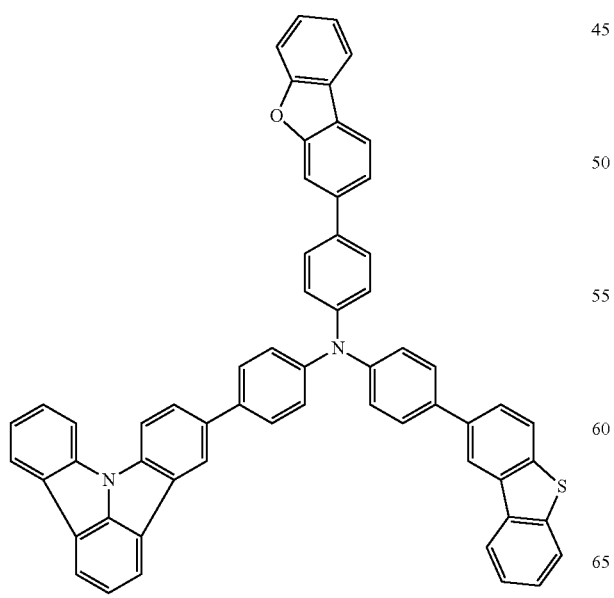
72
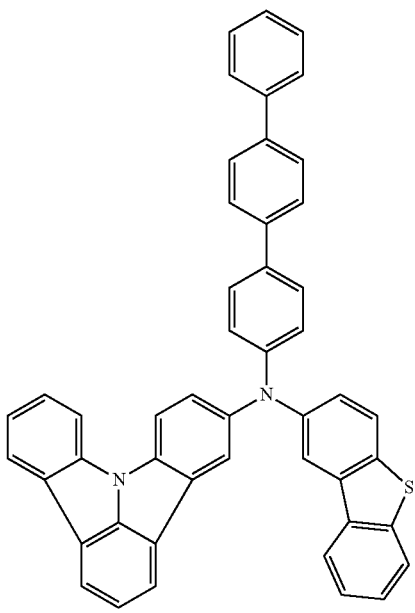

73
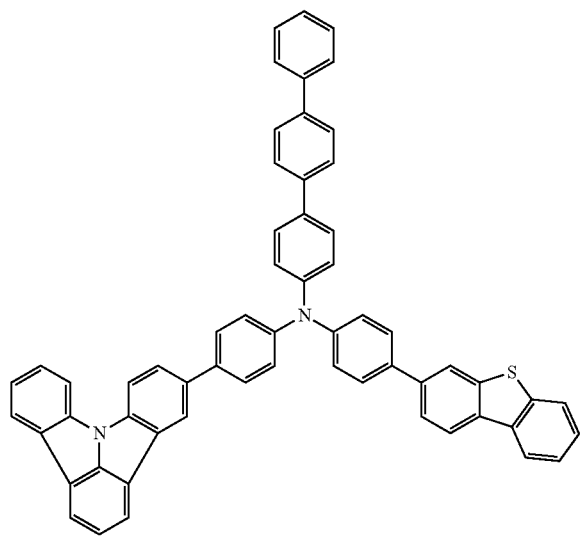
The material for an organic EL device according to an example embodiment may include one or more compounds having the following structures.
[Formula 12]
74
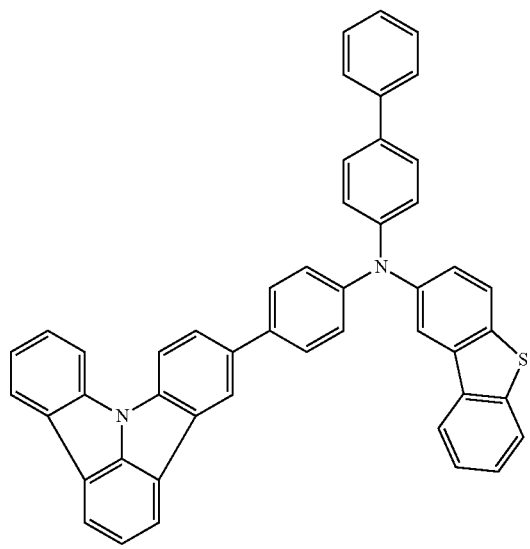
75
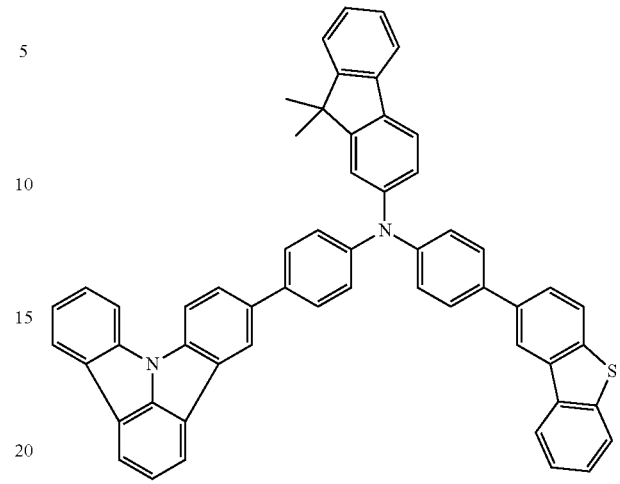
76
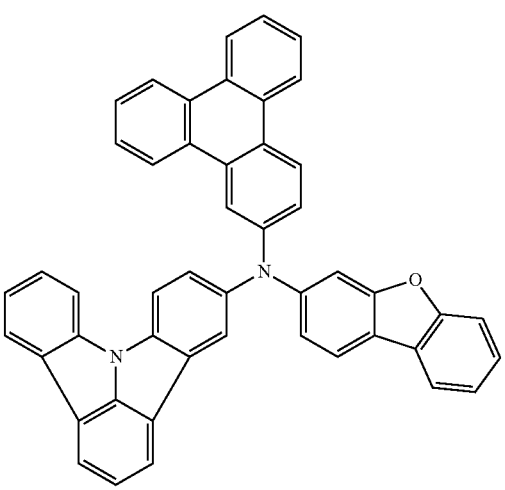
77
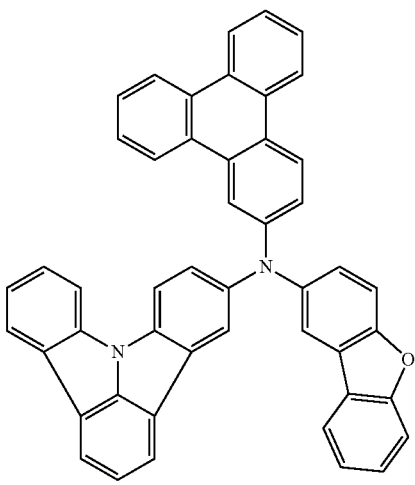

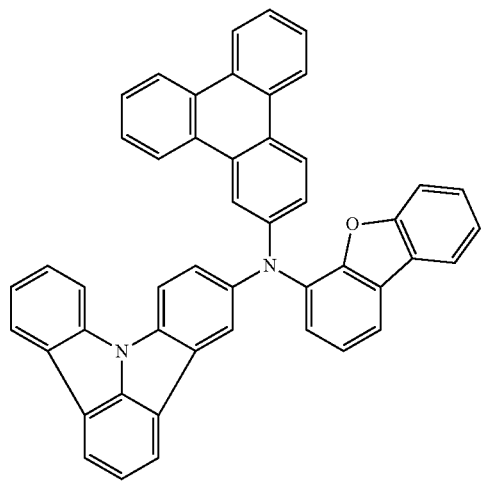
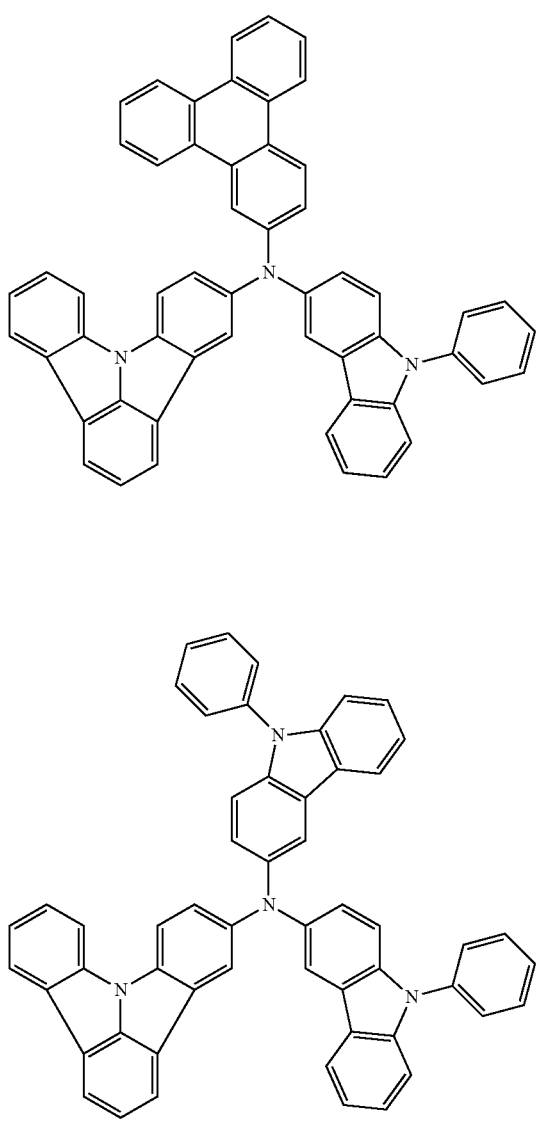
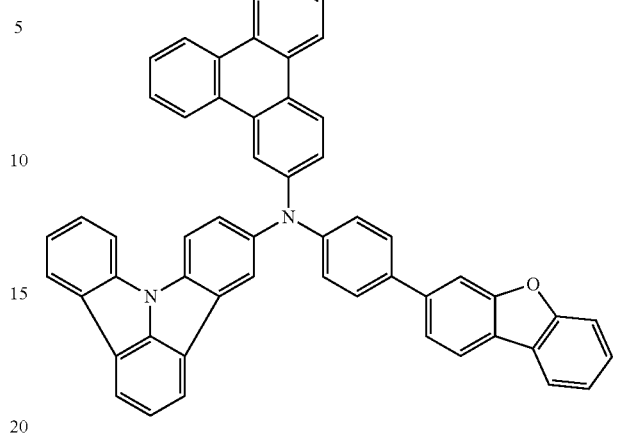
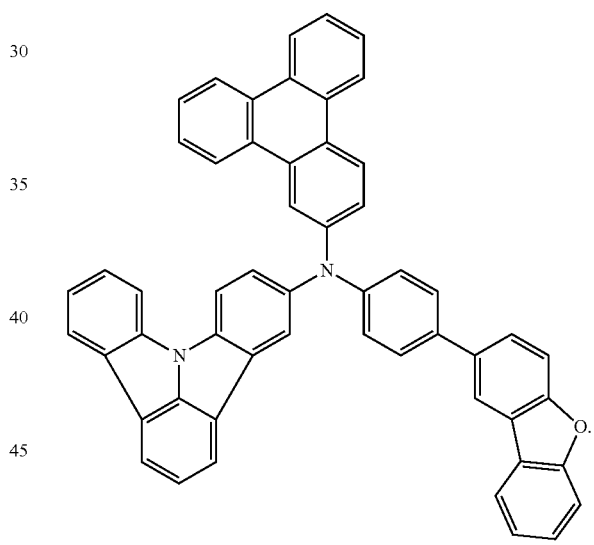
The material for an organic EL device according to an example embodiment may include one or more compounds having the following structures.

[Formula 13]
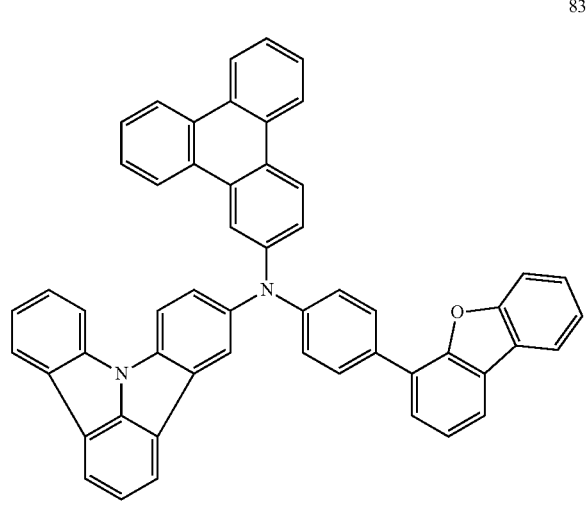
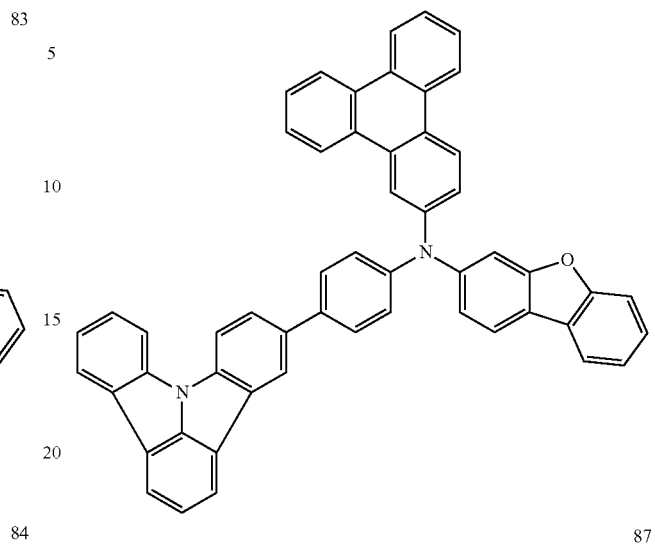
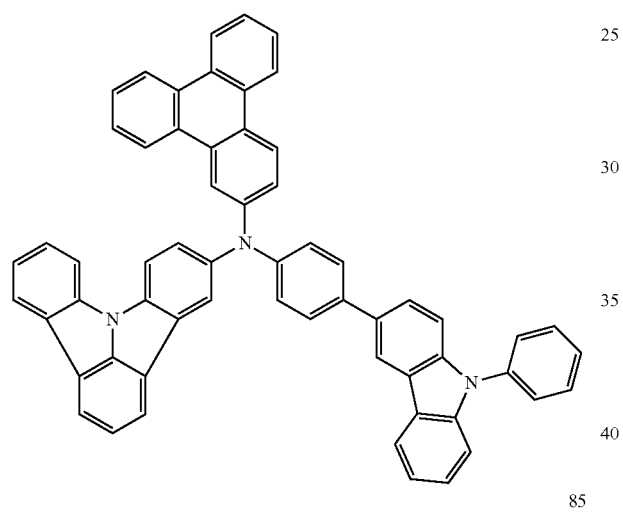
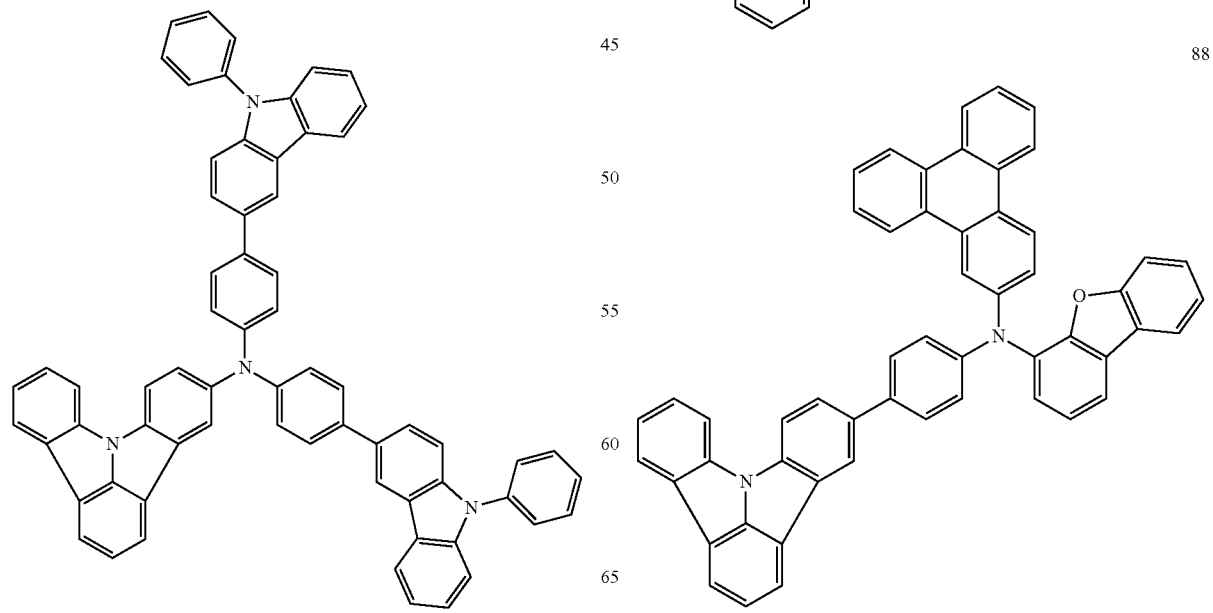

[Formula 14]
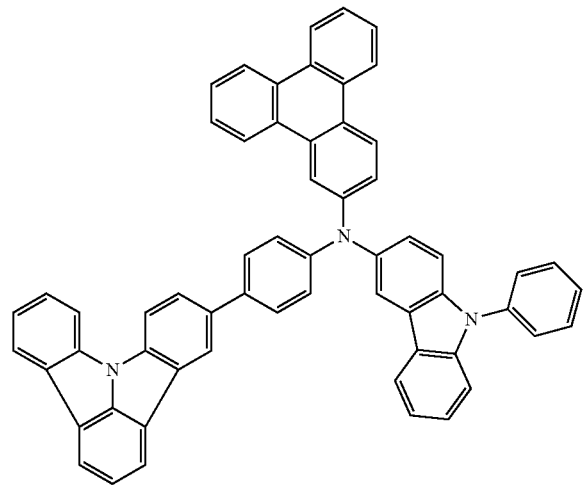
89
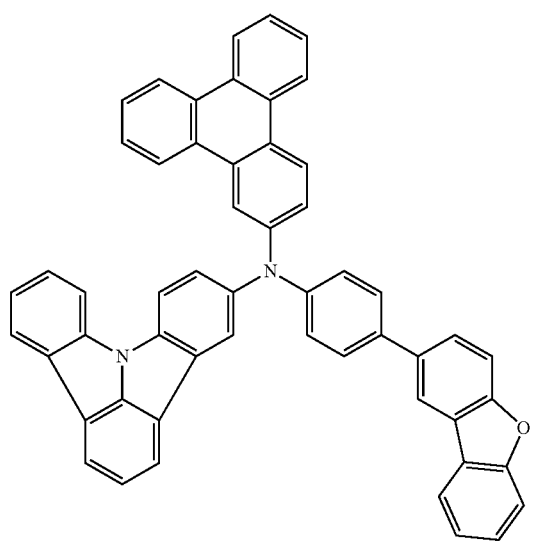
92
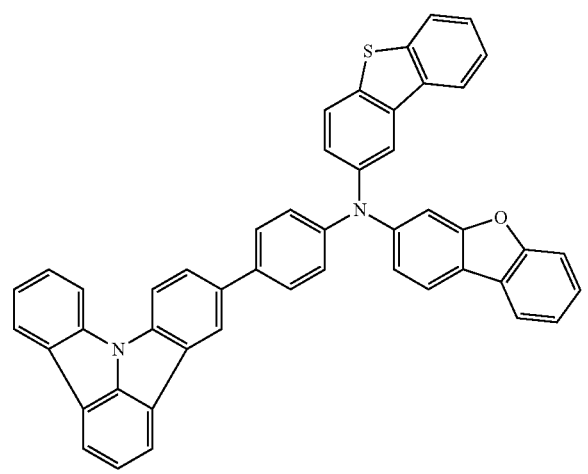
90
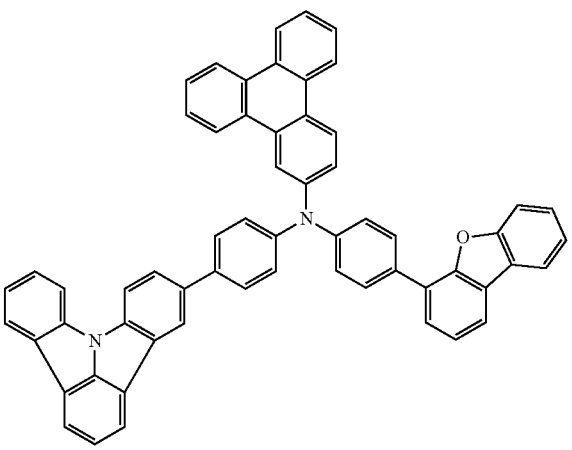
93
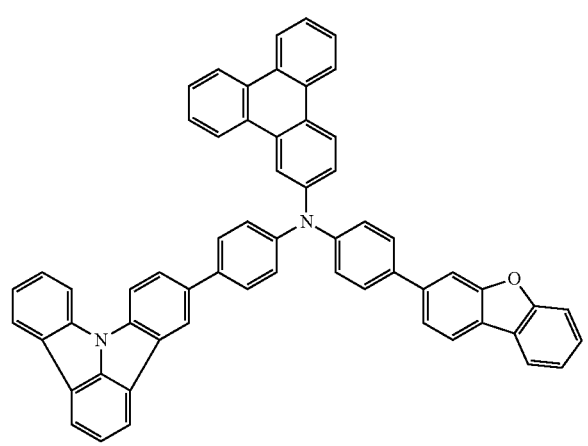
91
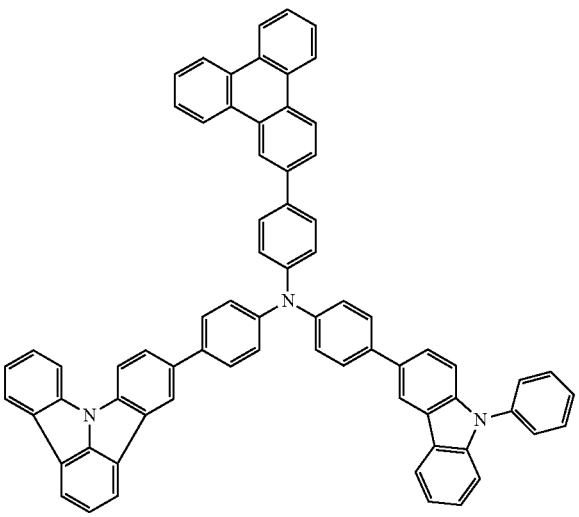
94
The material for an organic EL device according to an example embodiment may include one or more compounds having the following structures.

95
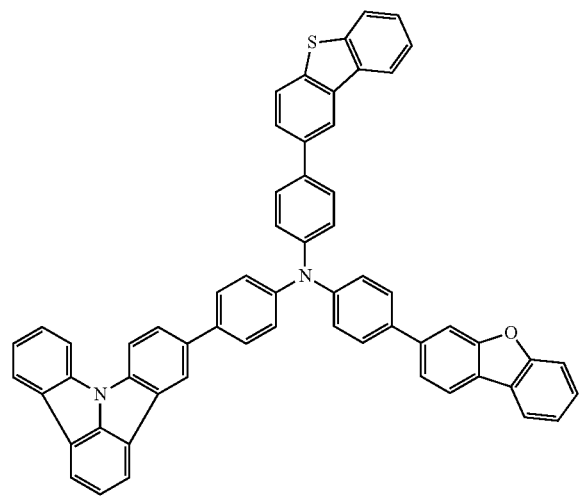
96
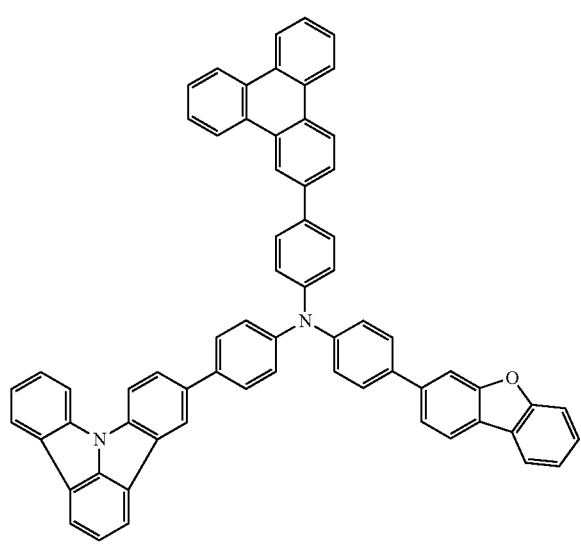
97
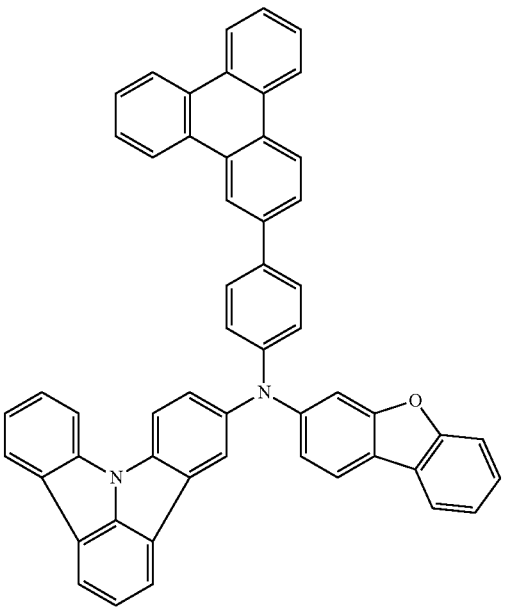
98
The material for an organic EL device according to an example embodiment may include one or more compounds having the following structures.

[Formula 15]
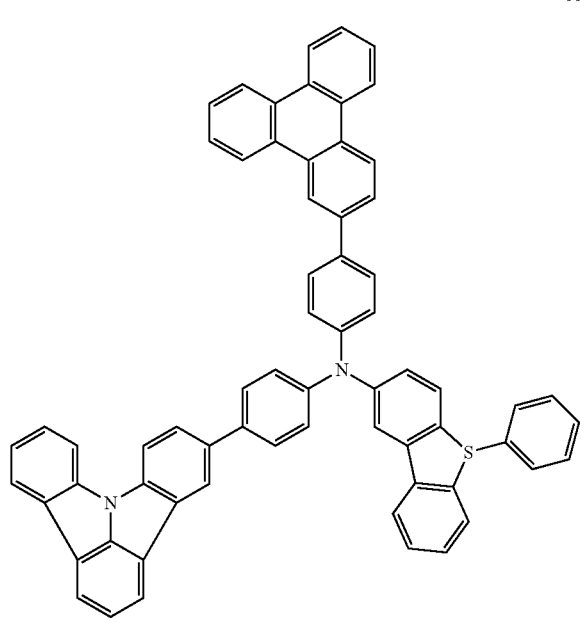
99
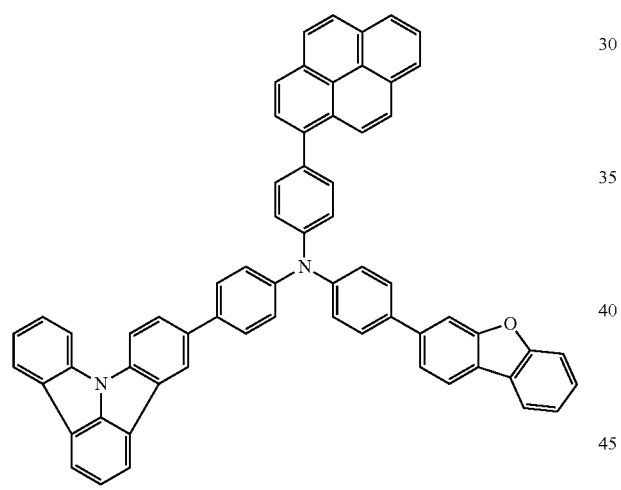
100
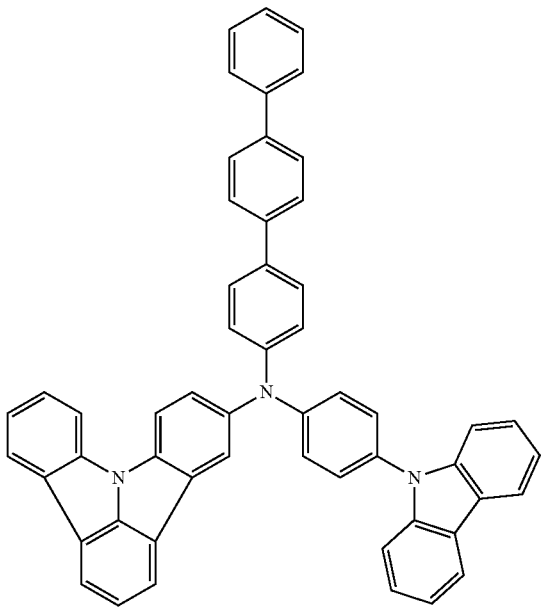
102
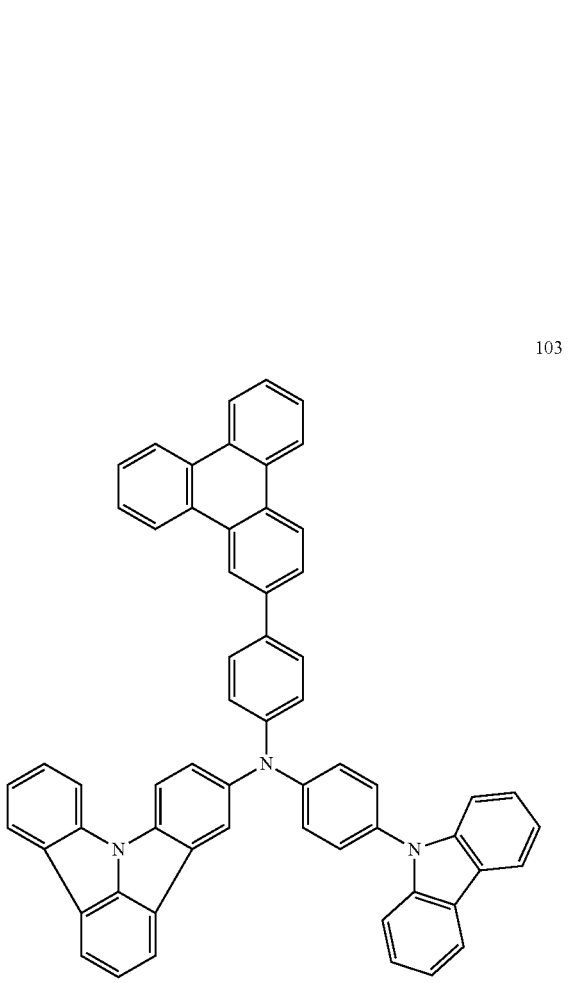
101
103

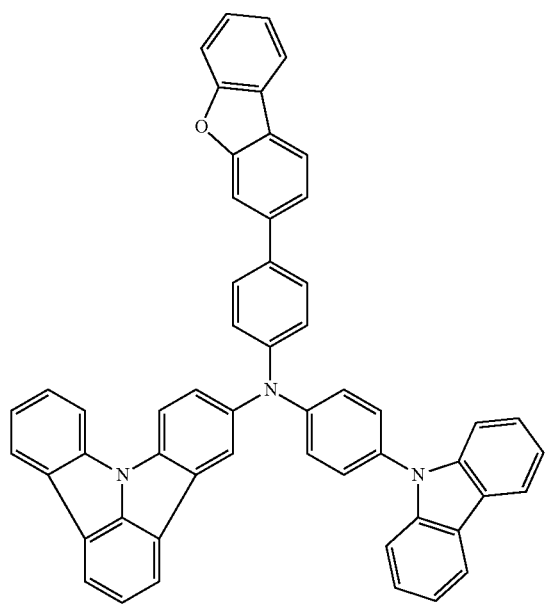
104
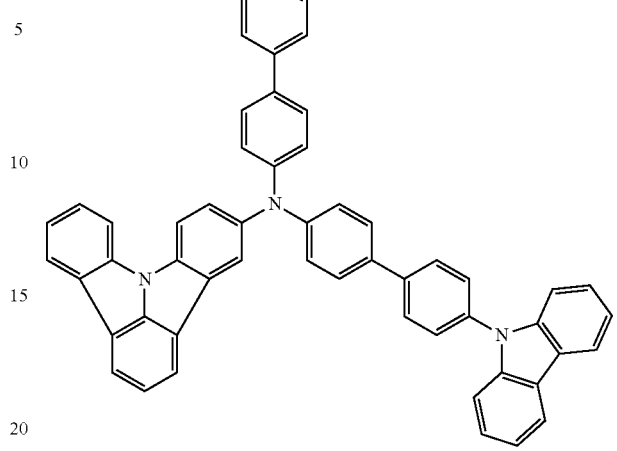
106
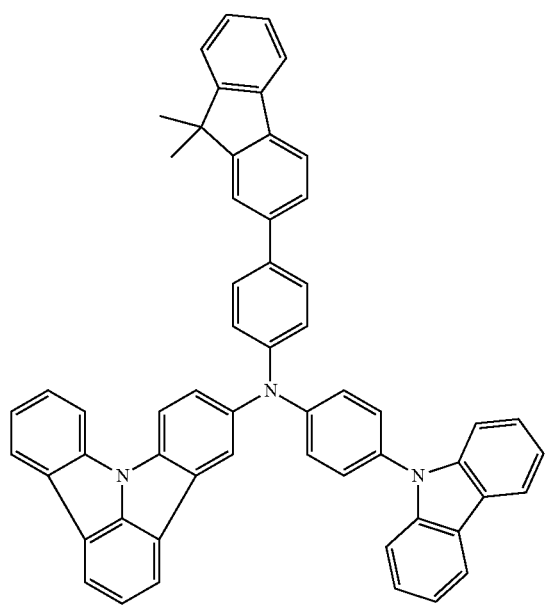
105
107
The material for an organic EL device according to an example embodiment may include one or more compounds having the following structures.

[Formula 16]
108
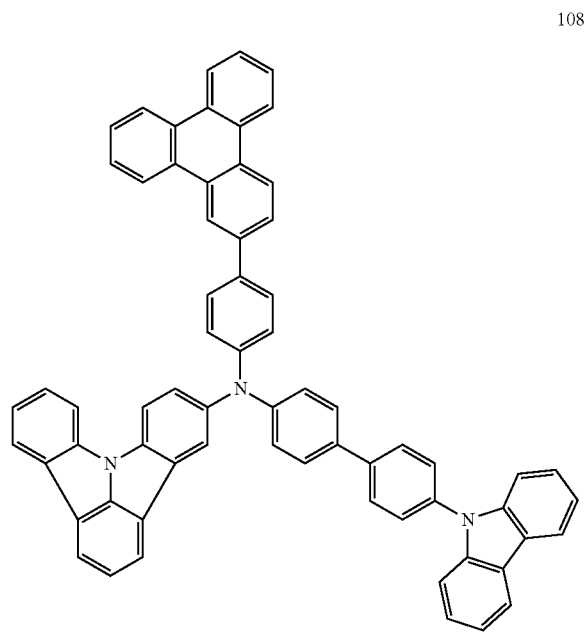 [SMILES: c1ccc(-c2ccc(-c3ccc(N(c4ccc(-c5ccc(-n6c7ccccc7c7ccccc76)cc5)cc4)c4ccc5c(c4)c4cccc6c7ccccc7n5c64)cc3)cc2)cc1]
109
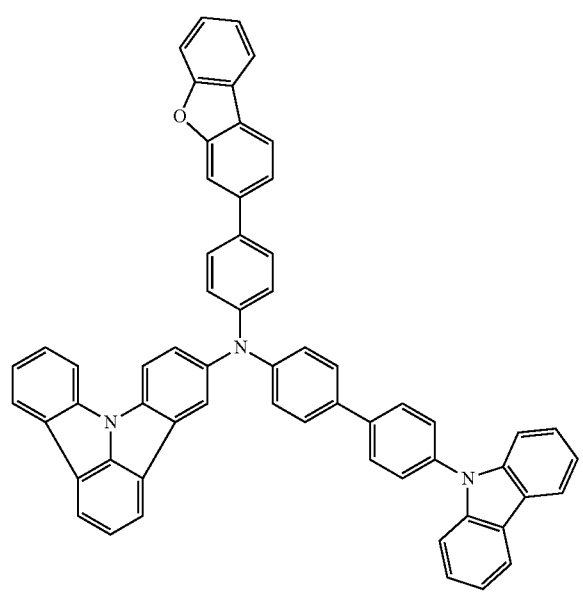
110
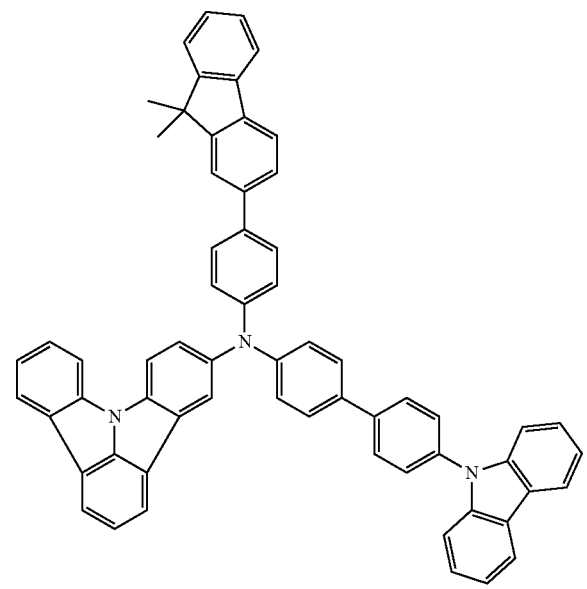
111

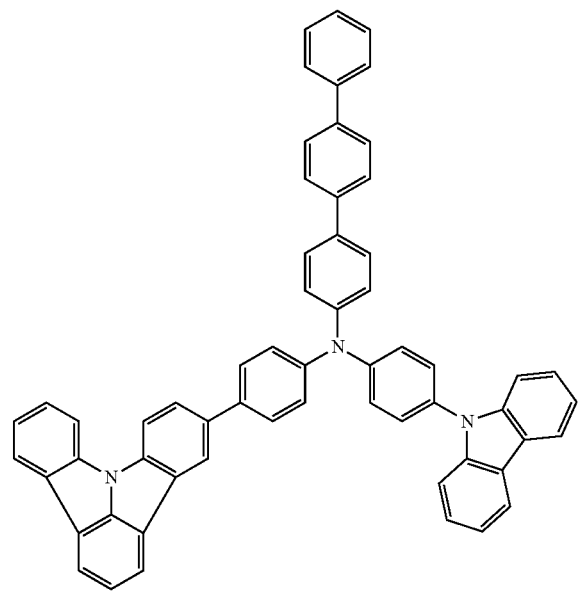
112
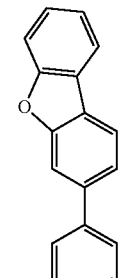
114
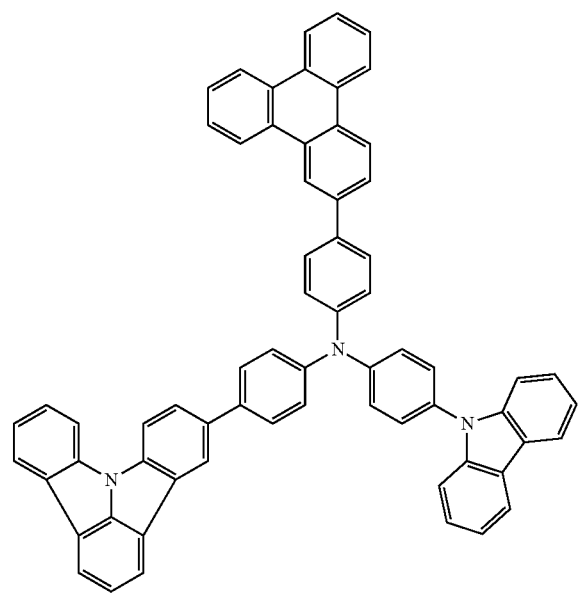
113
115
The material for an organic EL device according to an example embodiment may include one or more compounds having the following structures.

[Formula 17]
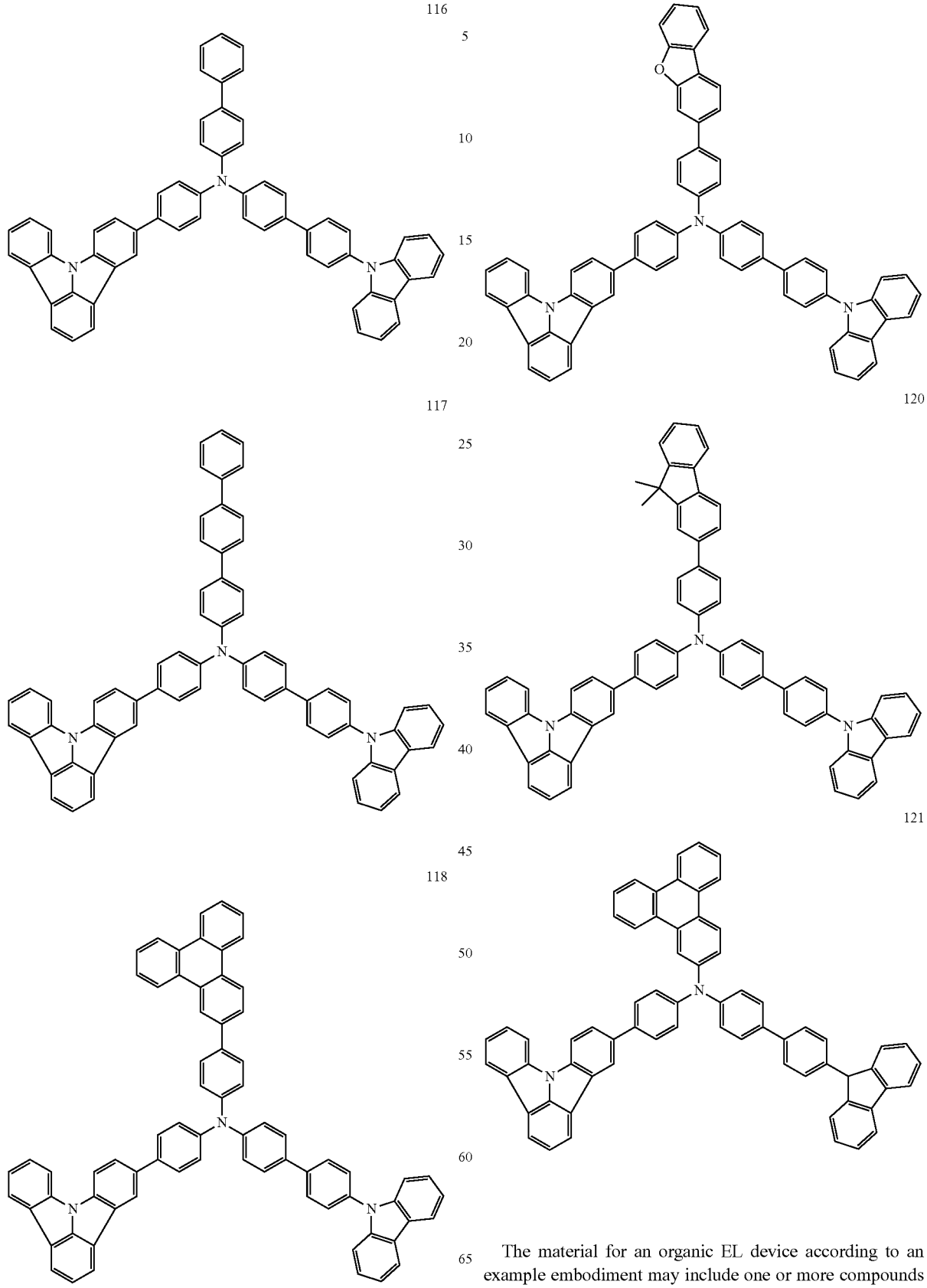
The material for an organic EL device according to an example embodiment may include one or more compounds having the following structures.

[Formula 18]
122
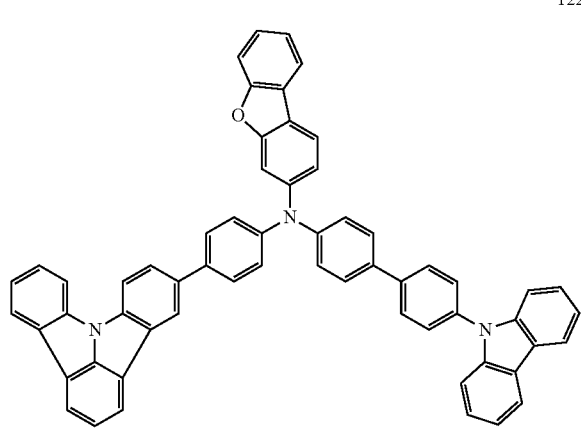
123
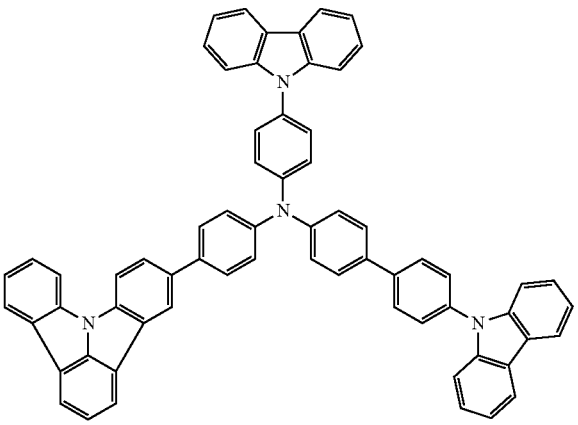
125
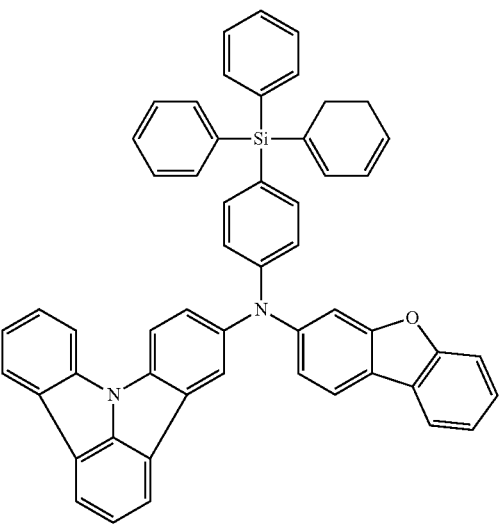
126
124
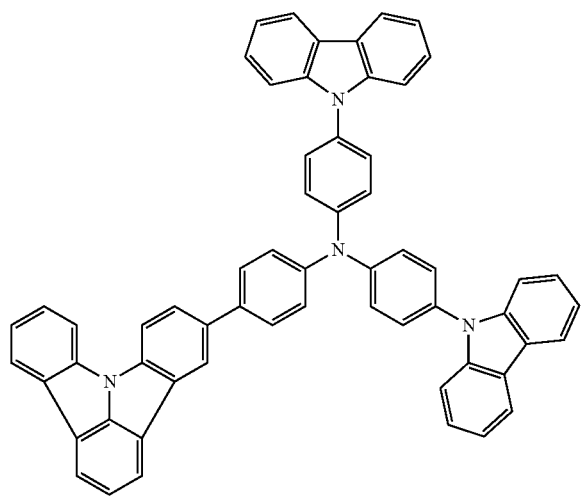
127
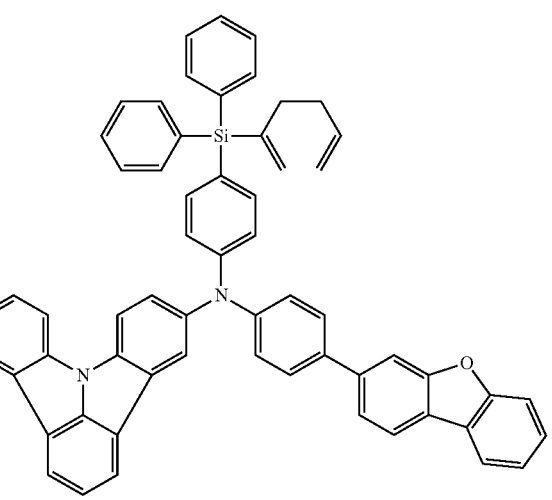

128
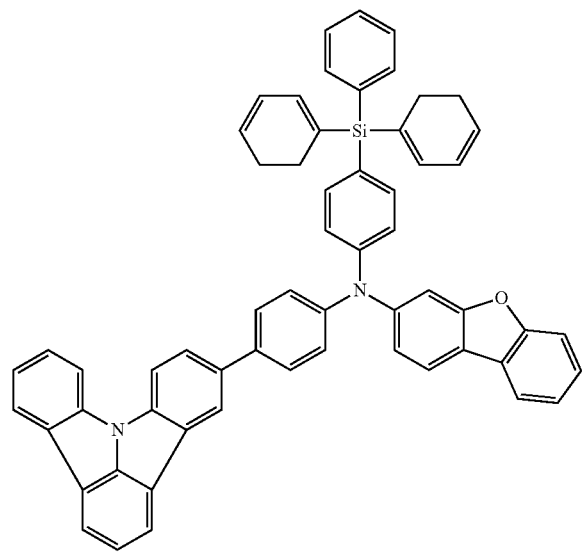
130
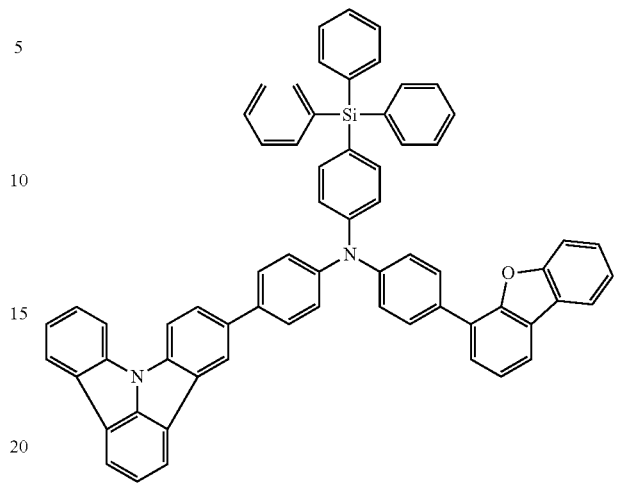
The material for an organic EL device according to an example embodiment may include one or more compounds having the following structures.
[Formula 19]
129
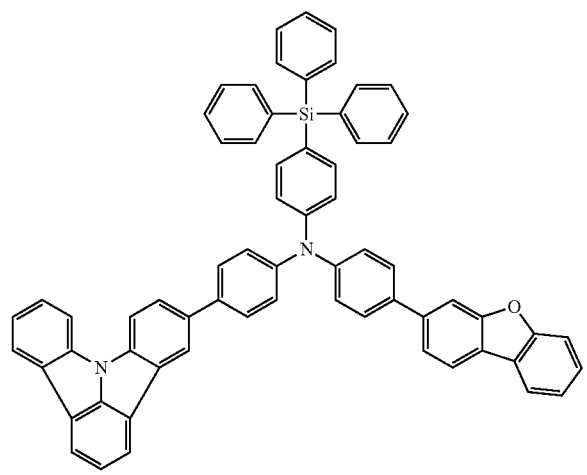
131
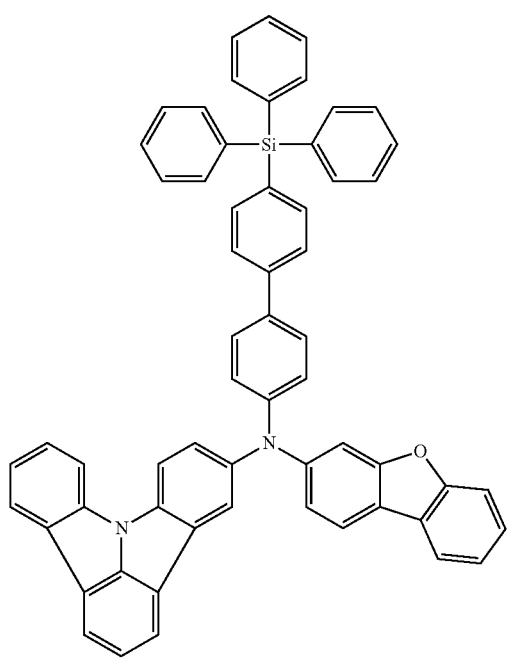

132
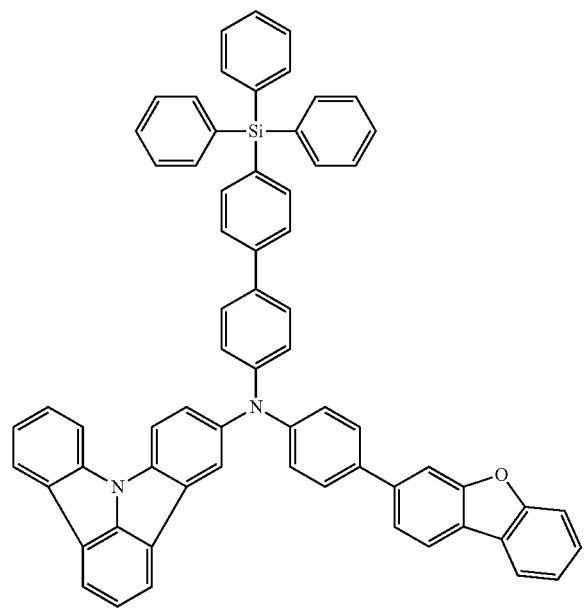
133
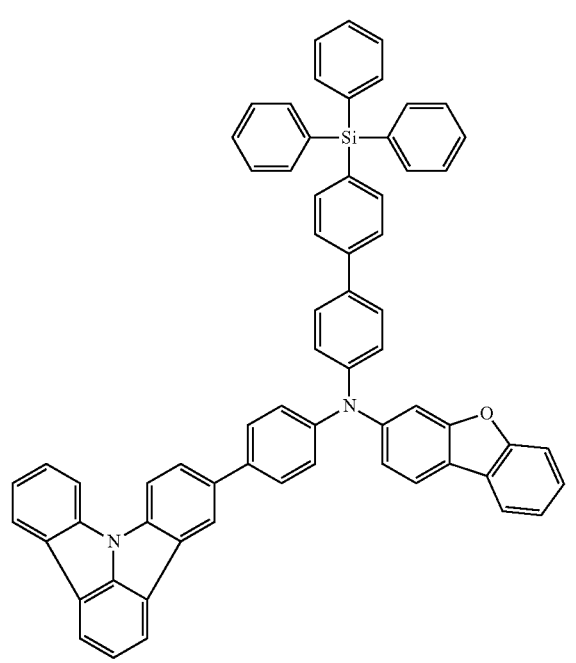
134
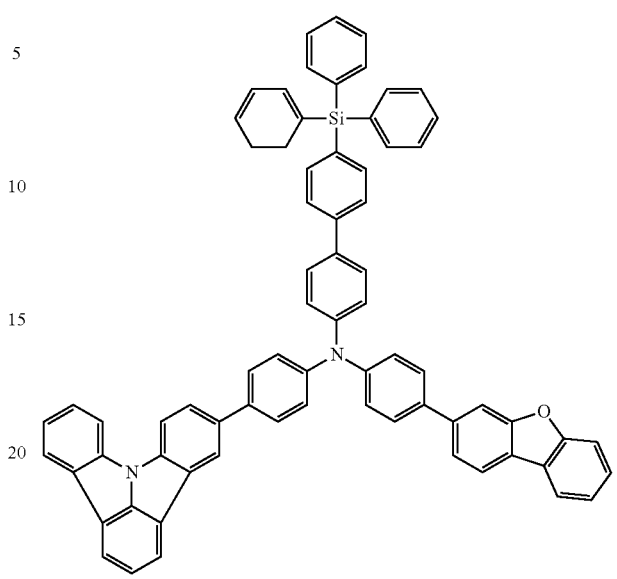
135
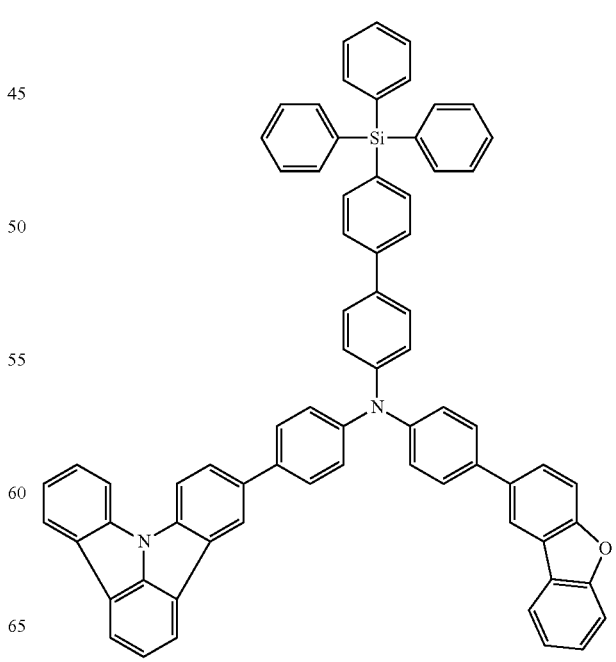

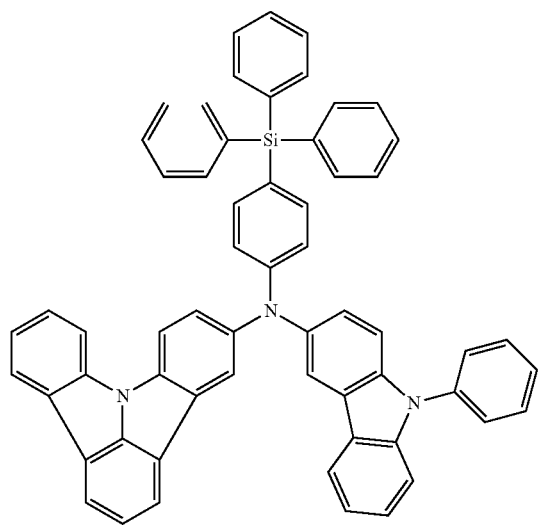
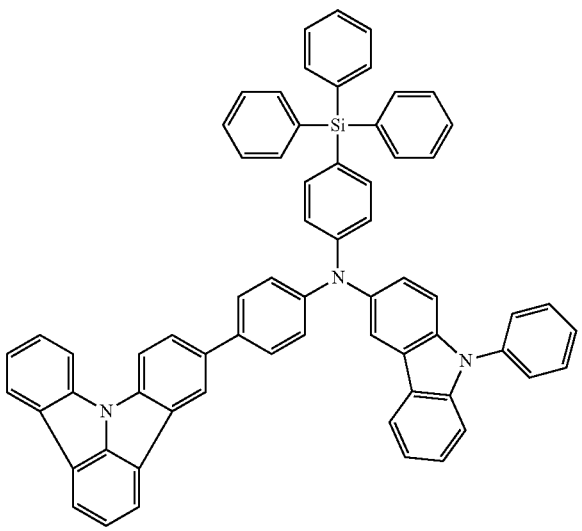
The material for an organic EL device according to an example embodiment may include one or more compounds having the following structures.
[Formula 10]
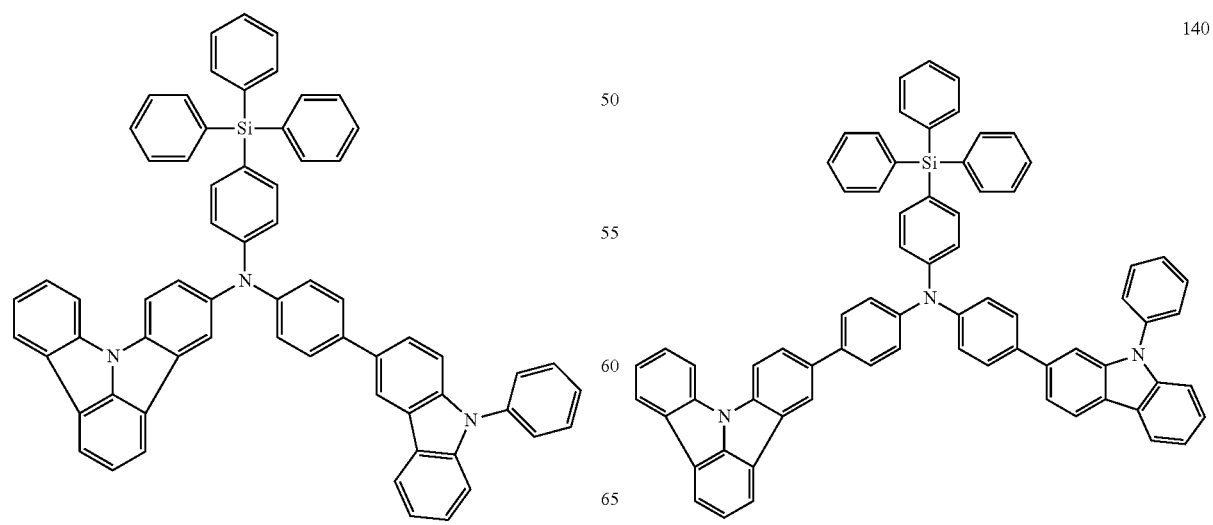

141
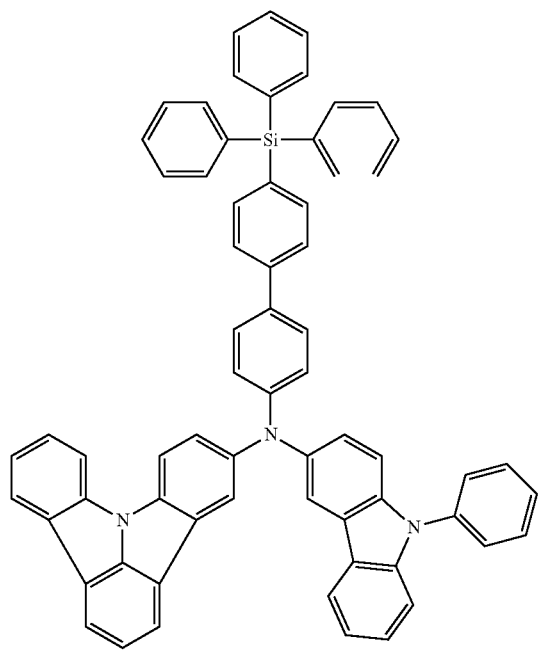
142
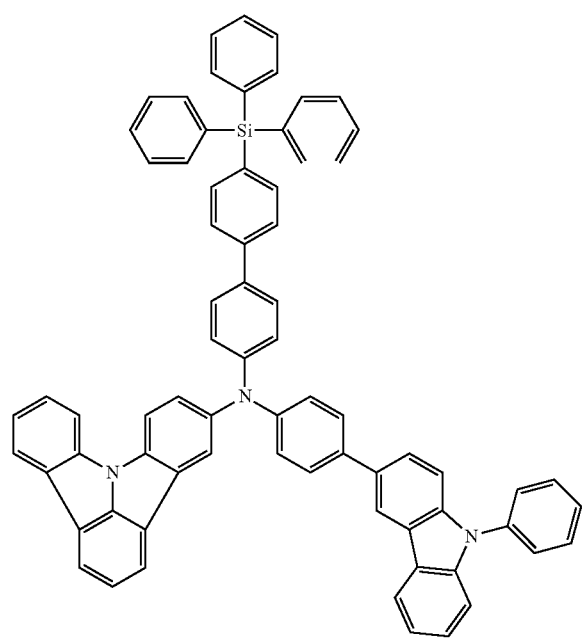
143
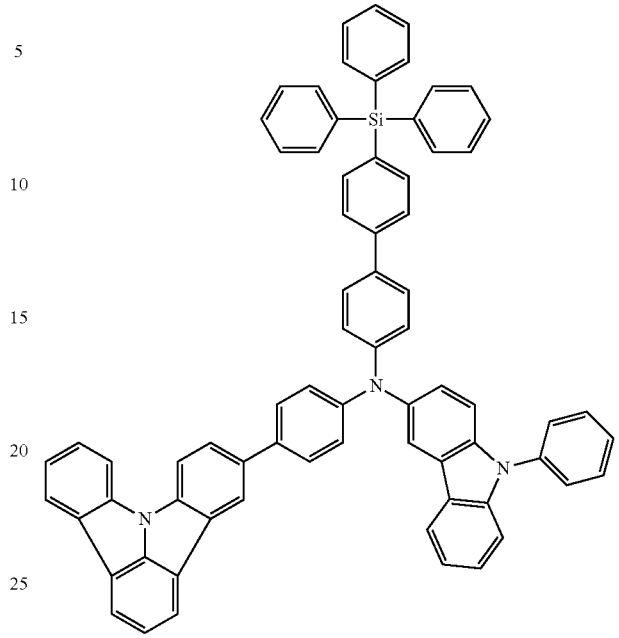
144
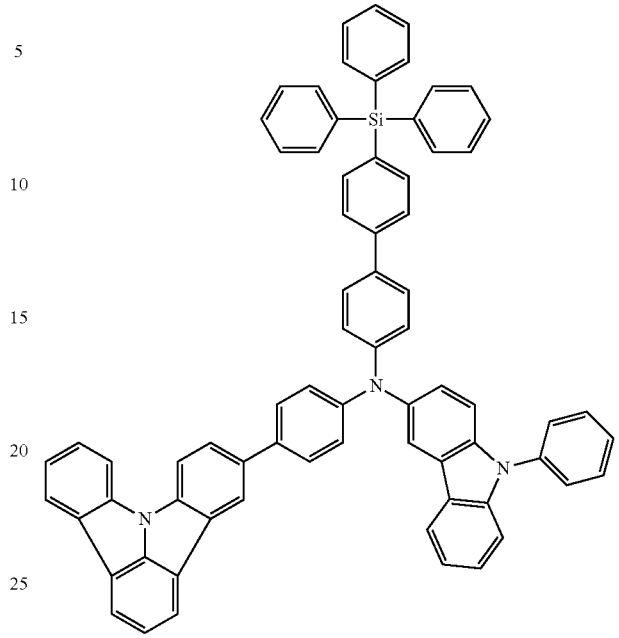
The material for an organic EL device according to an example embodiment may include one or more compounds having the following structures.

[Formula 11]
145
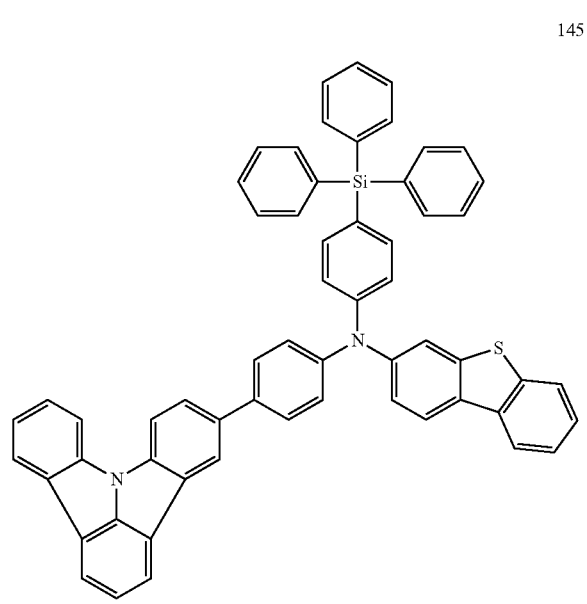 [SMILES: C1=CCCC([Si](C2=CC=CCC2)(c2ccccc2)c2ccc(N(c3ccc(-c4ccc5c(c4)c4cccc6c7ccccc7n5c64)cc3)c3ccc4c(c3)oc3ccccc34)cc2)=C1]
147
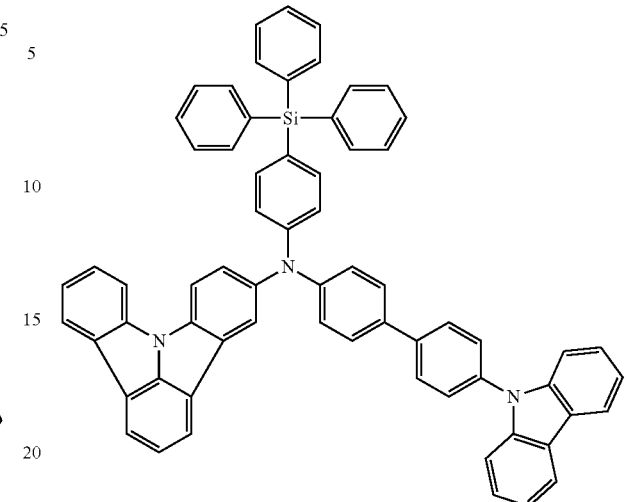
148
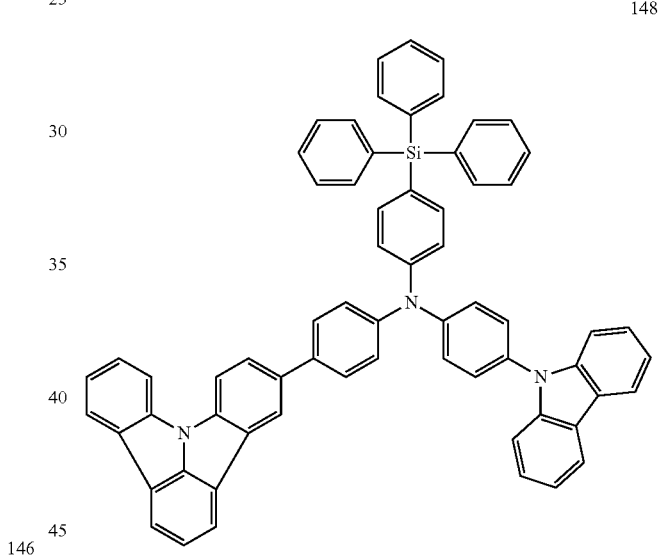
146
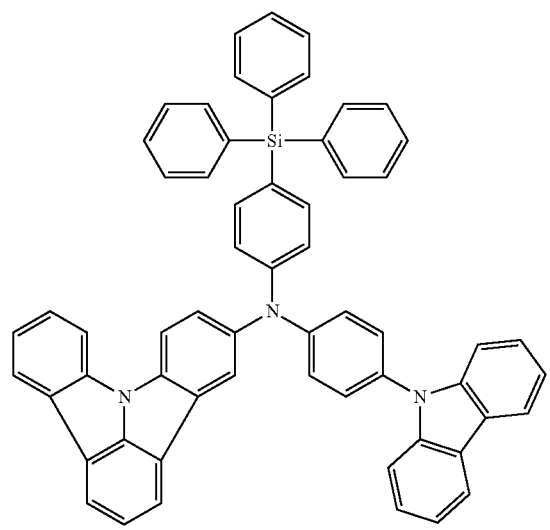
149
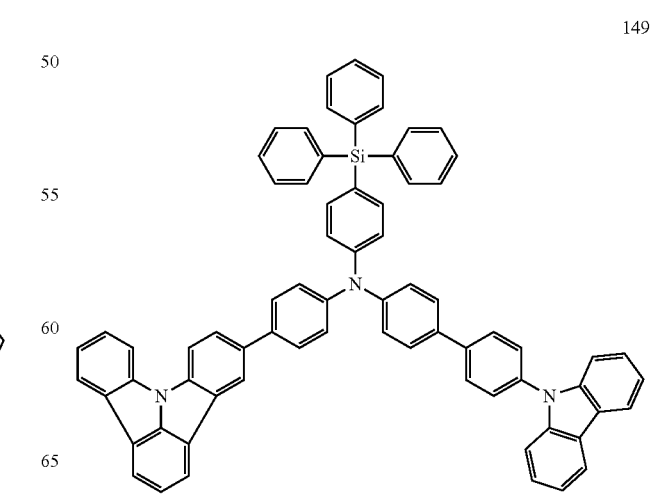

150
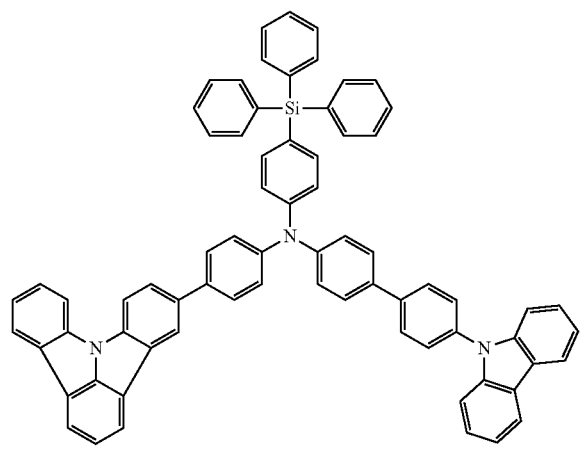
151
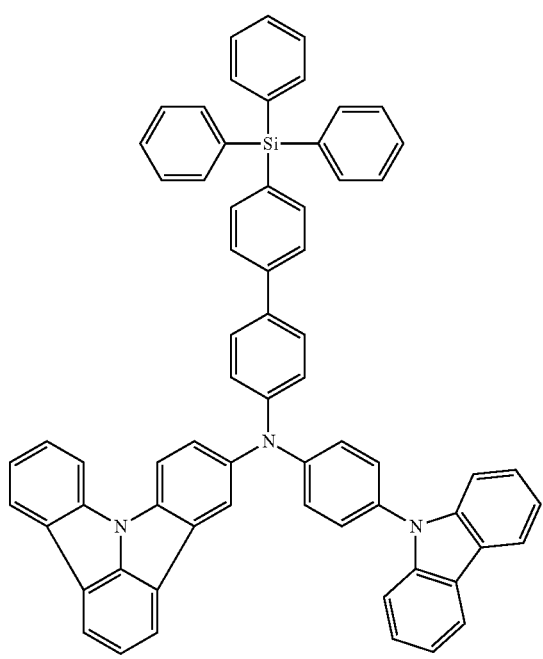
152
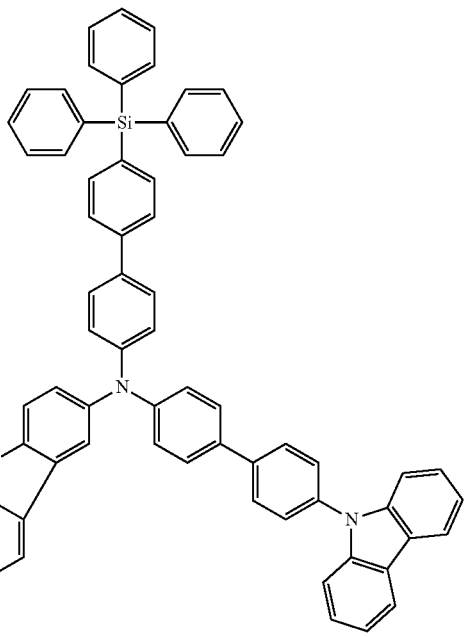
The material for an organic EL device according to an example embodiment may include one or more compounds having the following structures.

[Formula 12]
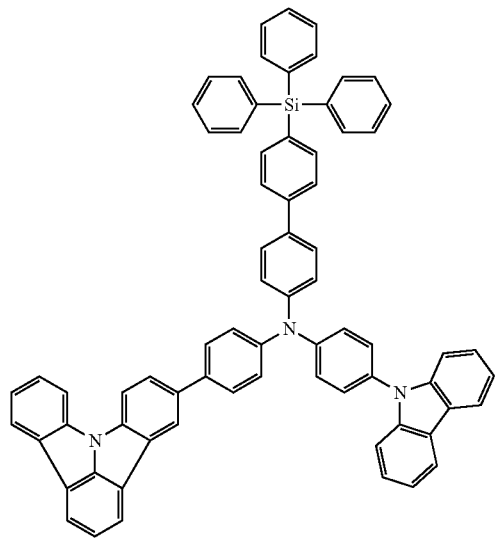
153
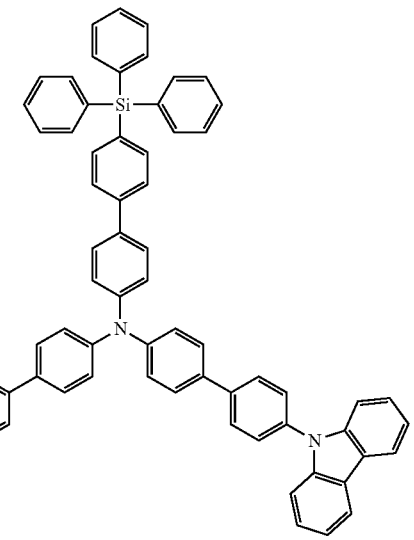
154
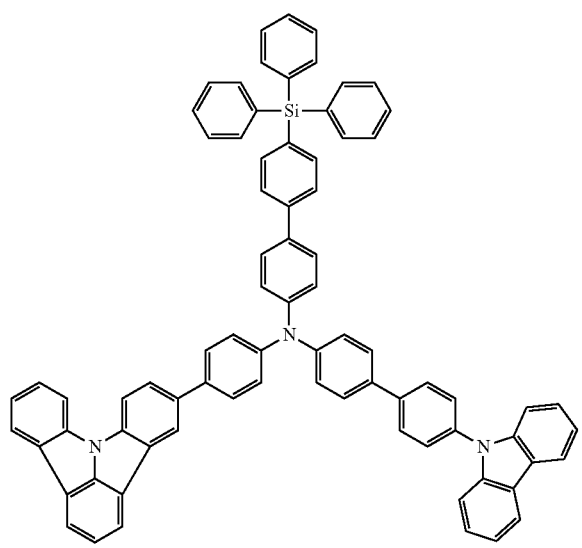
155
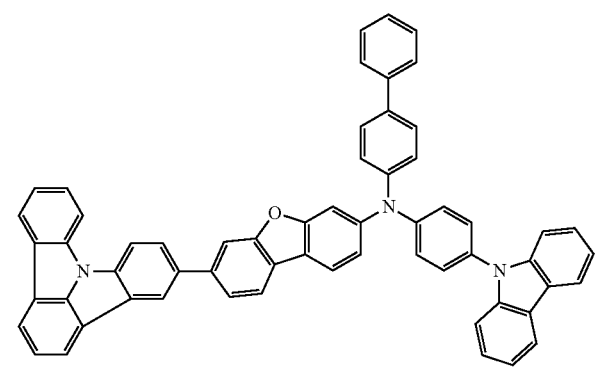
156
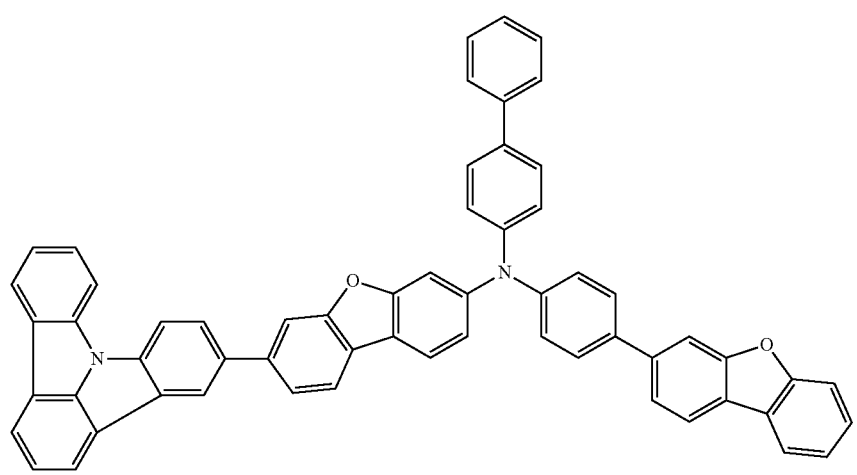
157

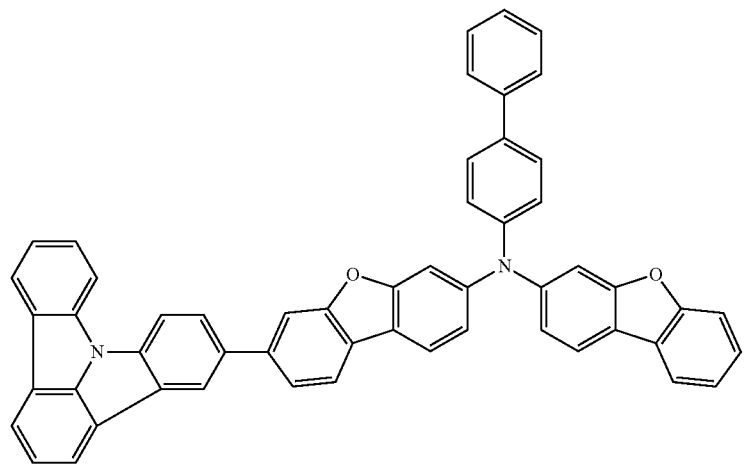
158
The material for an organic EL device according to an example embodiment may include one or more compounds having the following structures.
[Formula 13]
159

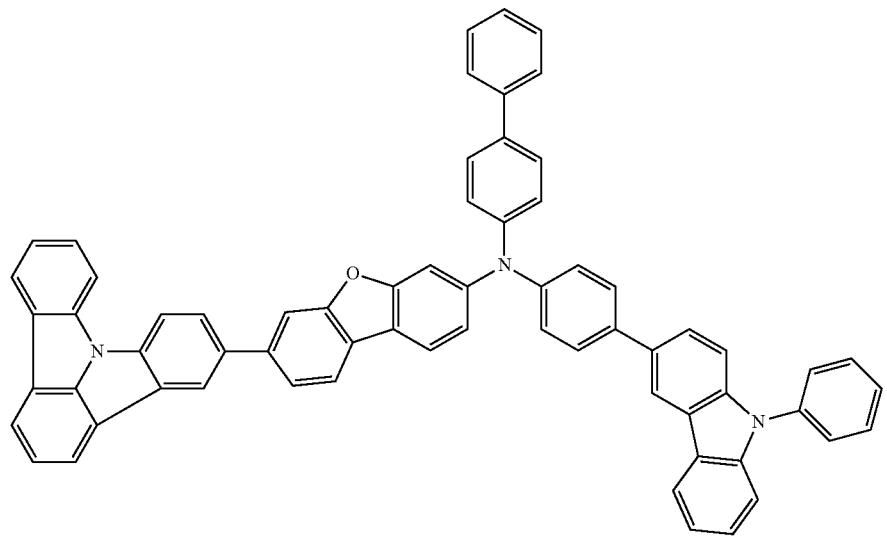
160
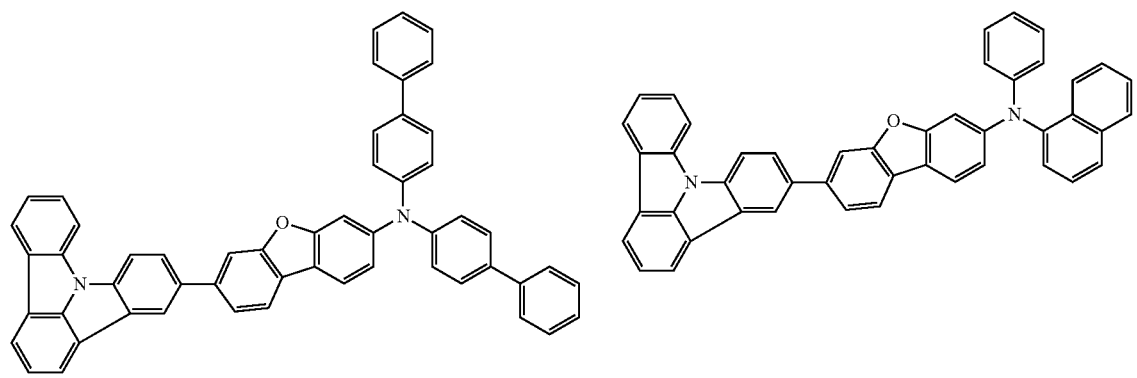
161
162
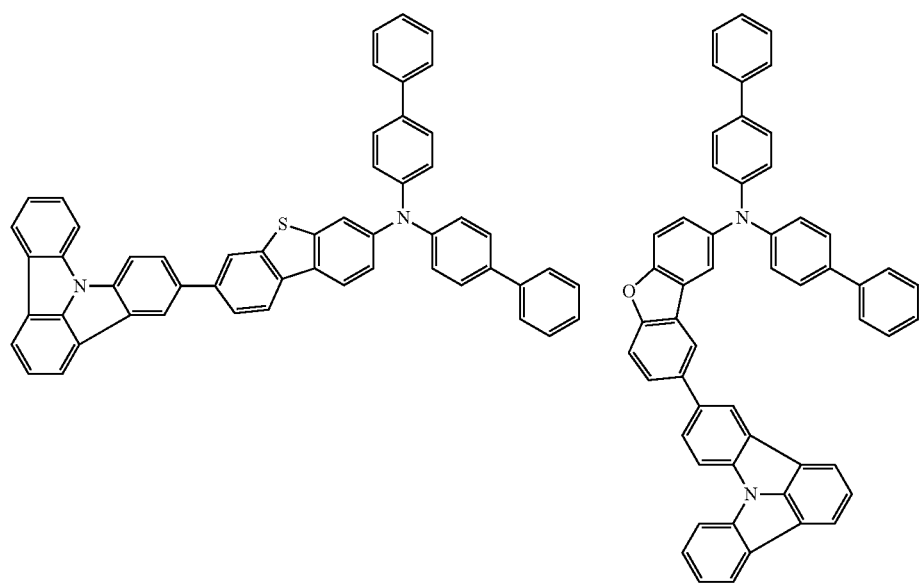
163
164
The material for an organic EL device according to an example embodiment may include one or more compounds having the following structures.

[Formula 14]
165
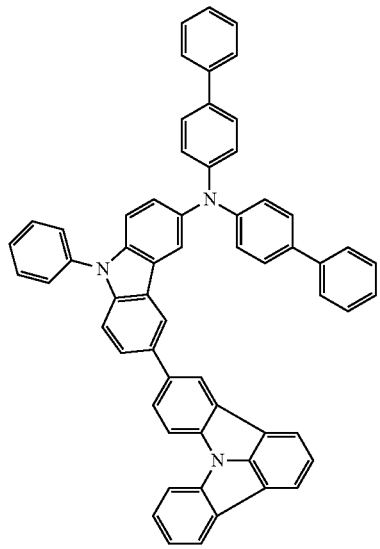
166
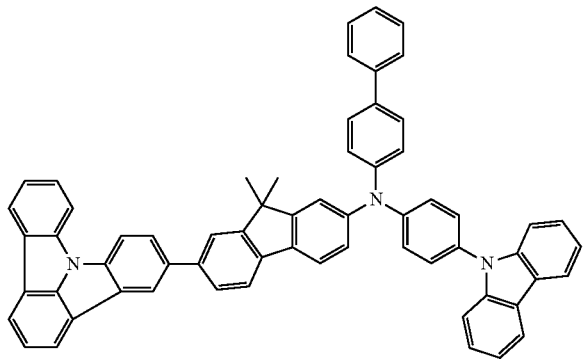
167
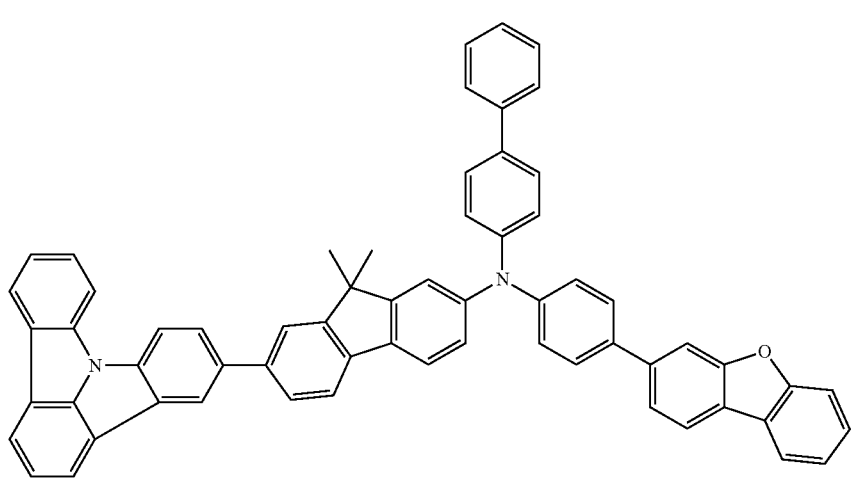
168
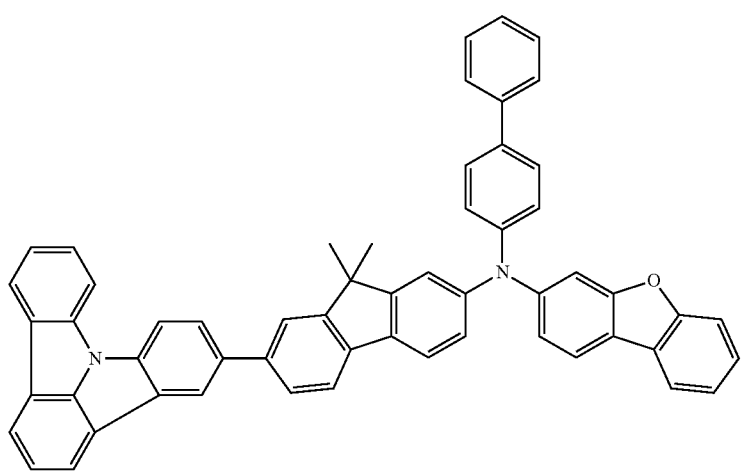

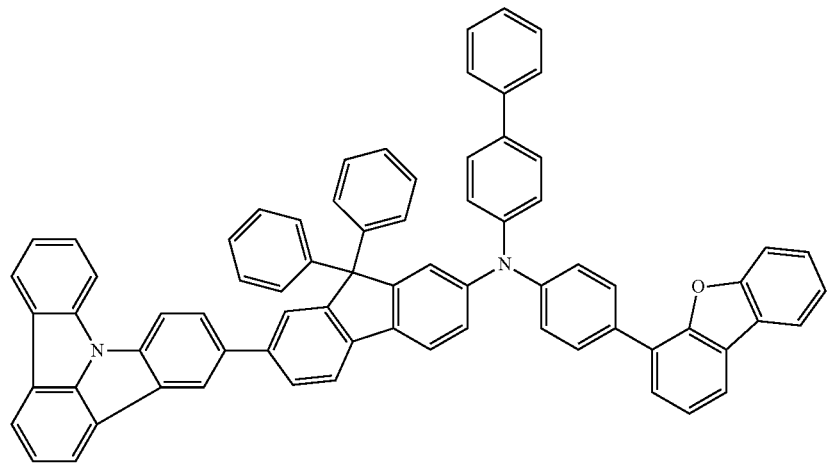

169

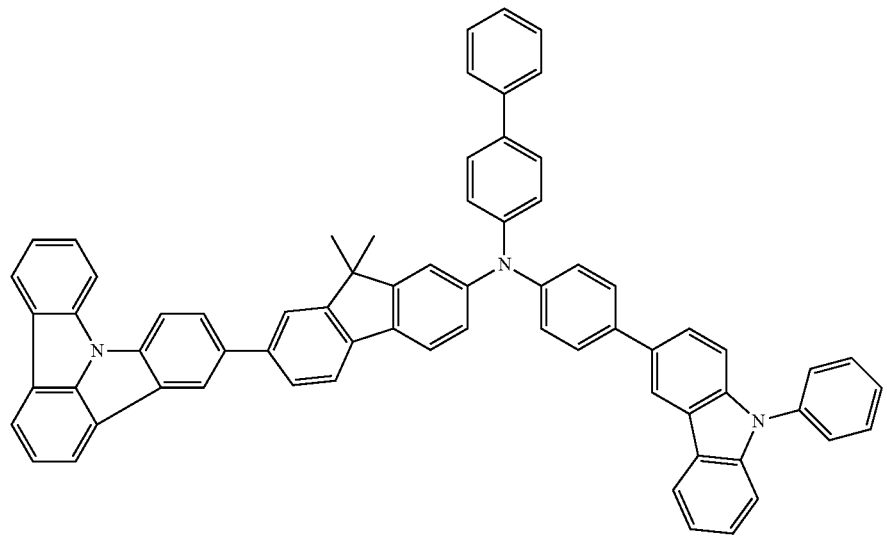

170

The material for an organic EL device according to an example embodiment may be used in a layer, for example, a layer among a stack of layers, disposed between an anode and an emission layer. For example, the material may be used as a hole transport material for an organic EL device. Using the material for an organic EL device according to an example embodiment for the formation of the hole transport layer may provide an organic EL device that may be driven at a low voltage and have high efficiency and long life.

The material for an organic EL device according to an example embodiment may be used for the hole transport material or a material of another layer. For example, the material for an organic EL device according to an example embodiment may be used as a material of a hole injection layer.

In the case that the material for an organic EL device according to an example embodiment is used as the material for the hole injection layer, the deterioration of the hole injection layer due to electrons may be restrained, which may help realize a long life of an organic EL device as in the case of using the material for the hole transport layer. In addition, a diamine derivative according to an example embodiment may have electron tolerance. Thus, the material may be used as a host material of an emission layer.

(Organic EL Device)

An organic EL device using the material for an organic EL device according to an example embodiment will be explained in connection with FIG. 1.

FIG. 1 is a schematic diagram illustrating a configuration of an organic EL device 100 according to an example embodiment.

According to the present example embodiment, the organic EL device 100 may include, for example, a substrate 102, an anode 104, a hole injection layer 106, a hole transport layer 108, an emission layer 110, an electron transport layer 112, an electron injection layer 114, and a cathode 116. In an embodiment, the material for an organic EL device according to an example embodiment may be used in the hole transport layer.

For example, an embodiment using the material for an organic EL device according to an example embodiment in the hole transport layer 108 will be explained. The substrate 102 may be, for example, a transparent glass substrate, a semiconductor substrate formed by using silicon, etc., or a flexible substrate of a resin, etc. The anode 104 is disposed on the substrate 102 and may be formed using, for example, indium tin oxide (ITO), indium zinc oxide (IZO), etc. The hole injection layer 106 is disposed on the anode 104 and may include, for example, 4,4',4''-tris[2-naphthyl)(phenyl)amino]

triphenylamine (2-TNATA) or N,N,N',N'-tetrakis(3-methylphenyl)-3,3'-dimethylbenzidine (HMTPD), etc. The hole transport layer 108 is disposed on the hole injection layer 106 and may be formed using the material for an organic EL device according to an example embodiment. The emission layer 110 is disposed on the hole transport layer 108 and may be formed using the material for an organic EL device according to an example embodiment. In another embodiment, the emission layer 110 may be formed using, for example, a host material including 9,10-di(2-naphthyl)anthracene (ADN) doped with 2,5,8,11-tetra-t-butylperylene (TBP). The electron transport layer 112 is disposed on the emission layer 110 and may be formed using, for example, a material including tris(8-hydroxyquinolinato)aluminum (Alq$_3$). The electron injection layer 114 is disposed on the electron transport layer 112 and may be formed using, for example, a material including lithium fluoride (LiF). The cathode 116 is disposed on the electron injection layer 114 and may be formed using, for example, a metal such as Al, or a transparent material such as ITO, IZO, etc. The above-described thin layers may be formed by selecting an appropriate layer forming method such as vacuum deposition, sputtering, various coatings, etc.

In the organic EL device 100 according to the present example embodiment, a hole transport layer driven at a low voltage and having high efficiency and long life may be formed by using the material for an organic EL device according to an example embodiment. In addition, the material for an organic EL device according to an example embodiment may be applied in an organic EL apparatus of an active matrix using thin film transistors (TFT).

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

(Preparation Method)

The material for an organic EL device according to an example embodiment may be synthesized, for example, by the following method.

(Synthesis of Compound 16 in Formula 15)

[Formula 15]

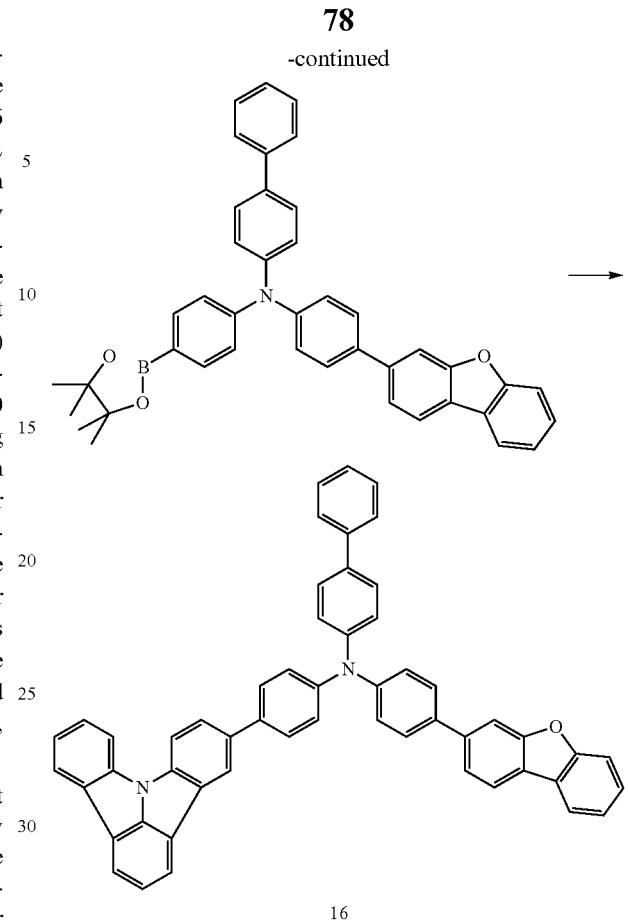

An amine compound (3 mmol), an indolocarbazole compound (3 mmol), a palladium catalyst (0.3 mol), a phosphine ligand (1.2 mol), an alkaline reagent (12 mmol), toluene (200 mL), water (20 mL) and ethanol (10 mL) were added in a reaction vessel, followed by charging nitrogen in the vessel and stirring while refluxing for 20 hours. After cooling, water was added in the reactant, and an organic layer was extracted. The organic layer thus obtained was dried with magnesium sulfate and filtered, and the filtrate thus obtained was concentrated using a rotary evaporator. The crude product thus obtained was separated by silica gel column chromatography, and the solid thus obtained was recrystallized to produce Compound 16 in the above Formula 15 with yield of 60% (APCI+: $C_{54}H_{34}N_2O$, measured value 726).

(Synthesis of Compound 116 of Formula 16)

[Formula 16]

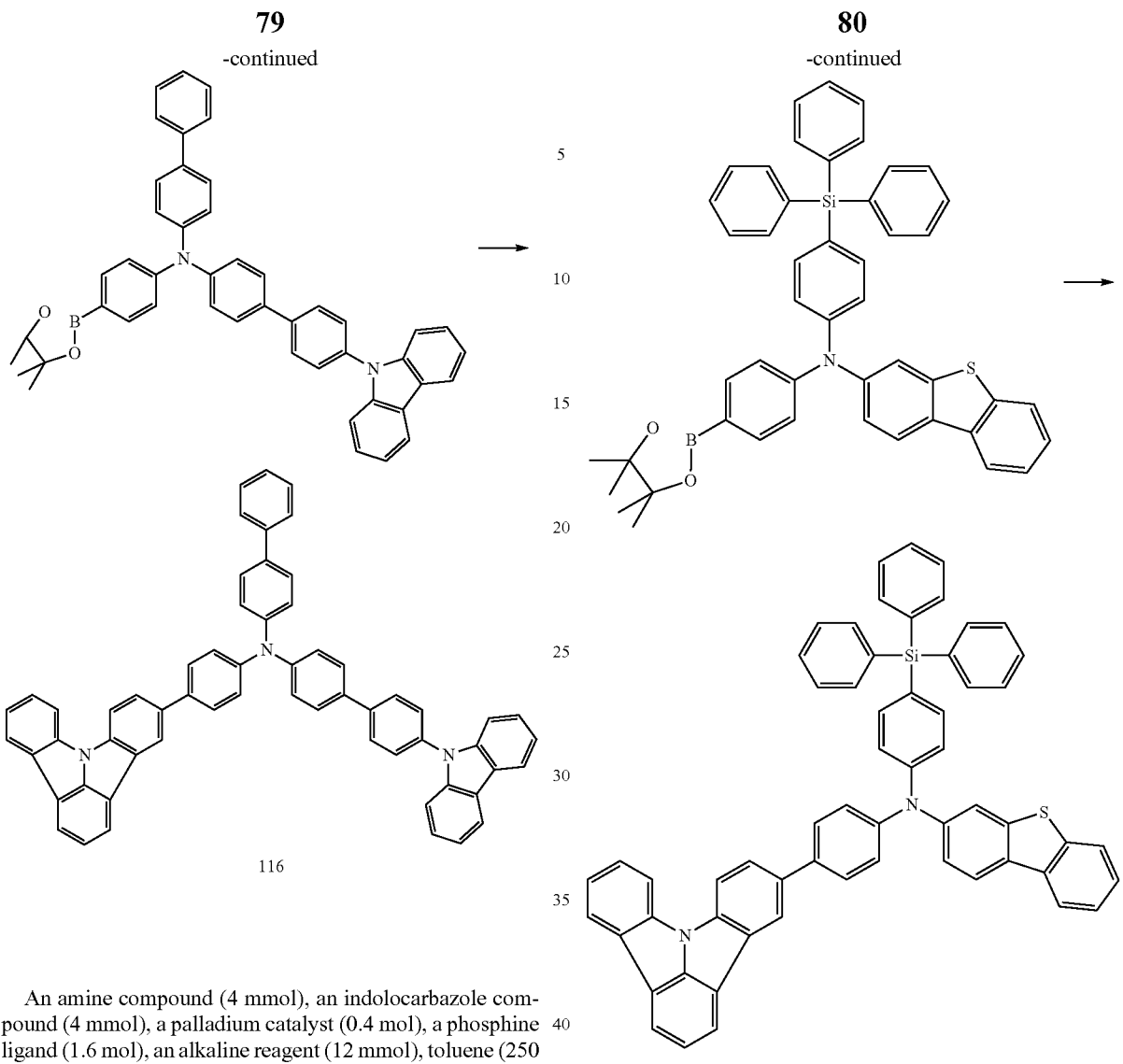

116

An amine compound (4 mmol), an indolocarbazole compound (4 mmol), a palladium catalyst (0.4 mol), a phosphine ligand (1.6 mol), an alkaline reagent (12 mmol), toluene (250 mL), water (25 mL) and ethanol (13 mL) were added in a reaction vessel, followed by charging nitrogen in the vessel and stirring while refluxing for 18 hours. After cooling, water was added in the reactant, and an organic layer was extracted. The organic layer thus obtained was dried with magnesium sulfate and filtered, and the filtrate thus obtained was concentrated using a rotary evaporator. The crude product thus obtained was separated by silica gel column chromatography, and the solid thus obtained was recrystallized to produce Compound 116 in the above Formula 16 with yield of 43% (APCI+: $C_{60}H_{39}N_3$, measured value 801).

(Synthesis of Compound 145 of Formula 17)

[Formula 17]

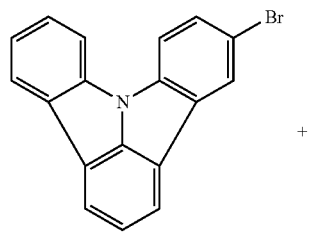

+

145

An amine compound (4.5 mmol), an indolocarbazole compound (4.5 mmol), a palladium catalyst (0.5 mol), a phosphine ligand (2.0 mol), an alkaline reagent (18 mmol), toluene (300 mL), water (30 mL) and ethanol (15 mL) were added in a reaction vessel, followed by charging nitrogen in the vessel and stirring while refluxing for 22 hours. After cooling, water was added in the reactant, and an organic layer was extracted. The organic layer thus obtained was dried with magnesium sulfate and filtered, and the filtrate thus obtained was concentrated using a rotary evaporator. The crude product thus obtained was separated by silica gel column chromatography, and the solid thus obtained was recrystallized to produce Compound 145 in the above Formula 17 with yield of 50% (APCI+: $C_{60}H_{40}N_2SSi$, measured value 848).

(Synthesis of Compound 163 of Formula 18)

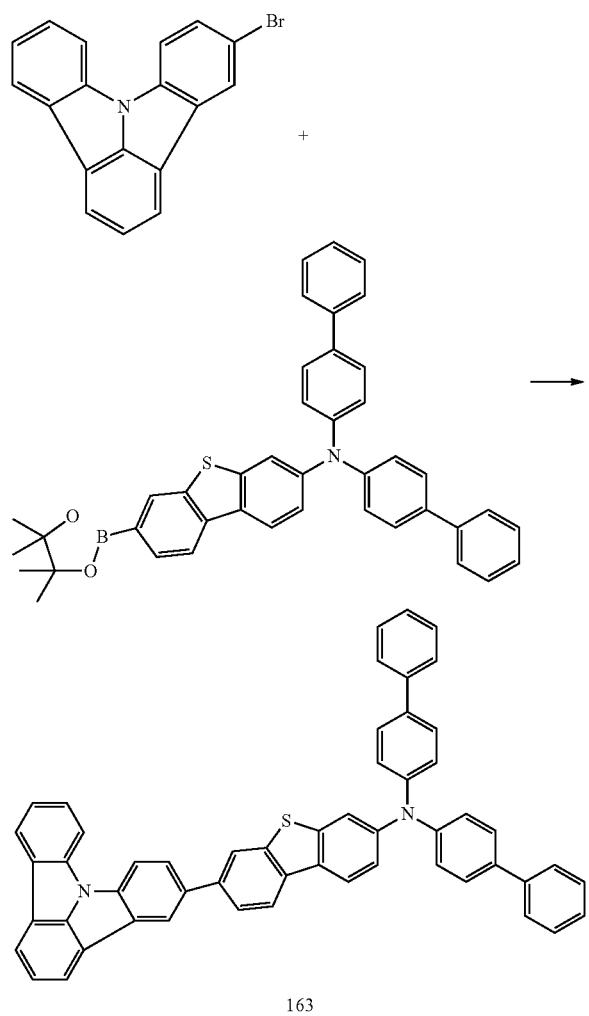

An amine compound (2.5 mmol), an indolocarbazole compound (2.5 mmol), a palladium catalyst (0.3 mol), a phosphine ligand (1.2 mol), an alkaline reagent (10 mmol), toluene (250 mL), water (25 mL) and ethanol (13 mL) were added in a reaction vessel, followed by charging nitrogen in the vessel and stirring while refluxing for 19 hours. After cooling, water was added in the reactant, and an organic layer was extracted. The organic layer thus obtained was dried with magnesium sulfate and filtered, and the filtrate thus obtained was concentrated using a rotary evaporator. The crude product thus obtained was separated by silica gel column chromatography, and the solid thus obtained was recrystallized to produce Compound 163 in the above Formula 18 with yield of 61% (APCI+: $C_{54}H_{34}N_2S$, measured value 742).

Organic EL devices according to Examples 1 to 4 were manufactured using the above Compounds 16, 116, 145, and 163 in hole transport materials. In addition, organic EL devices according to Comparative Examples 1 and 2 were manufactured using the following Comparative Compounds 1 and 2 in hole transport materials for comparison.

In detail, the substrate 102 was formed by using a transparent glass substrate, the anode 104 was formed using ITO to a thickness of about 150 nm, the hole injection layer 106 having a thickness of about 60 nm was formed by using 2-TNATA, the hole transport layer 108 was formed, using materials including the respective compounds according to the Examples and the Comparative Examples, to a thickness of about 30 nm, the emission layer 110 was formed using ADN doped with 3% TBP to a thickness of about 25 nm, the electron transport layer 112 was formed using $Alq_3$ to a thickness of about 25 nm, the electron injection layer 114 was formed using LiF to a thickness of about 1 nm, and the cathode 116 was formed using Al to a thickness of about 100 nm.

With respect to the organic EL devices thus manufactured, the voltage, the emission efficiency, and the life were evaluated. The values were measured and evaluated at current density of 10 $mA/cm^2$ and half life of 1,000 $cd/m^2$.

TABLE 1

| | Voltage (V) | Emission efficiency (cd/A) | Life LT50 (hr) |
|---|---|---|---|
| Example 1 | 6.5 | 7.0 | 2,700 |
| Example 2 | 6.4 | 7.5 | 2,600 |
| Example 3 | 7.1 | 7.9 | 2,300 |
| Example 4 | 7.0 | 7.7 | 2,200 |

TABLE 1-continued

| | Voltage (V) | Emission efficiency (cd/A) | Life LT50 (hr) |
|---|---|---|---|
| Comparative Example 1 | 7.5 | 6.2 | 1,500 |
| Comparative Example 2 | 8.1 | 5.3 | 1,200 |

As shown in Table 1, organic EL devices formed with materials according to embodiments, which included an amine moiety combined at the position 5 of an indolo[3,2,1-jk]carbazolyl moiety, were driven at a lower voltage, and had improved emission efficiency and increased half life when compared to an organic EL device of Comparative Example 1 using an amine moiety having a carbazolyl group and an organic EL device of Comparative Example 2 using a diamine moiety combined with an aryl group.

By way of summation and review, an example of an organic electroluminescence device (hereinafter referred to as an organic EL device) is an organic EL device that includes an anode, a hole transport layer disposed on the anode, an emission layer disposed on the hole transport layer, an electron transport layer disposed on the emission layer, and a cathode disposed on the electron transport layer. Holes injected from the anode are injected into the emission layer via the hole transport layer. Meanwhile, electrons are injected from the cathode, and then injected into the emission layer via the electron transport layer. The holes and the electrons injected into the emission layer are recombined to generate excitons within the emission layer. The organic EL device emits light by using light generated by the radiation deactivation of the excitons. The organic EL device may have various configurations.

In application of the organic EL device in a display apparatus, driving at a low voltage, high efficiency, and long life of the organic EL device are desired, and the normalization, the stabilization and the durability of a hole transport layer have been studied to help realize the high efficiency and long life of the organic EL device. As a material used in a hole transport layer, various compounds such as an aromatic amine-based compound have been considered. For example, a carbazole derivative has been studied as a hole transport material or a hole injection material. In addition, an amine compound having a terphenyl group has been studied as a hole transport material and a host material in an emission layer. An amine compound having a fluorenyl group has been studied as a hole transport material or a hole injection material. However, organic EL devices using those materials may be difficult to form with high emission efficiency and emission life. An organic EL device having a low driving voltage, high efficiency, and long emission life is desired.

As described above, embodiments relate to a material for an organic electroluminescence device, which may be driven at a low voltage, and may have high efficiency and long life in, for example, a blue emission region and a green emission region, and an organic electroluminescence device using the same. Embodiments may provide a material for an organic EL device that helps realize driving at a low voltage, and high efficiency and long life, and an organic EL device using the same.

A hole transport layer in the organic EL device according to an example embodiment may be formed using a hole transport material that includes a compound having an amine moiety combined at position 5 of an indolo[3,2,1-jk]carbazolyl moiety with high electron tolerance greater than that of a carbazolyl group. An organic EL device driven manufactured using the material according to an embodiment may be driven at a low voltage, and may have high efficiency and long life. For example, the driving voltage of an organic EL device in a blue emission region and a green emission region may be restrained by using a material according to an embodiment that includes a compound having an amine moiety combined with an indolo[3,2,1-jk]carbazolyl moiety at the position 5.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A material for an electroluminescence (EL) device, the material including a compound represented by following Formula 1:

[Formula 1]

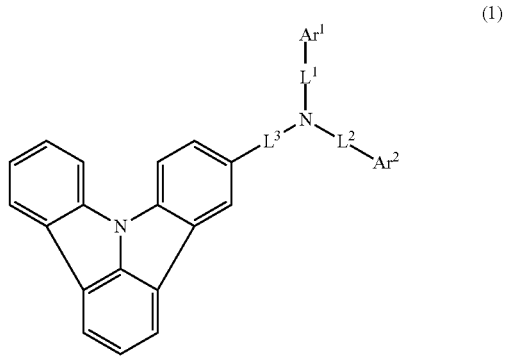

(1)

where $Ar^1$ and $Ar^2$ are independently a substituted or unsubstituted aryl group, or a substituted or unsubstituted heteroaryl group, $L^1$, $L^2$, and $L^3$ are independently a single bond, a substituted or unsubstituted aryl group, or a substituted or unsubstituted heteroaryl group, and at least one of $Ar^1$, $Ar^2$, $L^1$, $L^2$, and $L^3$ is a substituted or unsubstituted heteroaryl group.

2. The material as claimed in claim 1, wherein at least one of $Ar^1$ and $Ar^2$ is a substituted or unsubstituted heteroaryl group, and $L^1$, $L^2$, and $L^3$ are independently a single bond, a substituted or unsubstituted aryl group having 6 to 18 ring carbon atoms.

3. The material as claimed in claim 1, wherein $Ar^1$ and $Ar^2$ are independently a substituted or unsubstituted aryl group having 6 to 24 ring carbon atoms, a substituted or unsubstituted carbazolyl group, a substituted or unsubstituted dibenzofuryl group, or a substituted or unsubstituted dibenzothienyl group.

4. An organic electroluminescence (EL) device comprising a material that includes a compound represented by the following Formula 1:

[Formula 1]

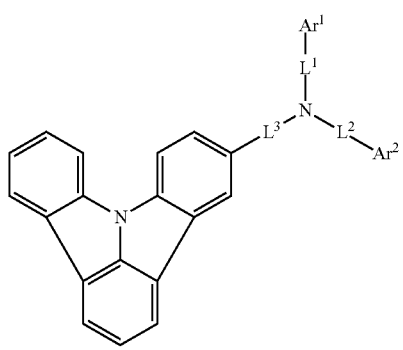

(1)

where Ar¹ and Ar² are independently a substituted or unsubstituted aryl group, or a substituted or unsubstituted heteroaryl group, $L^1$, $L^2$, and $L^3$ are independently a single bond, a substituted or unsubstituted aryl group, or a substituted or unsubstituted heteroaryl group, and at least one of Ar¹, Ar², $L^1$, $L^2$ and $L^3$ is a substituted or unsubstituted heteroaryl group.

5. The device as claimed in claim 4, wherein at least one of Ar¹ and Ar² is a substituted or unsubstituted heteroaryl group, and $L^1$, $L^2$, and $L^3$ are independently a single bond, a substituted or unsubstituted aryl group having 6 to 18 ring carbon atoms.

6. The device as claimed in claim 4, wherein Ar¹ and Ar² are independently a substituted or unsubstituted aryl group having 6 to 24 ring carbon atoms, a substituted or unsubstituted carbazolyl group, a substituted or unsubstituted dibenzofuryl group, or a substituted or unsubstituted dibenzothienyl group.

7. The device as claimed in claim 4, wherein the material is a hole transport material.

8. The device as claimed in claim 4, wherein the material is in a layer disposed between an emission layer and an anode.

9. The device as claimed in claim 4, wherein the compound represented by Formula 1 includes one or more compounds represented in the following Formula 3 and Formula 4:

[Formula 3]

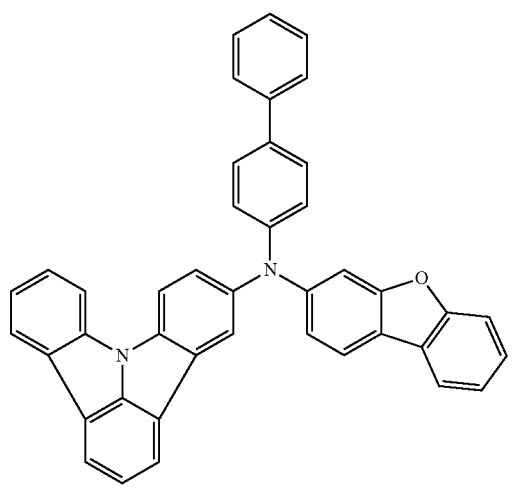

1

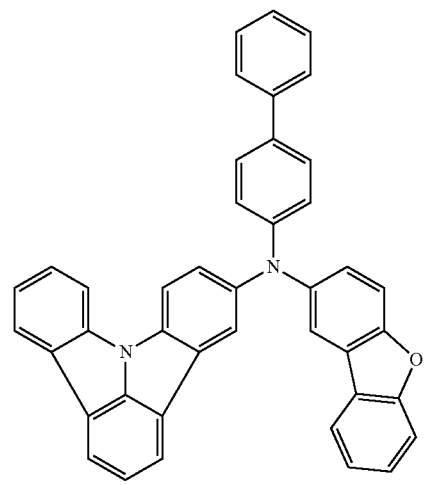

2

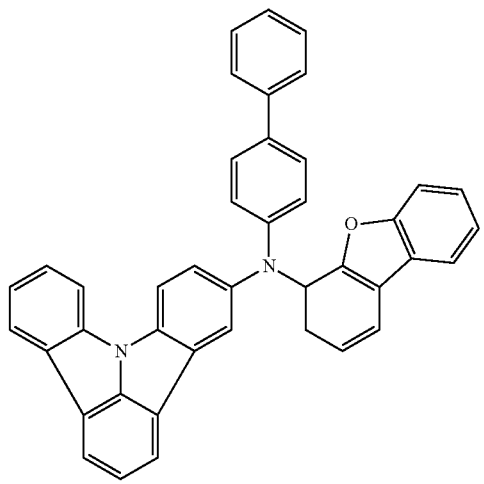

3

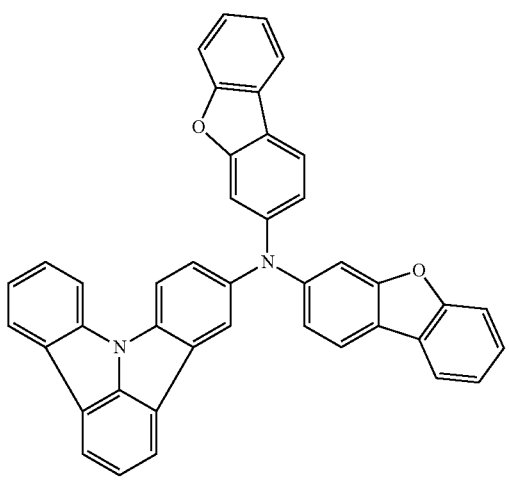

4

87
-continued
5
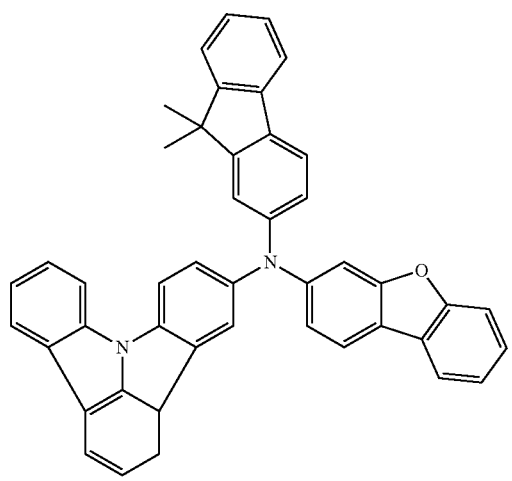
6
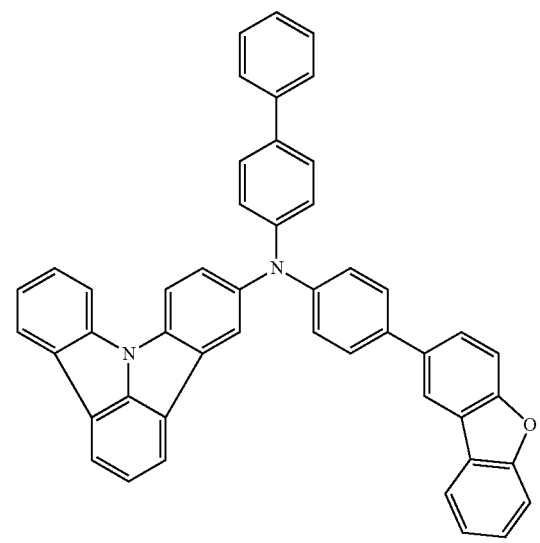
7
88
-continued
8
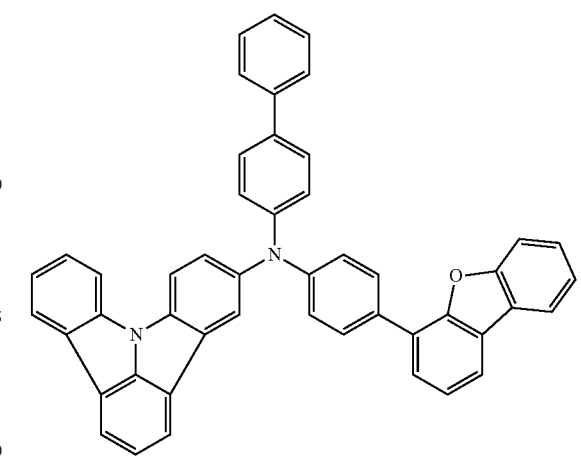
9
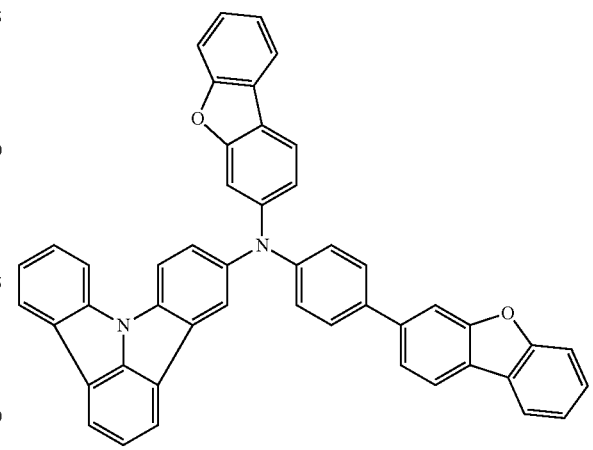
[Formula 4]
10
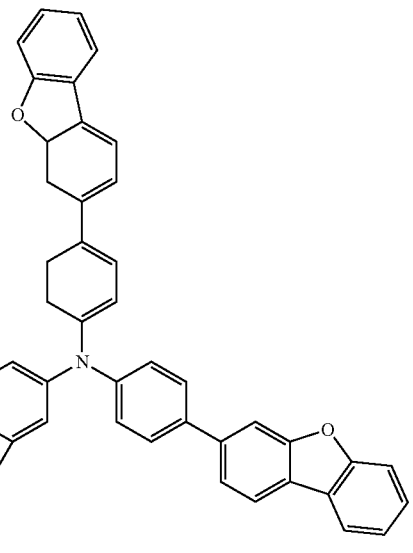

11
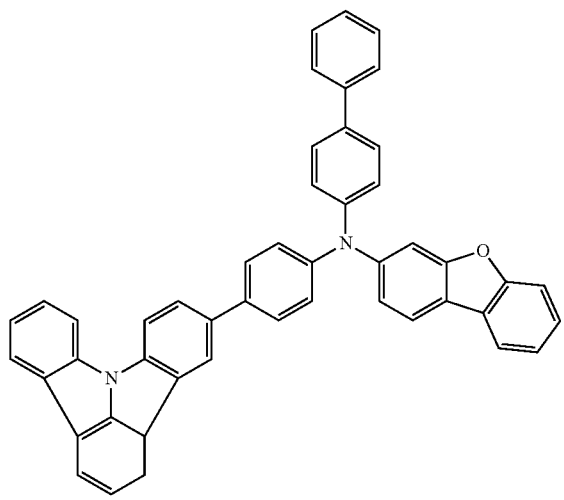
12
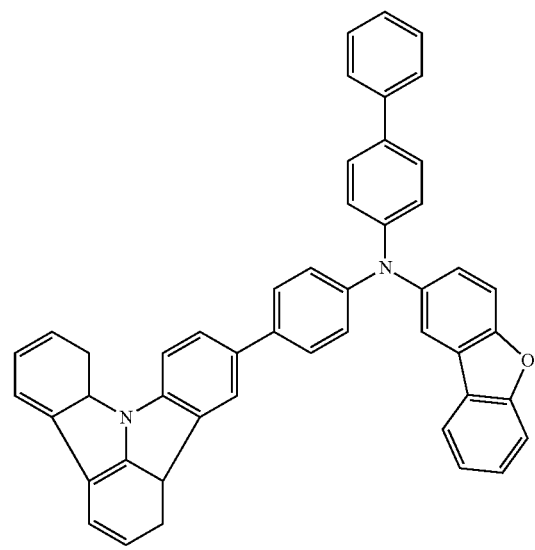
13
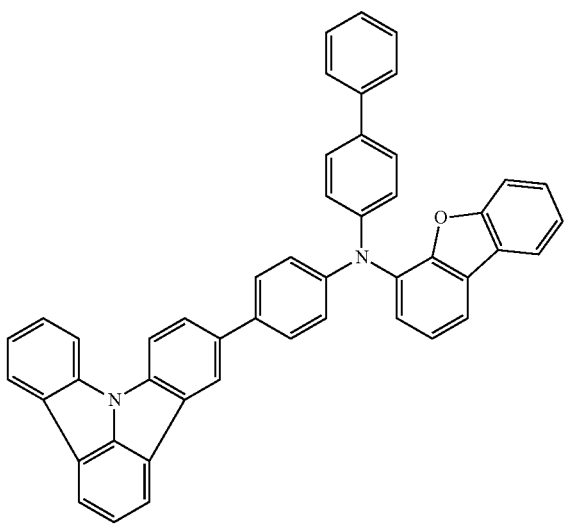
14
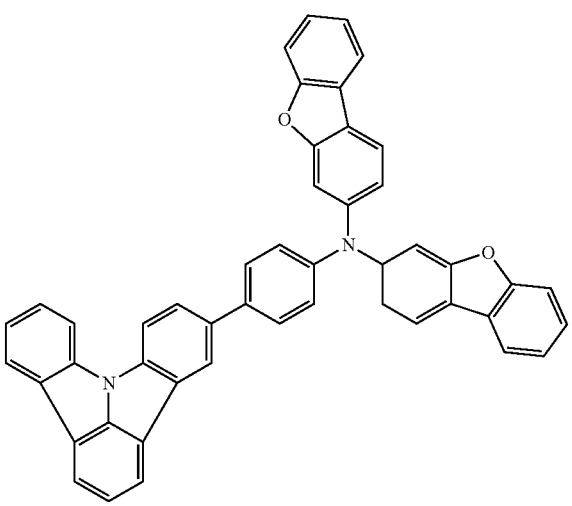
15
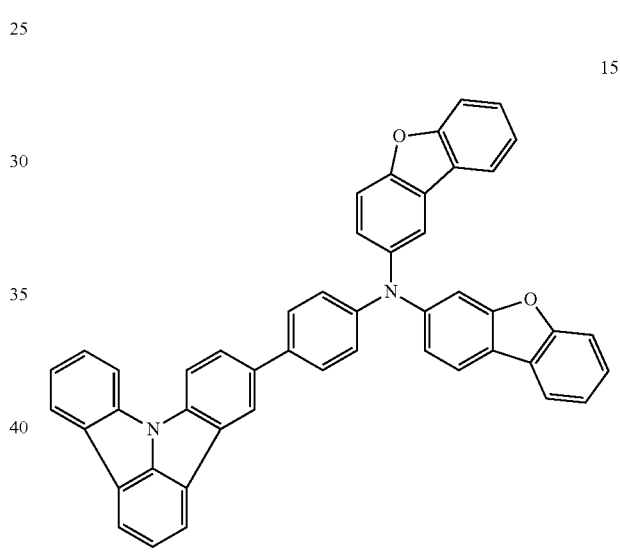
16
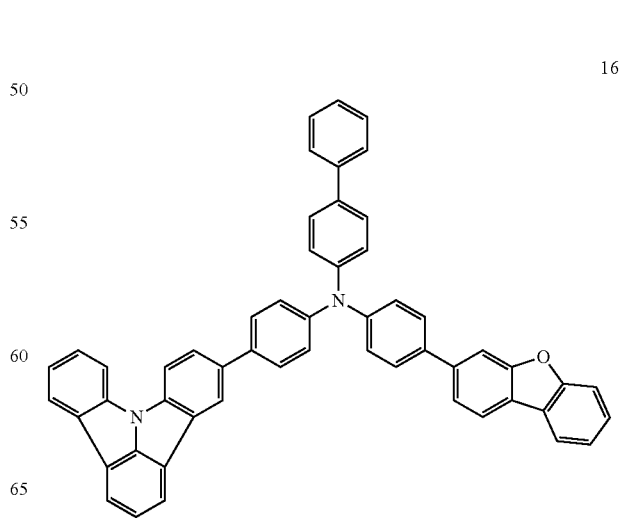

17
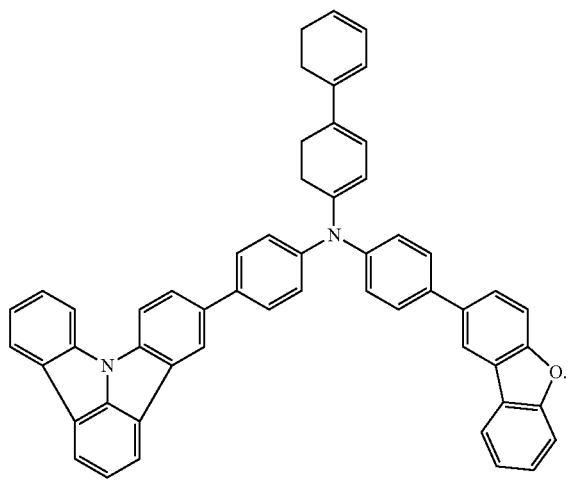
10. The device as claimed in claim 4, wherein the compound represented by Formula 1 includes one or more compounds represented in the following Formula 5 and Formula 6:
[Formula 5]
18
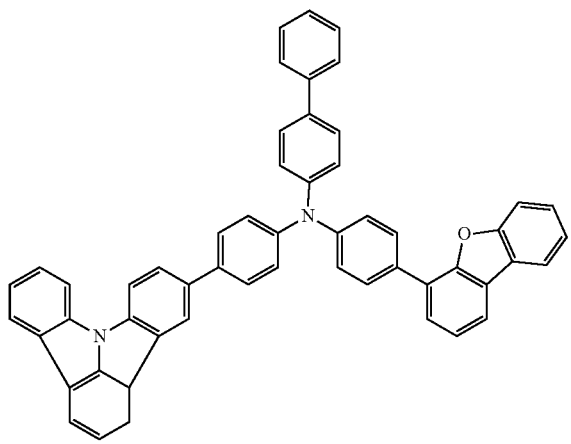
19
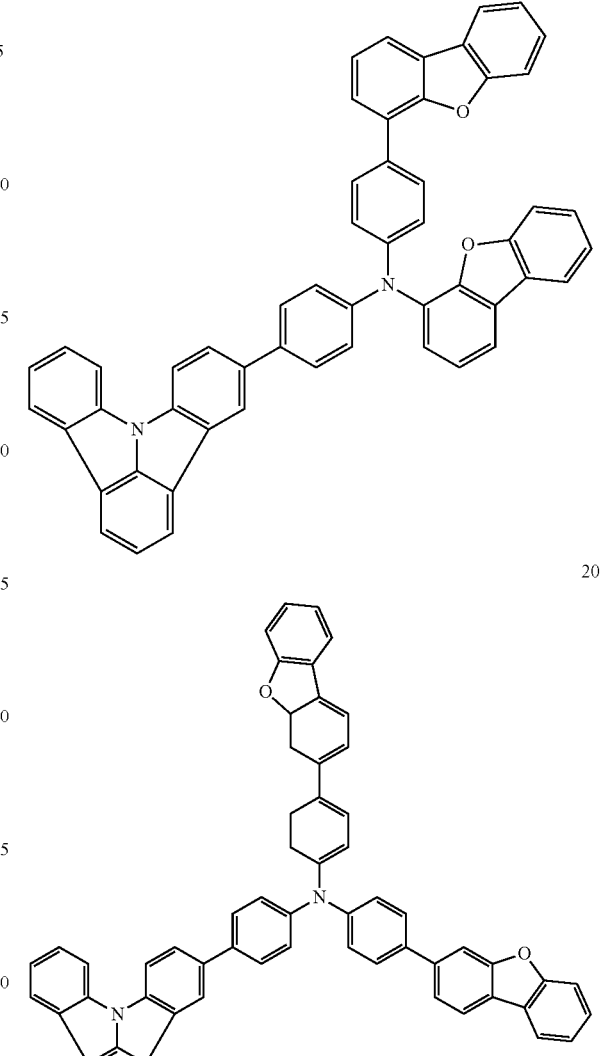

93
-continued
22
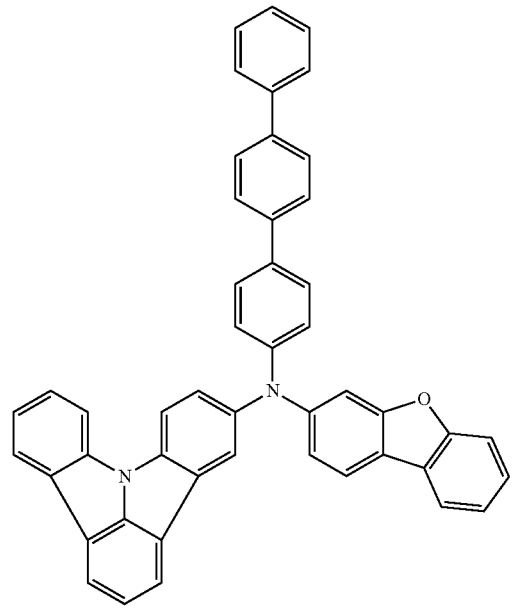
23
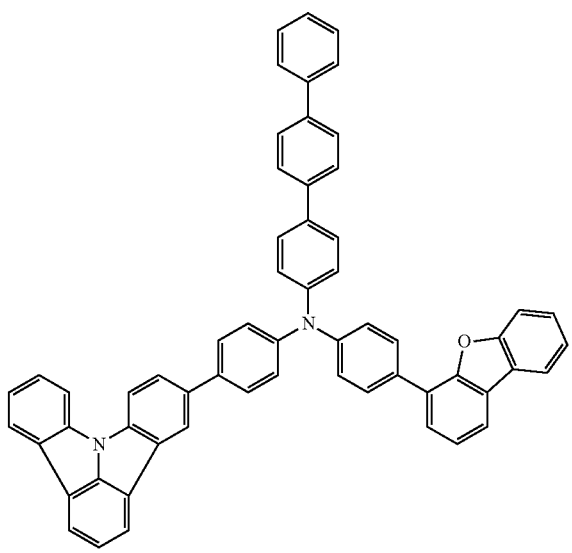
[Formula 6]
24
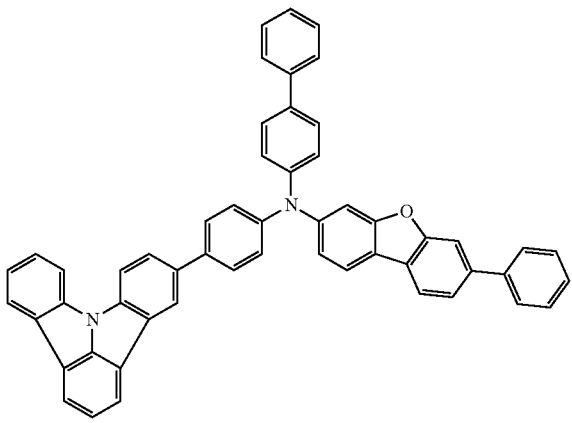
94
-continued
25
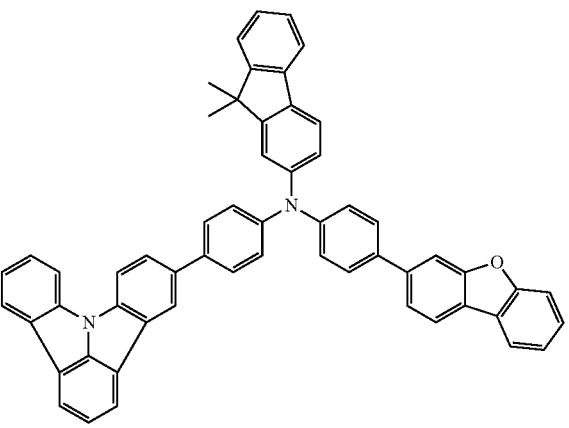
26
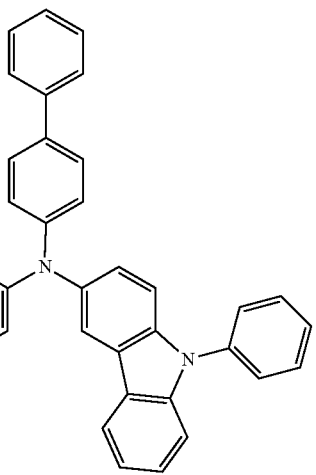
27

28
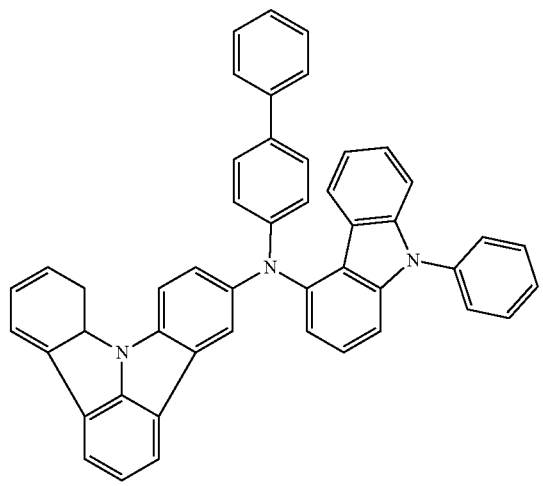
29
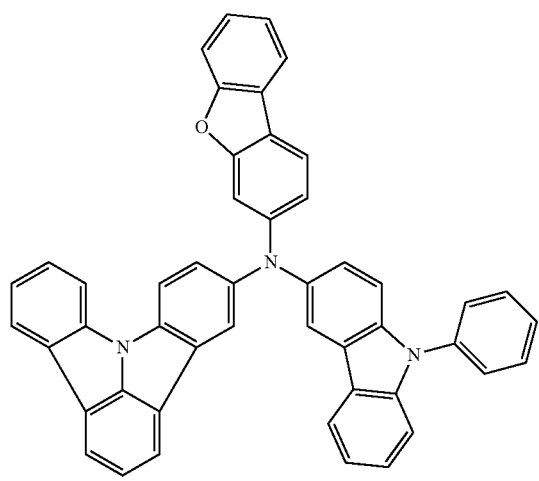
30
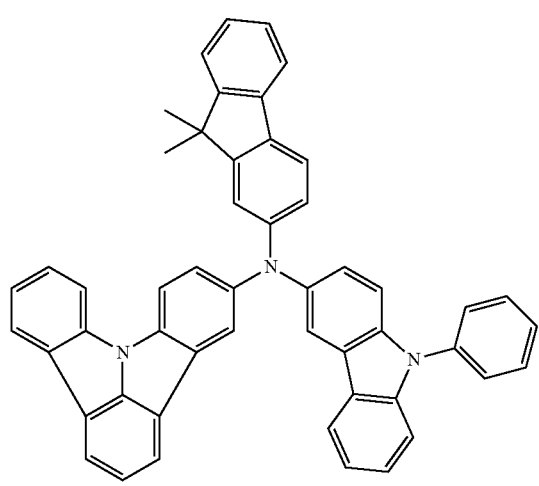
31
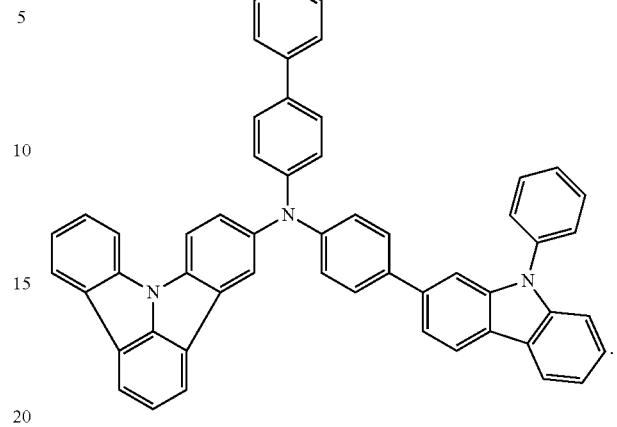
11. The device as claimed in claim 4, wherein the compound represented by Formula 1 includes one or more compounds represented in the following Formula 7 and Formula 8:
[Formula 7]
32
33
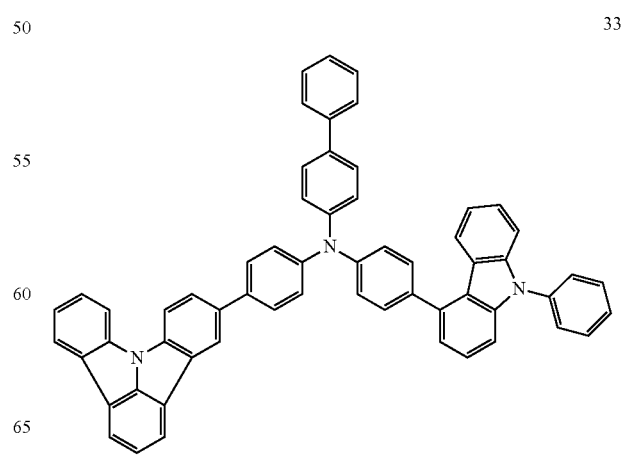

34
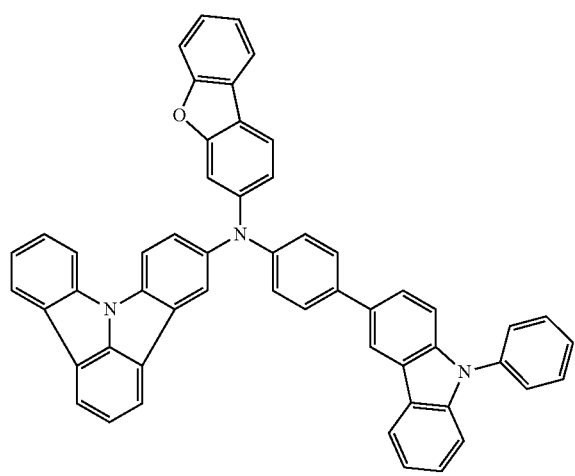
35
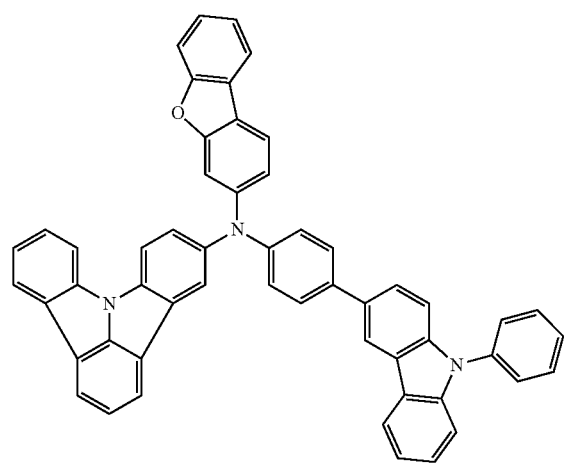
36
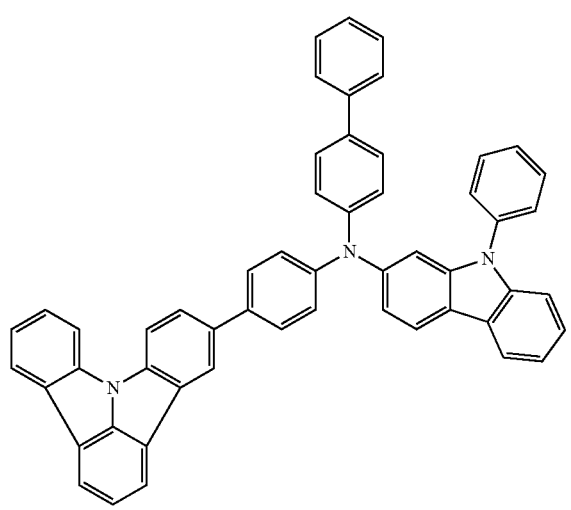
37
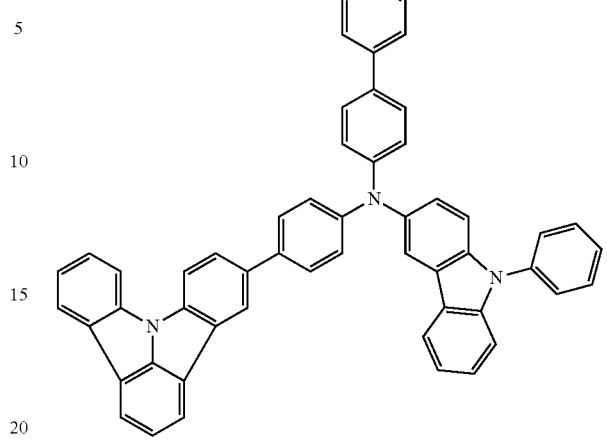
38
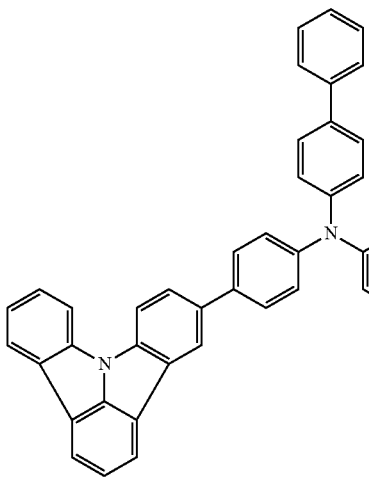
39
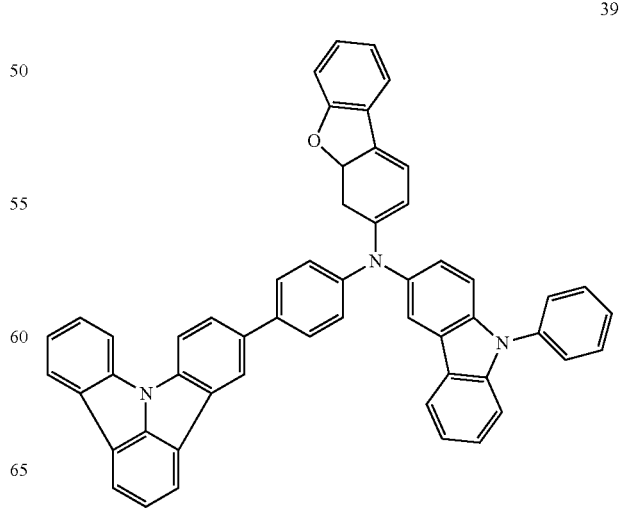

99 100
-continued -continued
40
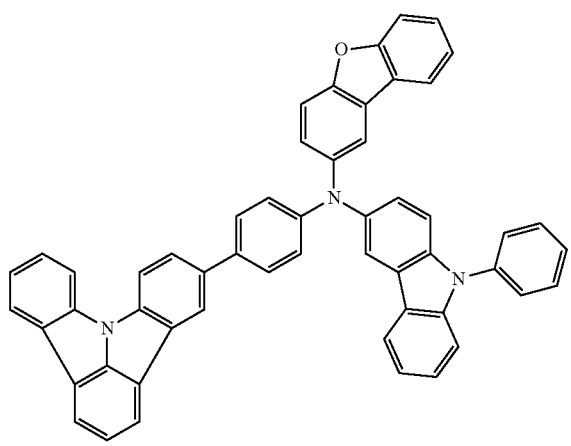
[Formula 8]
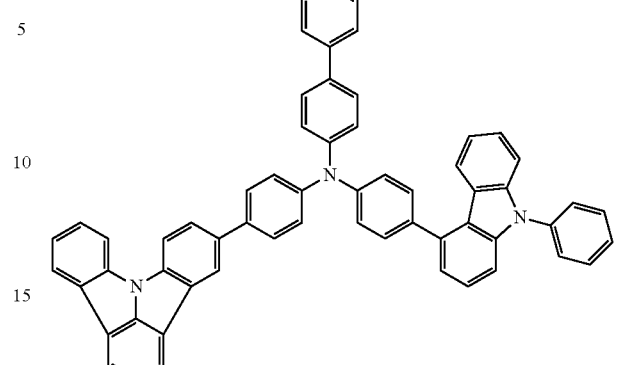
43
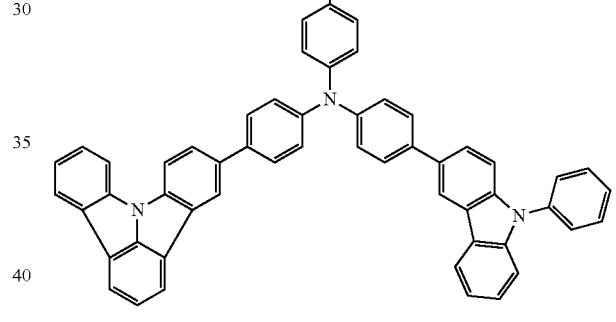
44
41
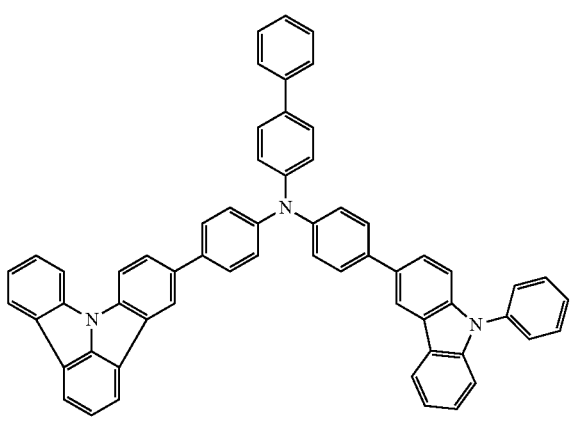
42
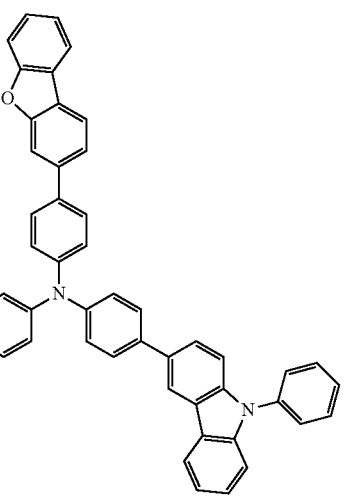
45

101
-continued
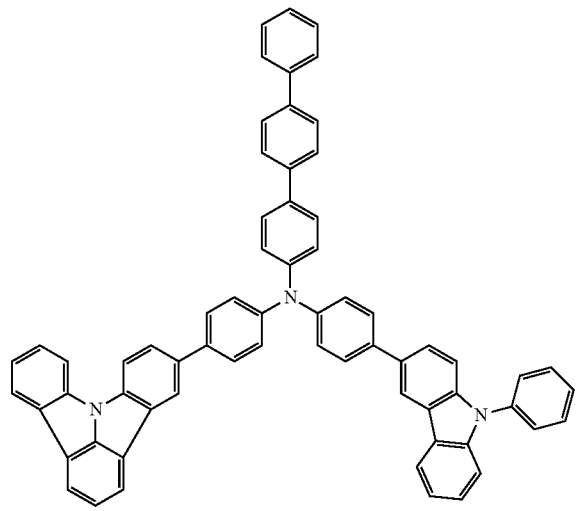
46
102
-continued
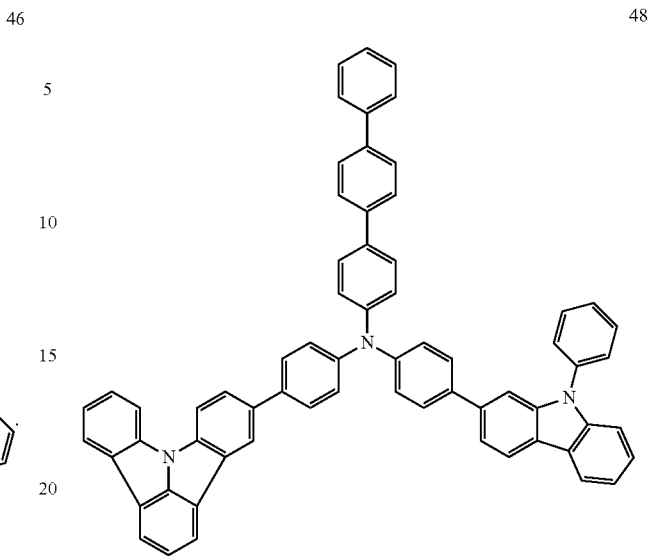
48
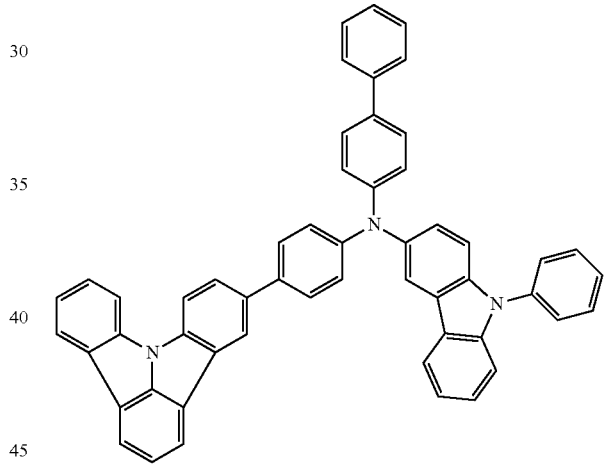
49
12. The device as claimed in claim 4, wherein the compound represented by Formula 1 includes one or more compounds represented in the following Formula 9 and Formula 10:
[Formula 9]
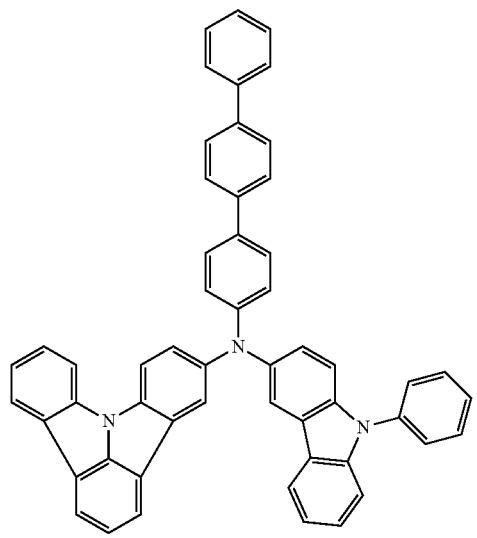
47
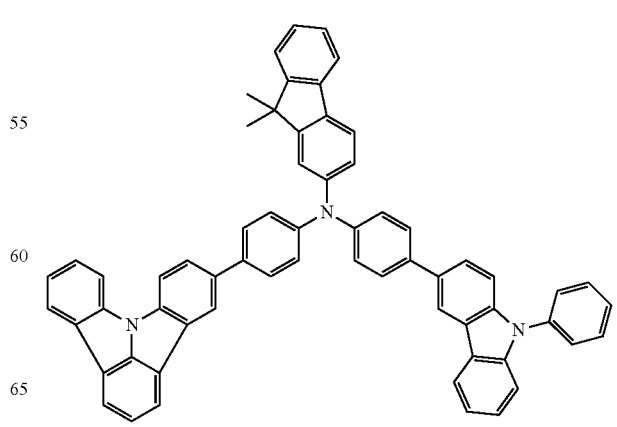
50

51
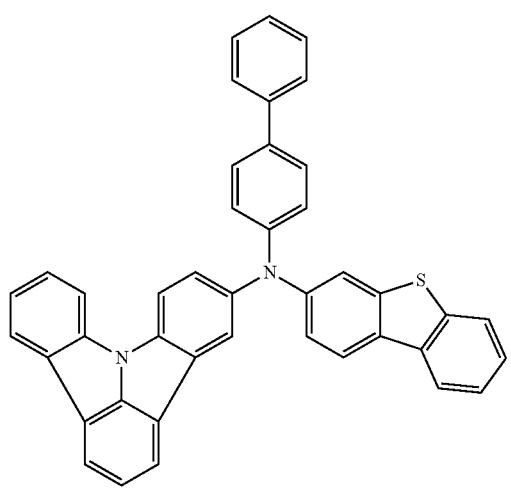
54
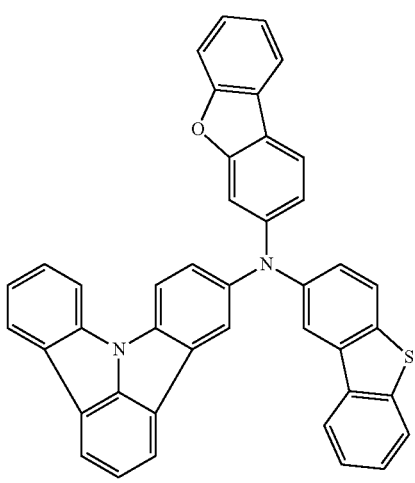
52
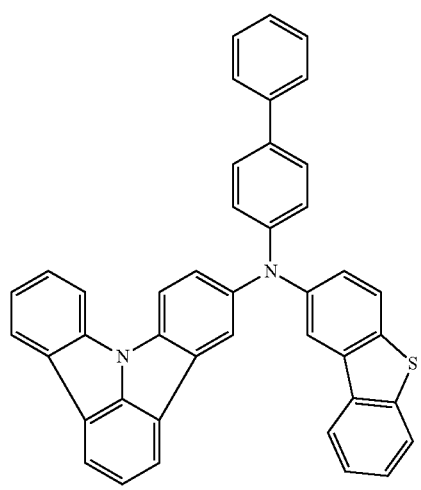
55
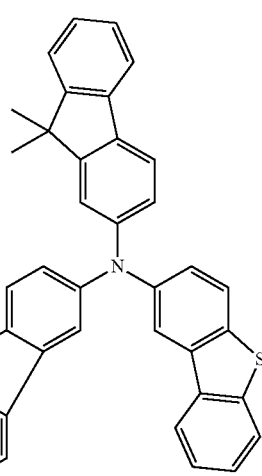
[Formula 10]
53
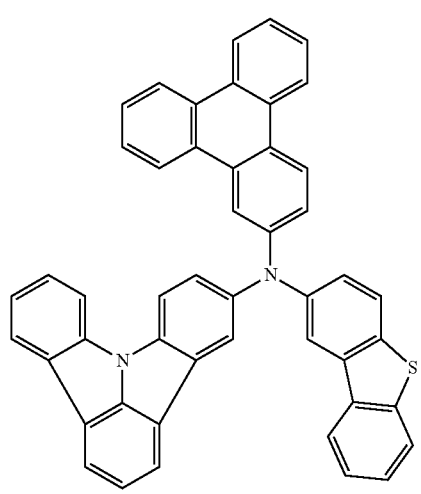
56
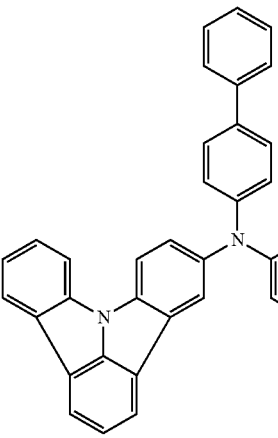

57
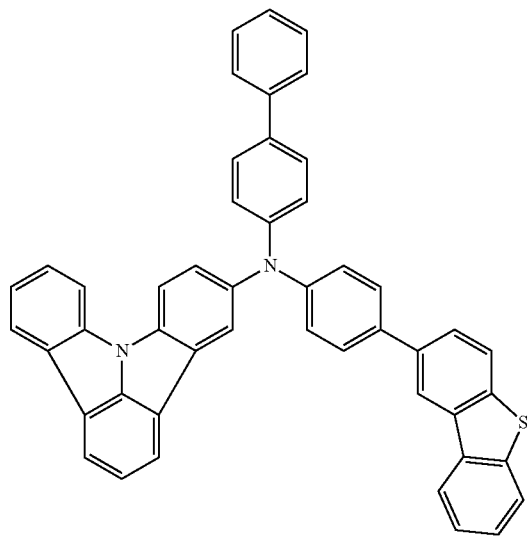
58
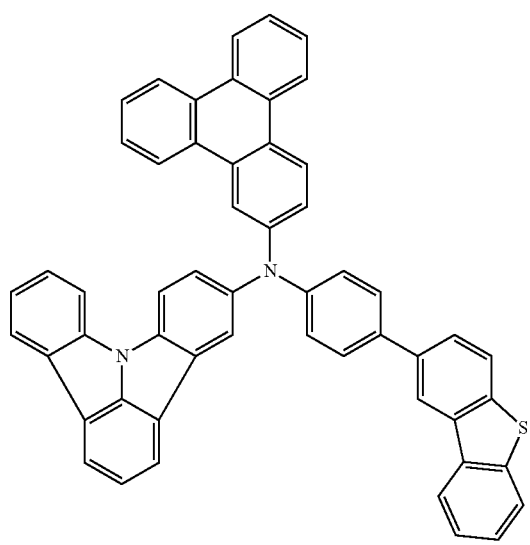
59
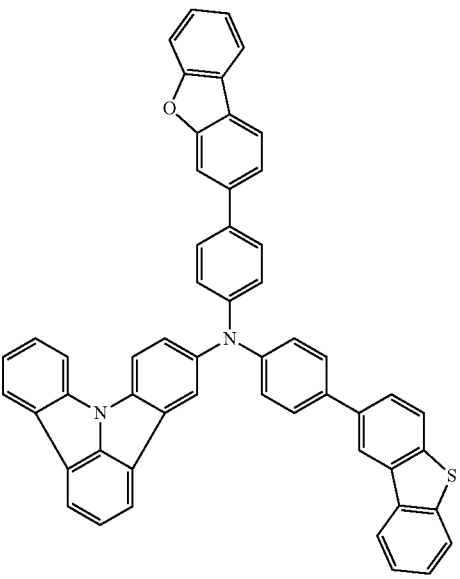
60
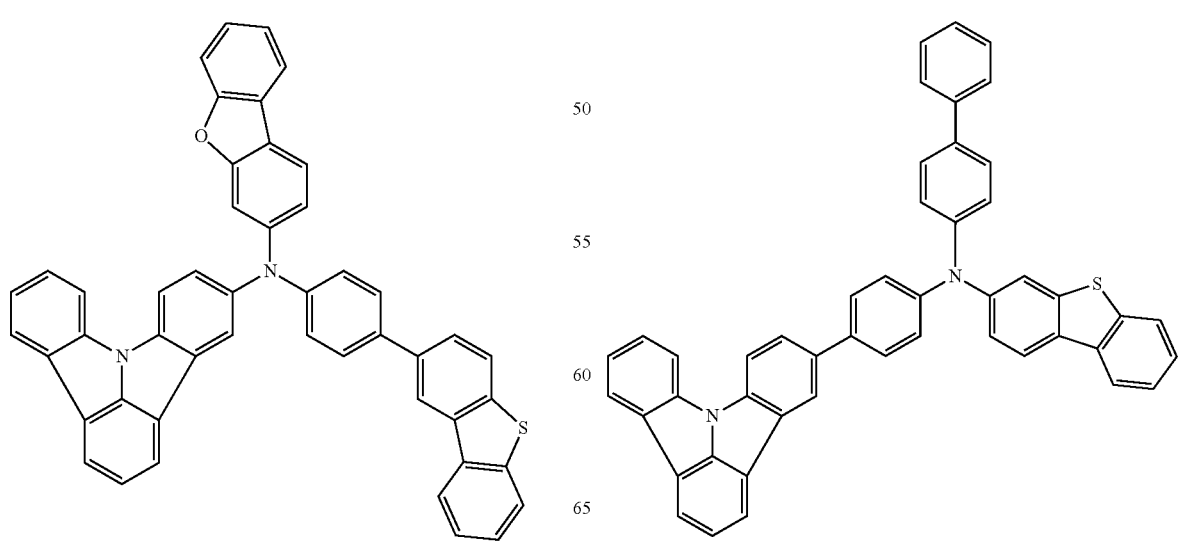
61

62
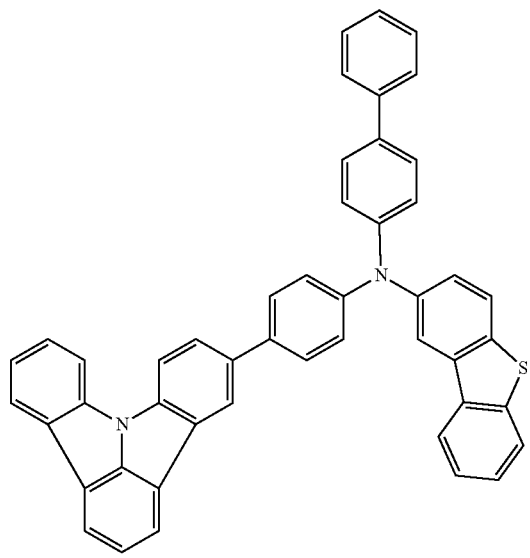
64
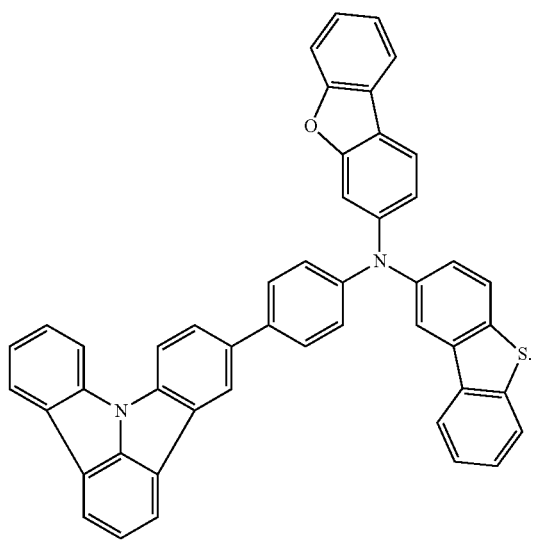
13. The device as claimed in claim 4, wherein the compound represented by Formula 1 includes one or more compounds represented in the following Formula 11 and Formula 12:
[Formula 11]
63
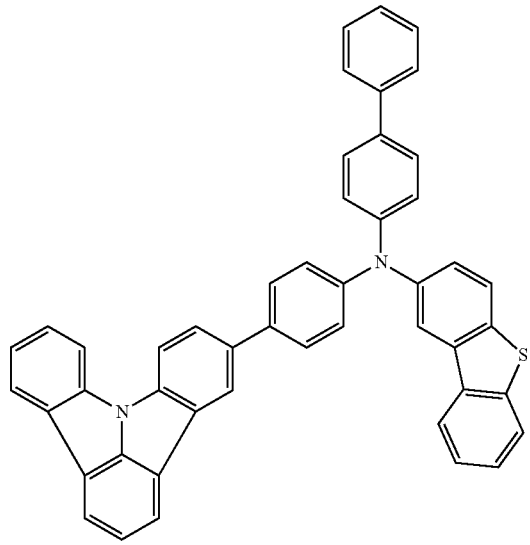
65
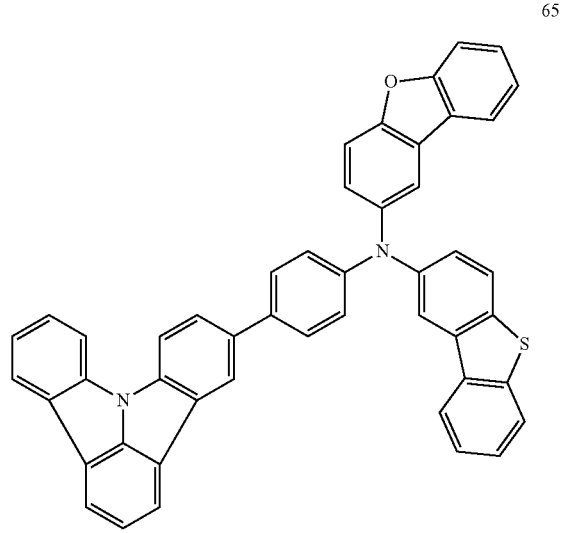

66
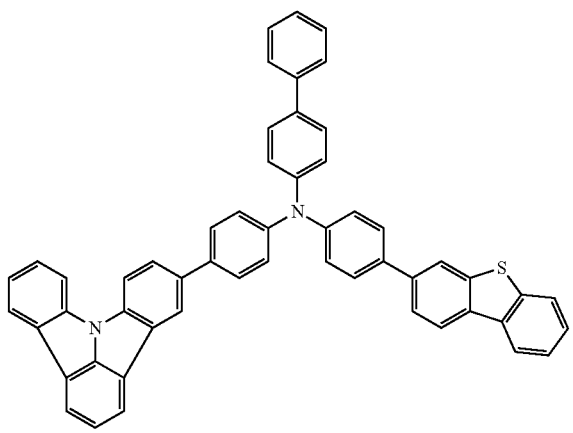
67
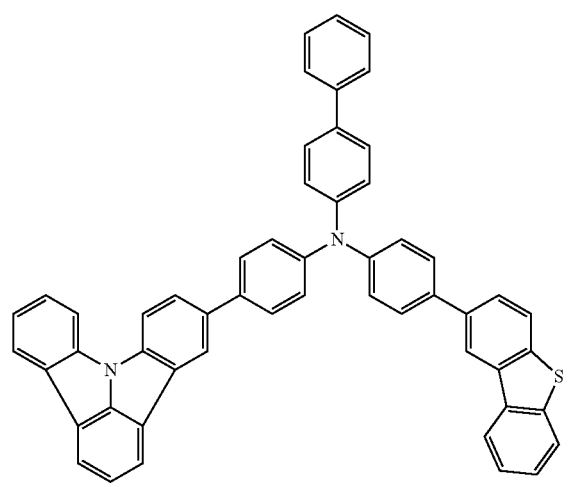
68
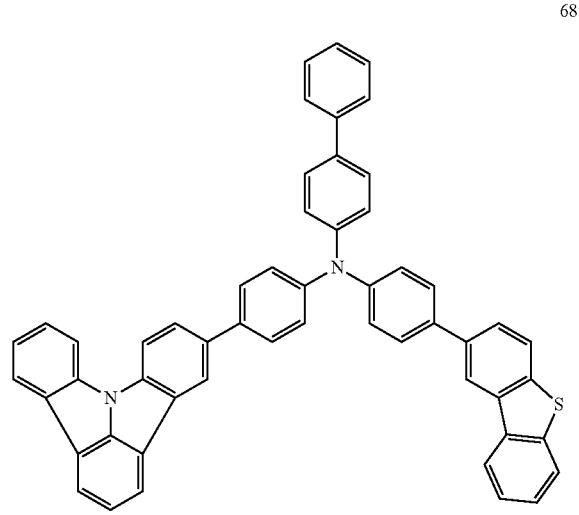
69
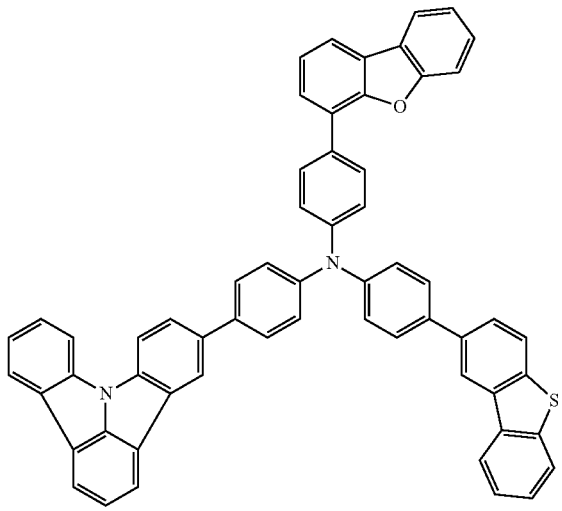
70
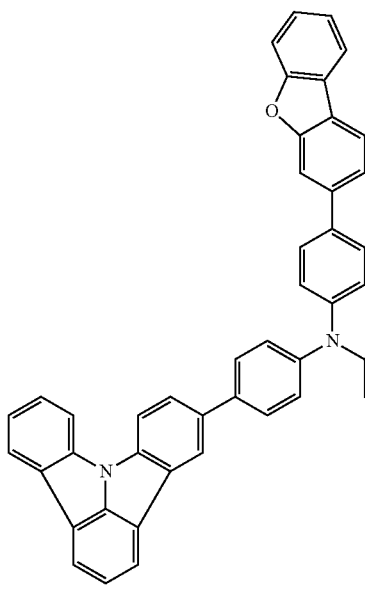

[Formula 12]
71
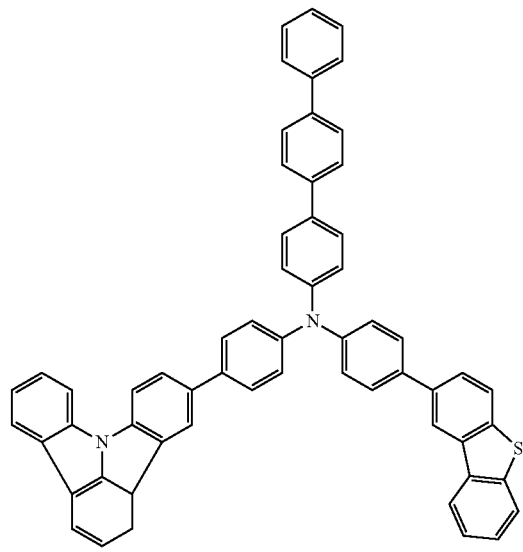
72
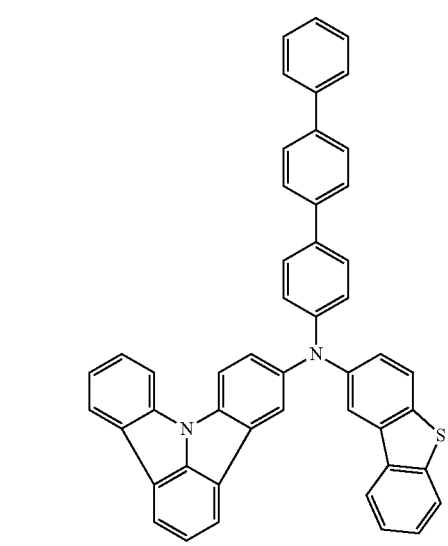
73
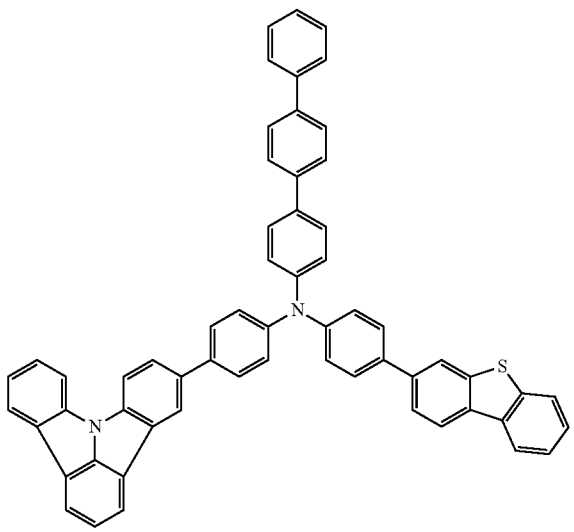
74
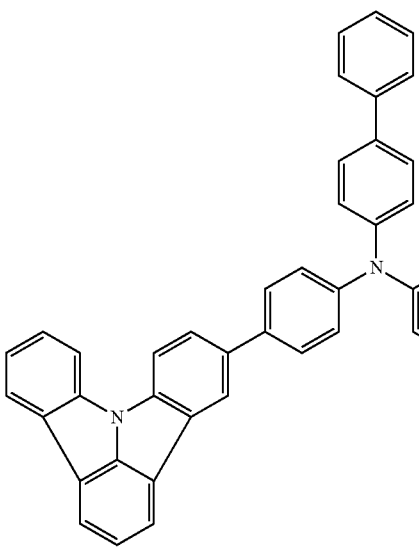
75
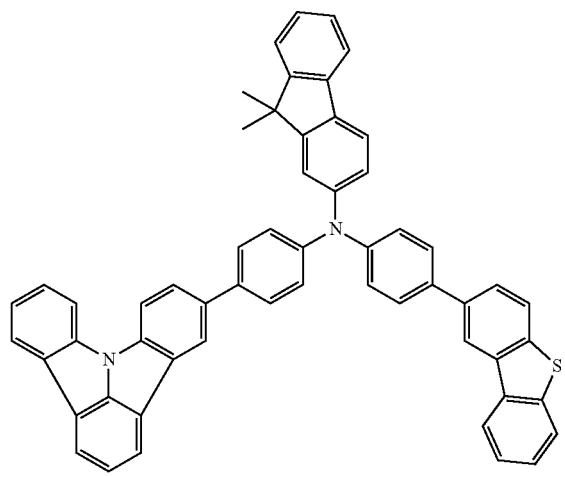
76
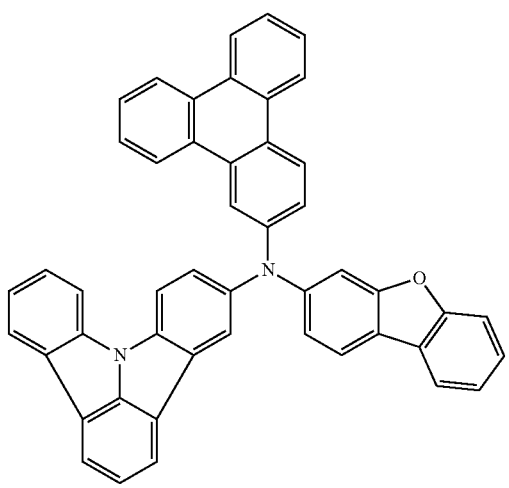

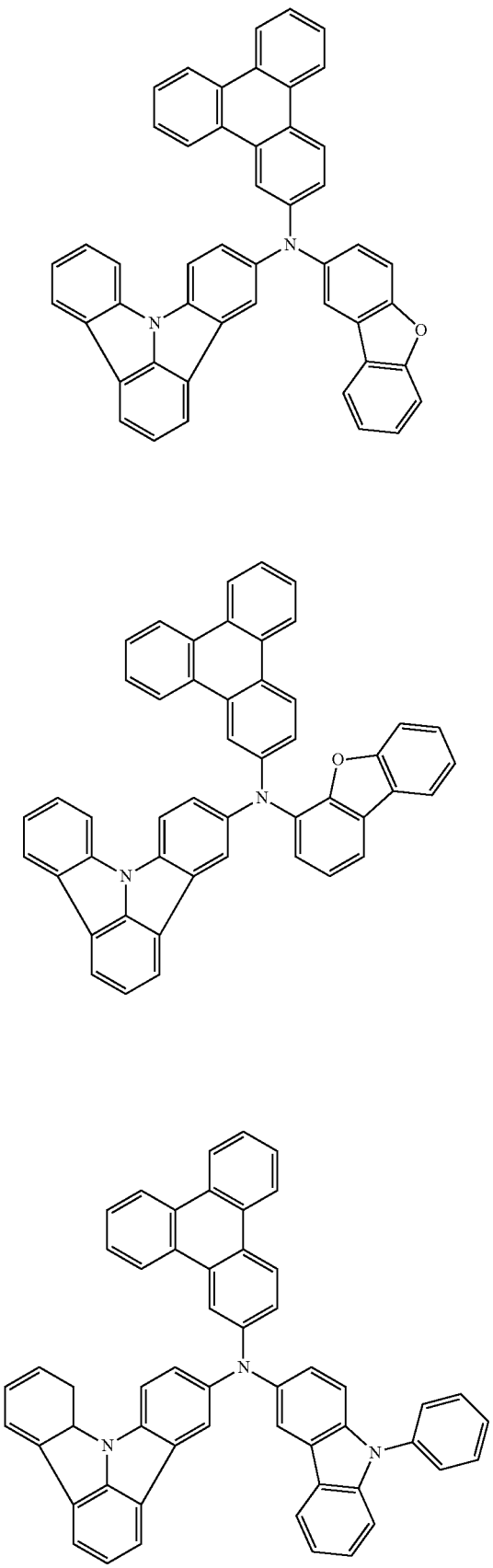
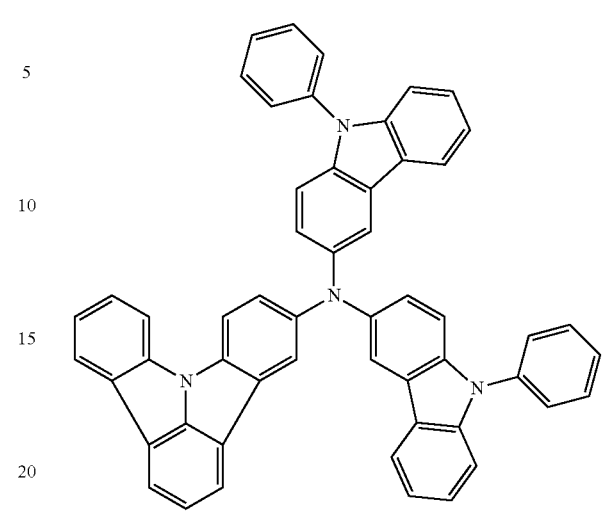
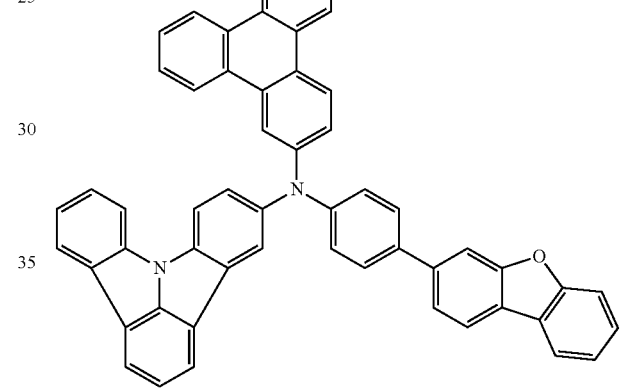
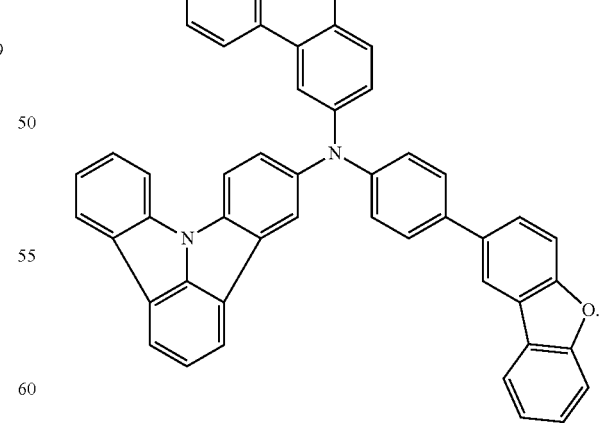
14. The device as claimed in claim 4, wherein the compound represented by Formula 1 includes one or more compounds represented in the following Formula 13 and Formula 14:

[Formula 13]
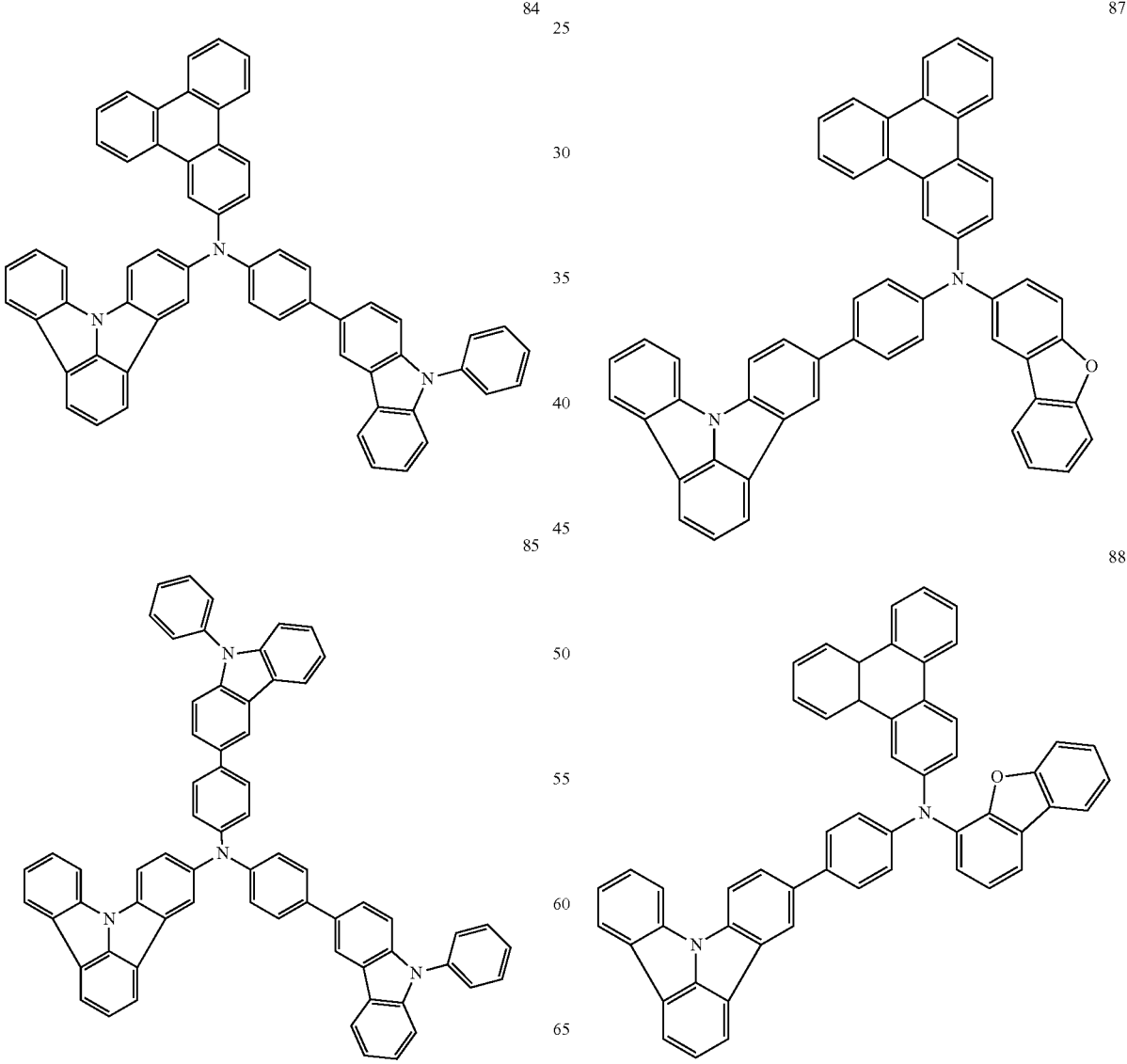

89
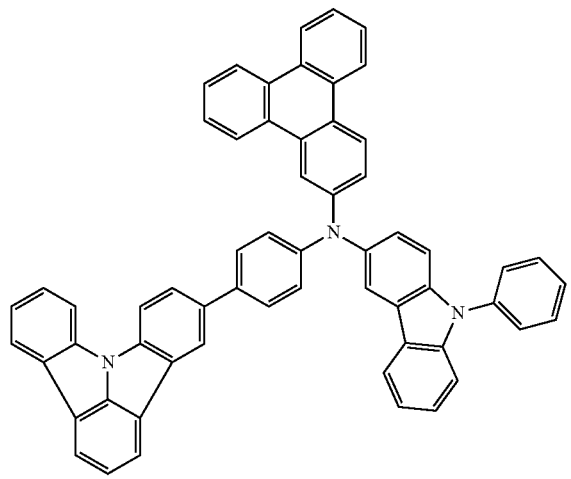
90
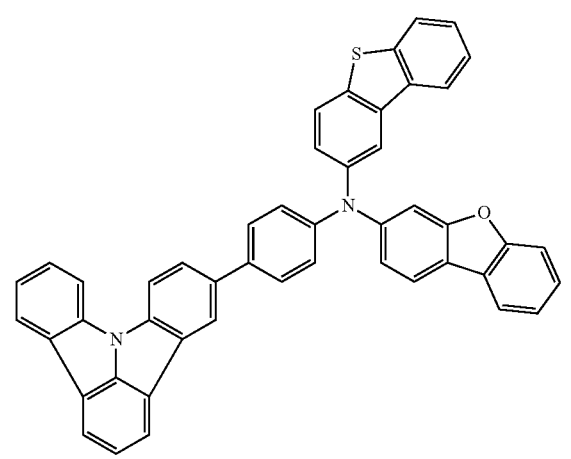
91
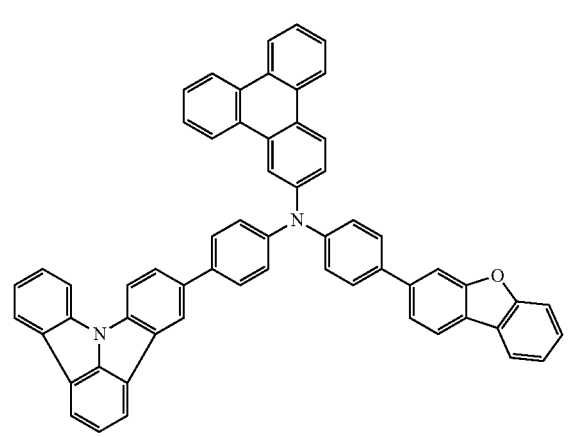
[Formula 14]
92
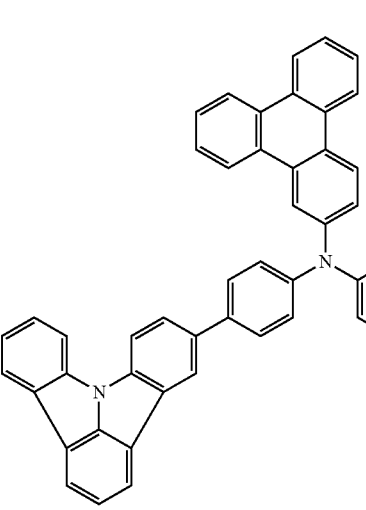
93
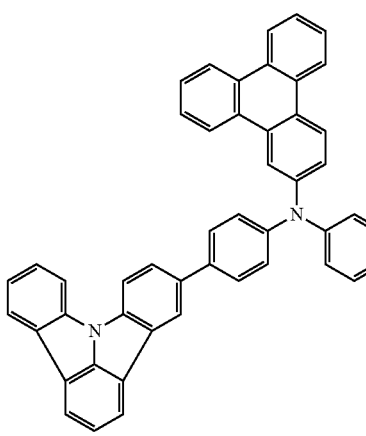
94
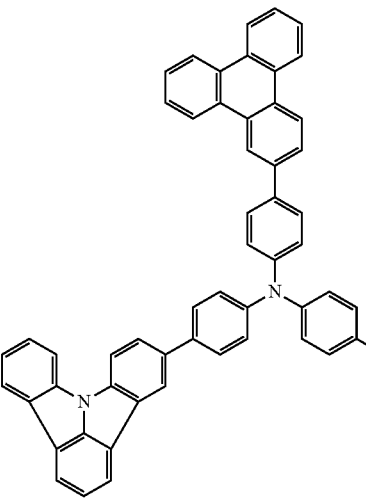

119
-continued
95
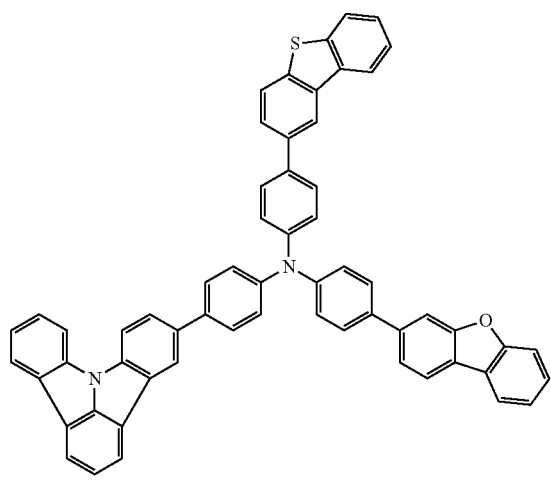
96
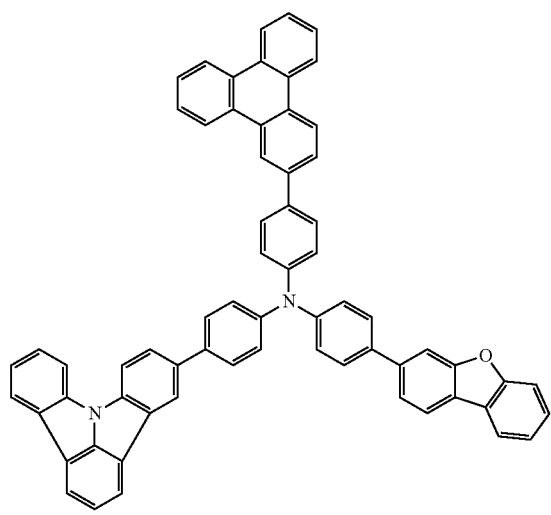
97
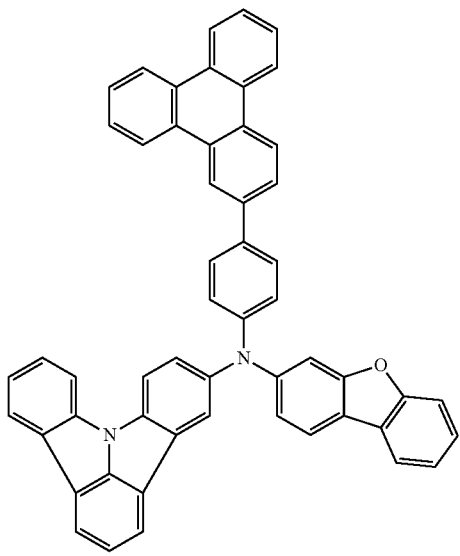
120
-continued
98
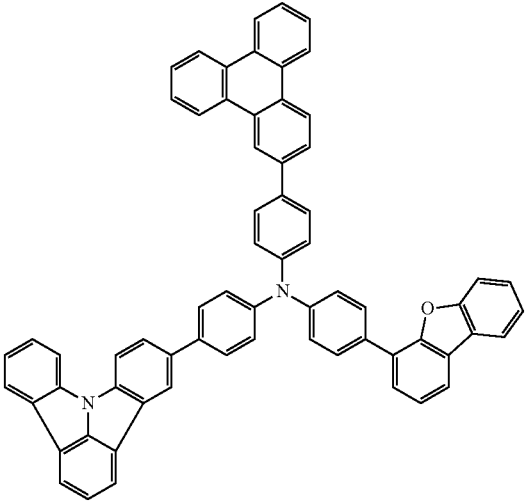
15. The device as claimed in claim 4, wherein the compound represented by Formula 1 includes one or more compounds represented in the following Formula 15 and Formula 16:
[Formula 15]
99
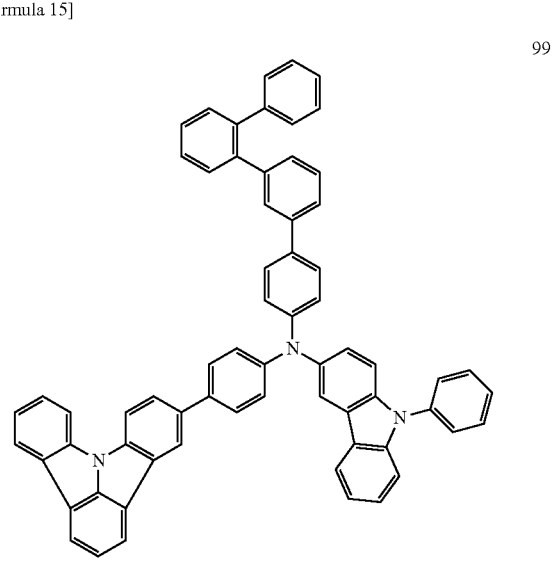

-continued 100
101
102
103
104
105

106
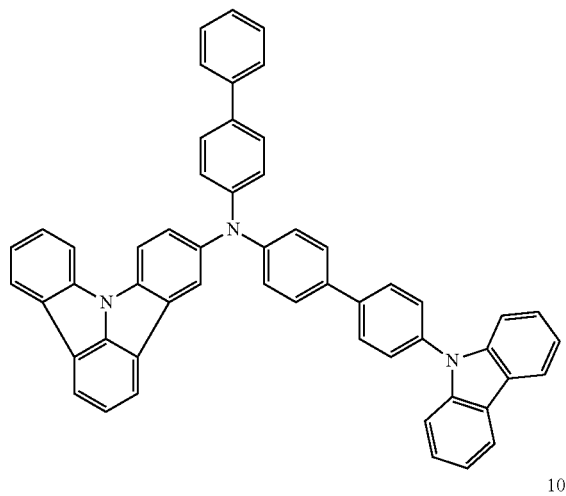
107
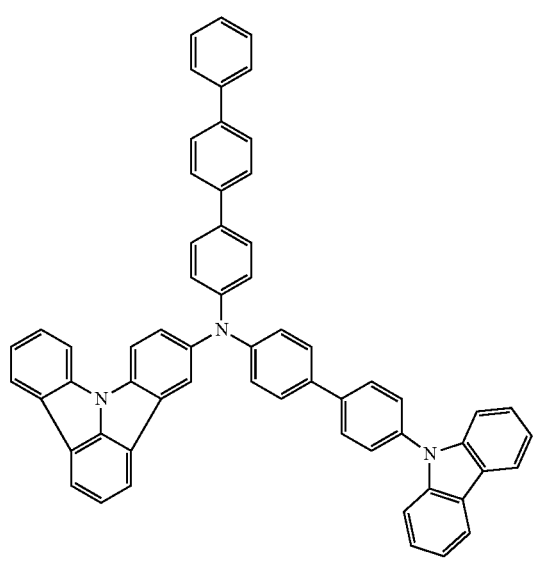
[Formula 16]
108
109
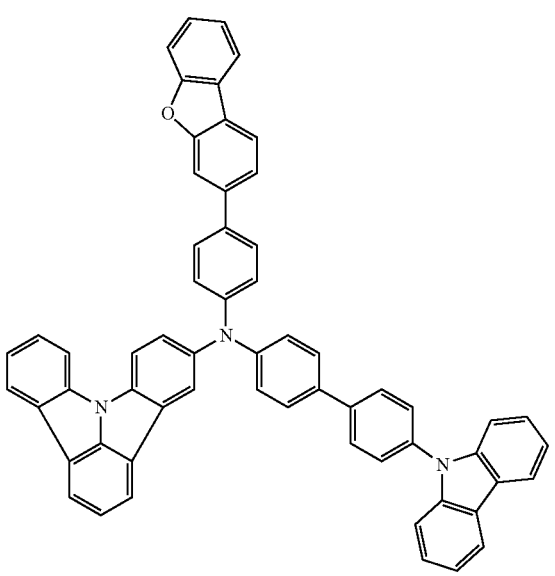
110
111
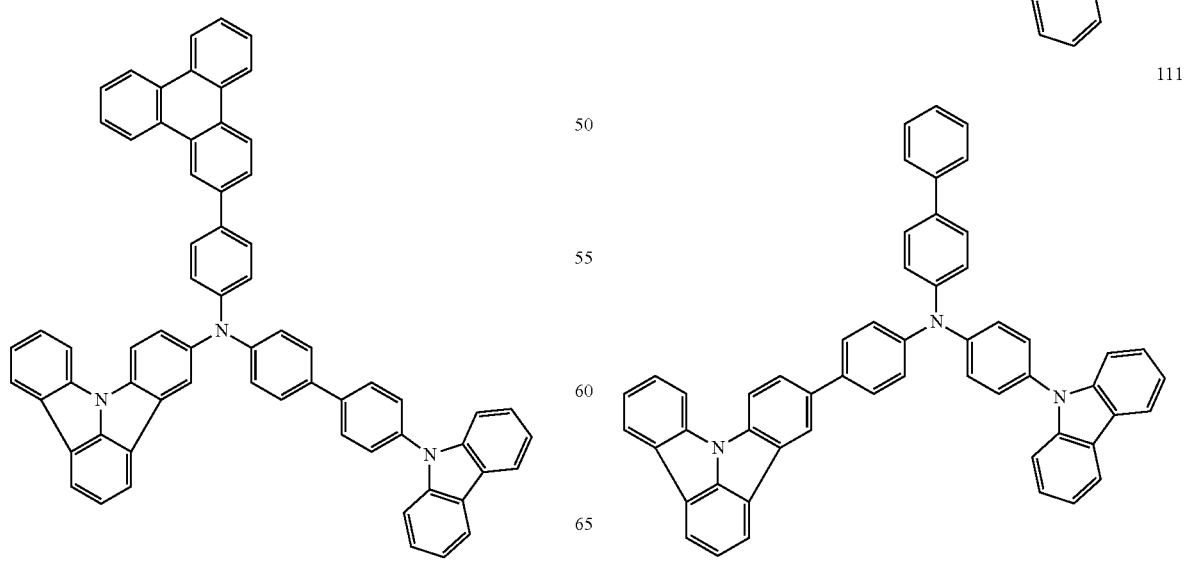

125
-continued
112
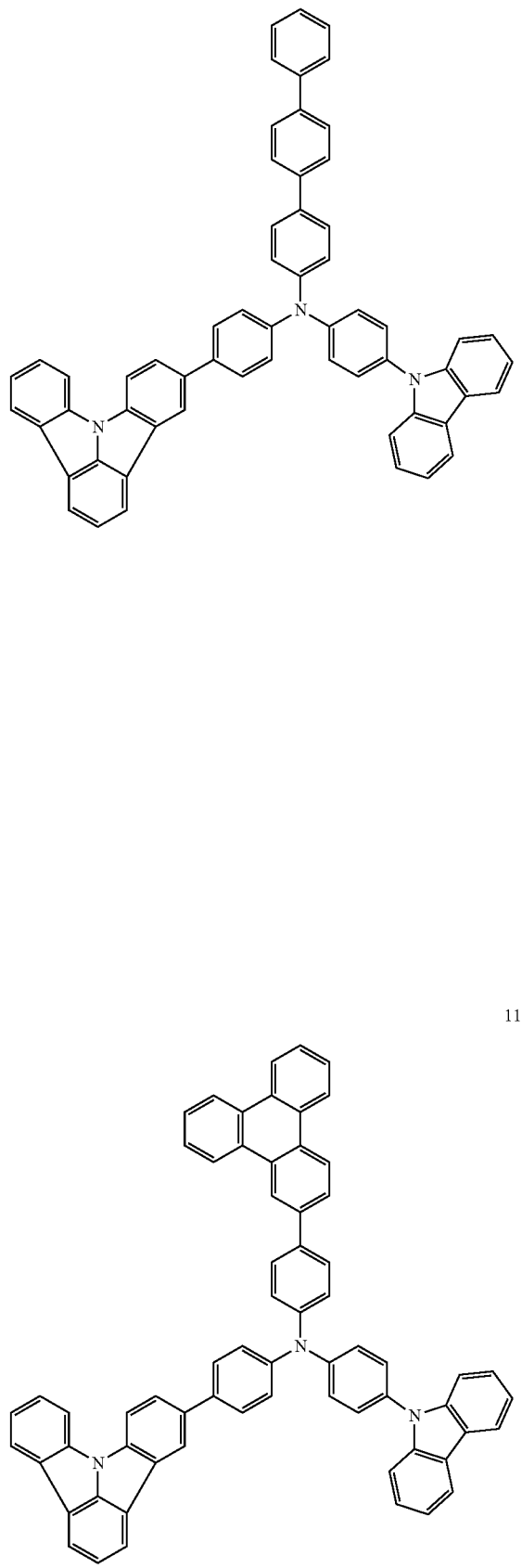
113
126
-continued
114
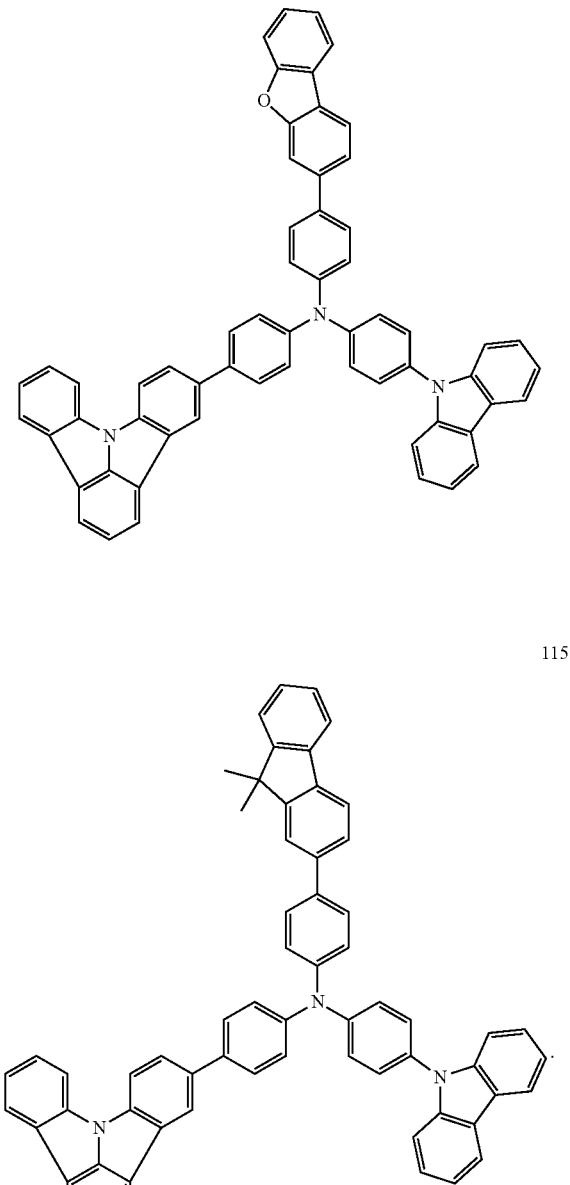
115
16. The device as claimed in claim 4, wherein the compound represented by Formula 1 includes one or more compounds represented in the following Formula 17 and Formula 18:

[Formula 17]
116
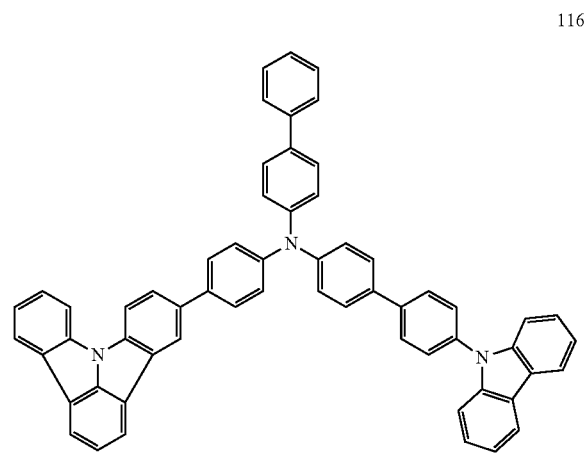
117
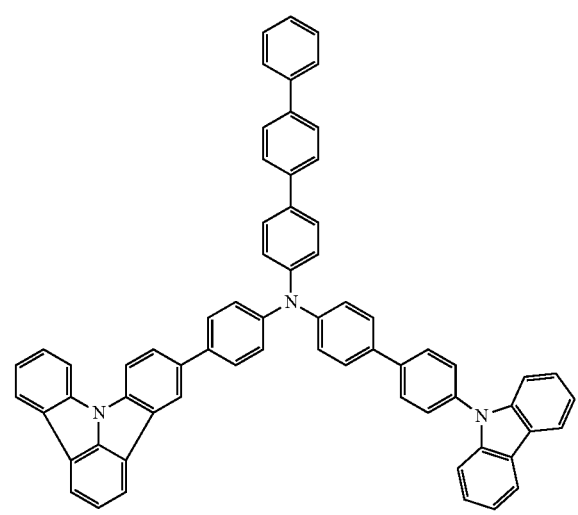
118
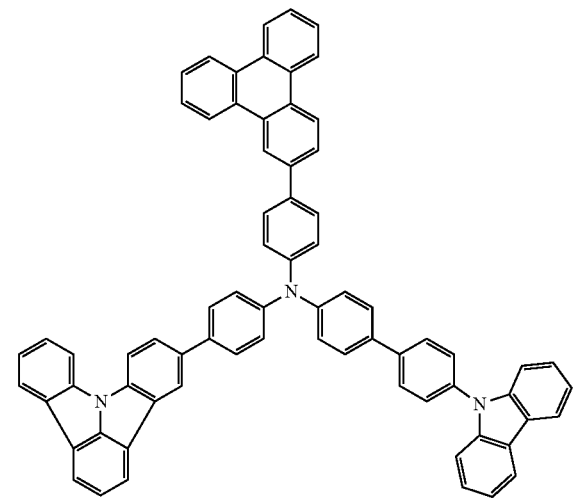
-continued
119
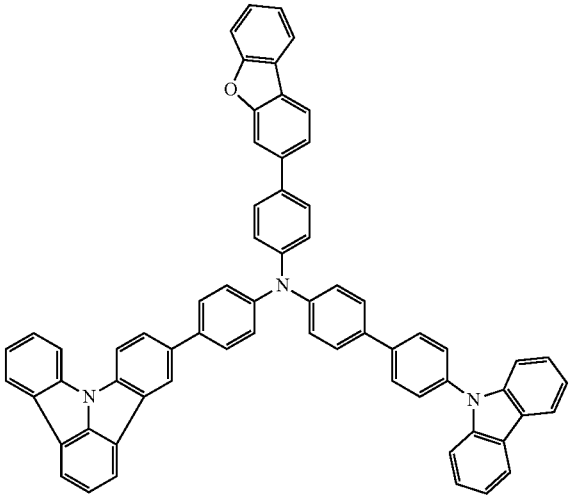
120
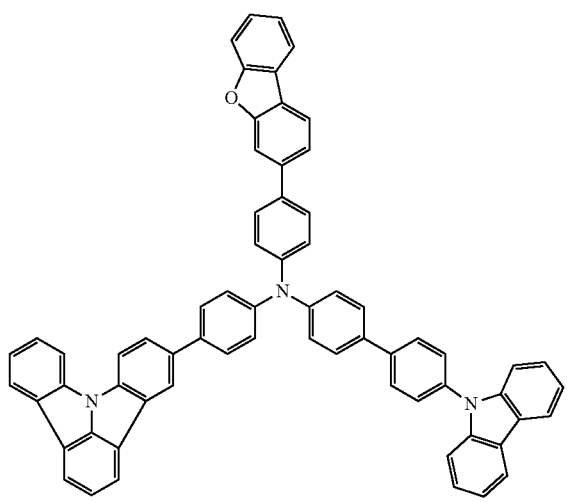
121
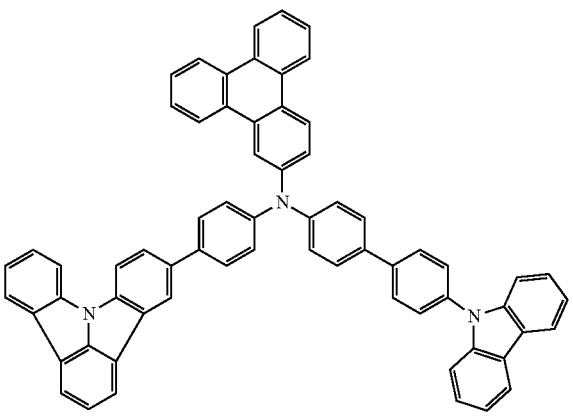

[Formula 18]
122
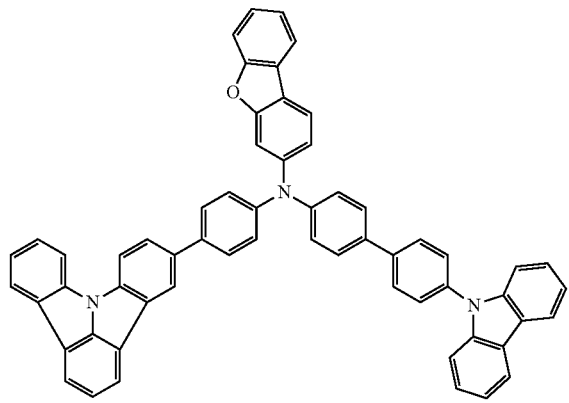
125
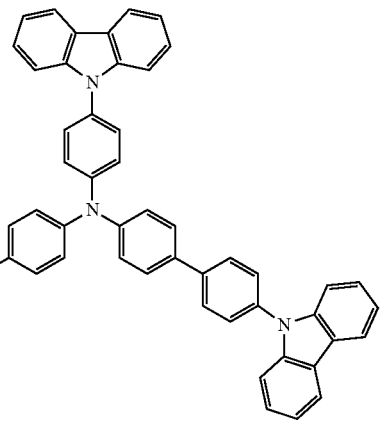
123
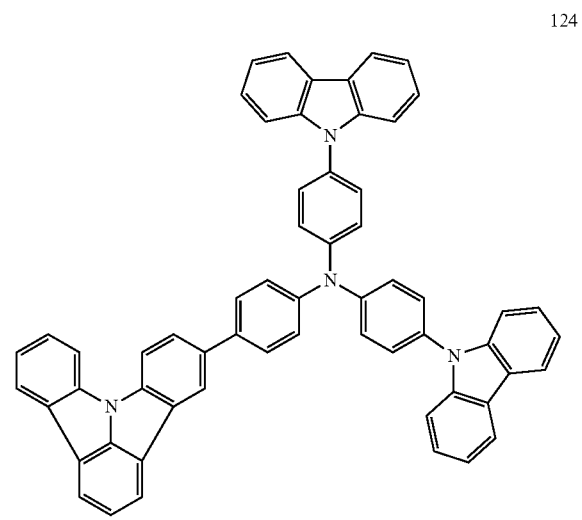
126
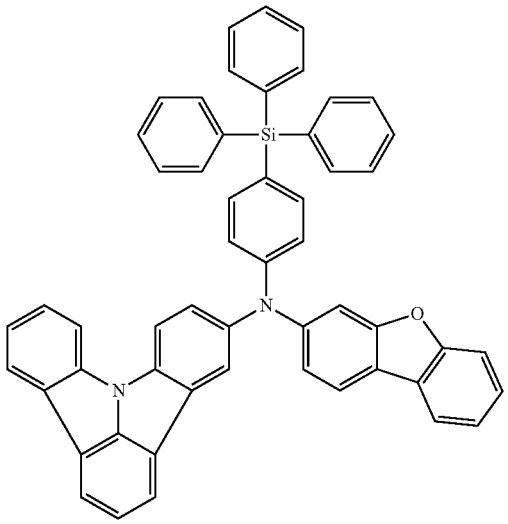
124
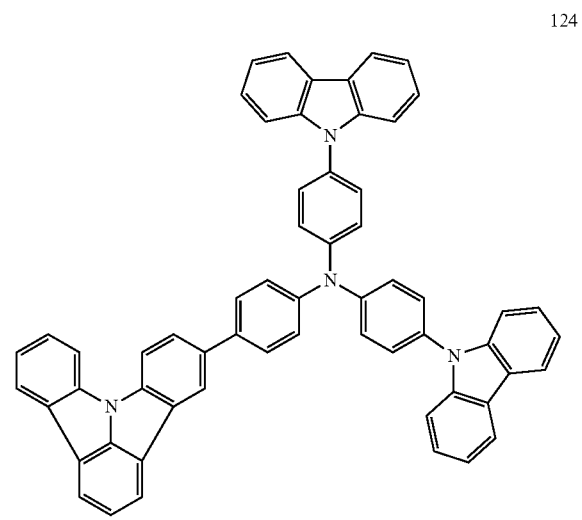
127
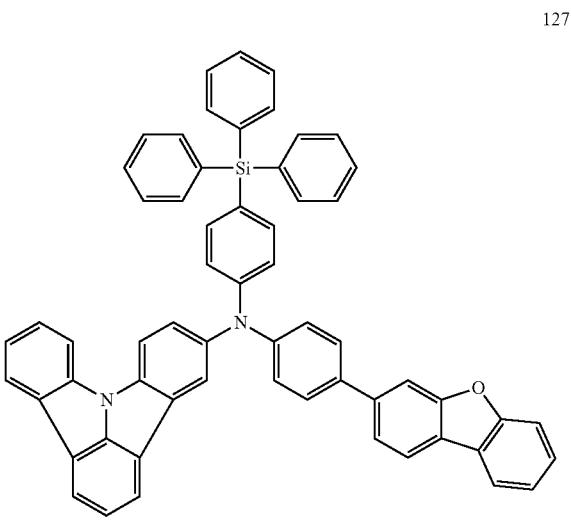

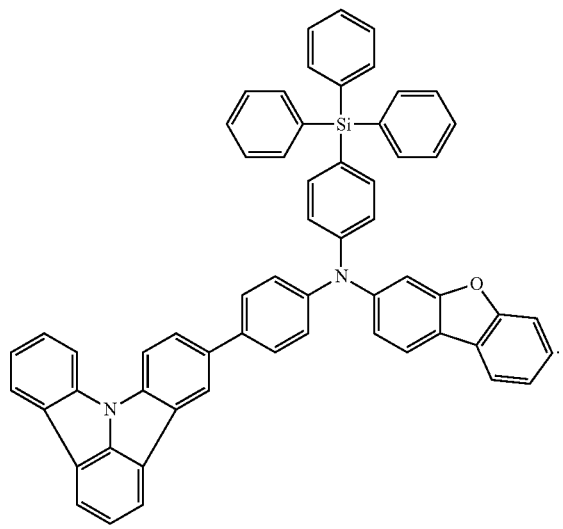
128
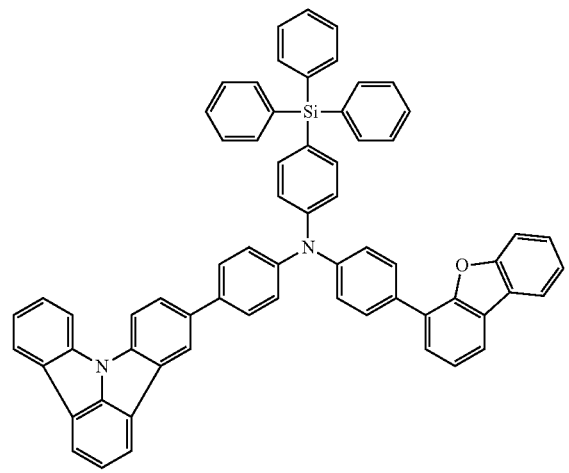
130
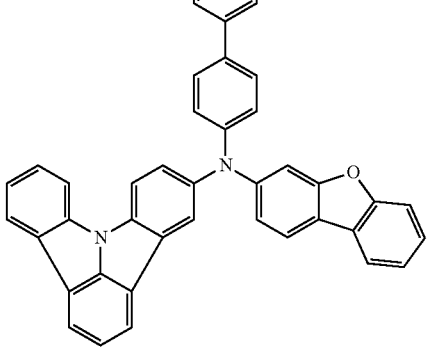
131
17. The device as claimed in claim 4, wherein the compound represented by Formula 1 includes one or more compounds represented in the following Formula 19 and Formula 10:
[Formula 19]
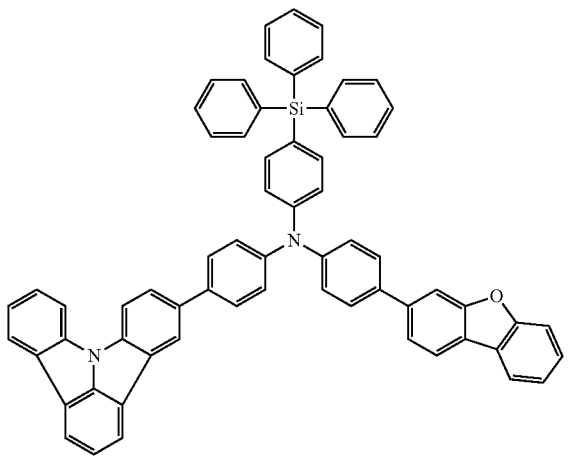
129
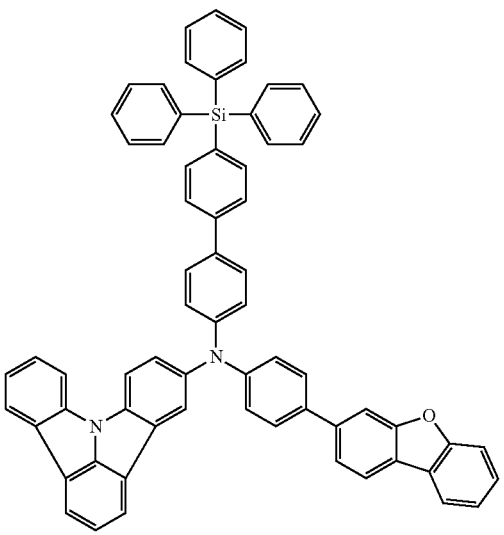
132

-continued
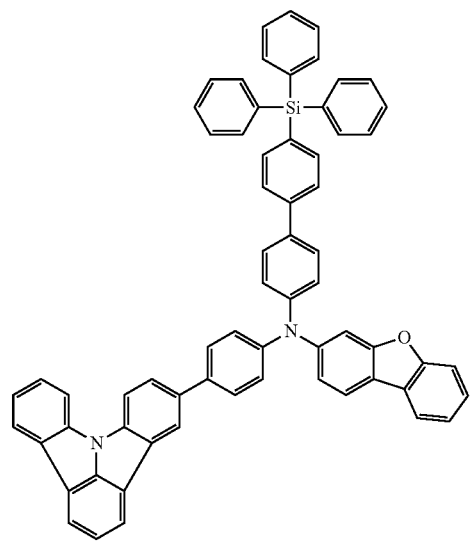
133
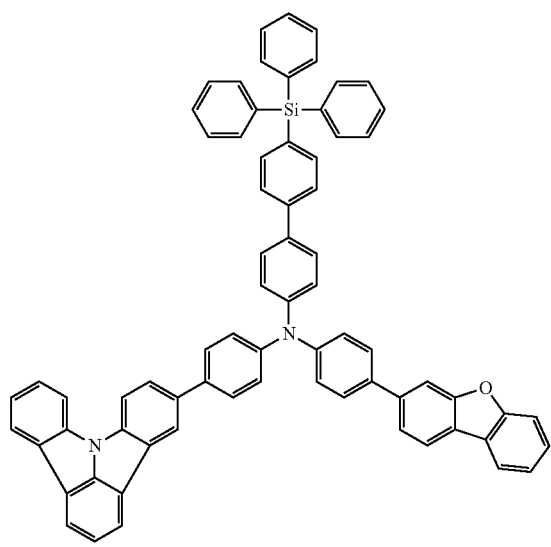
134
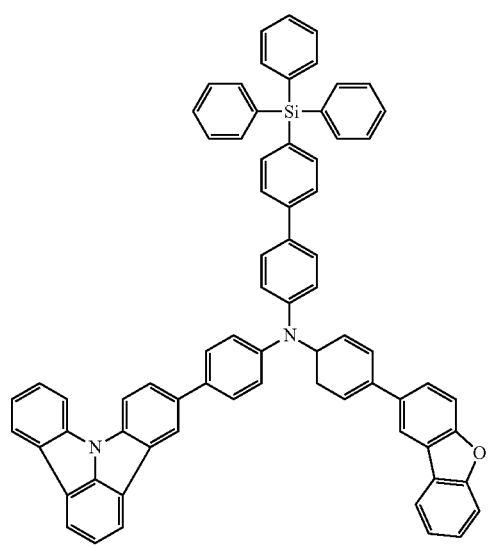
135
-continued
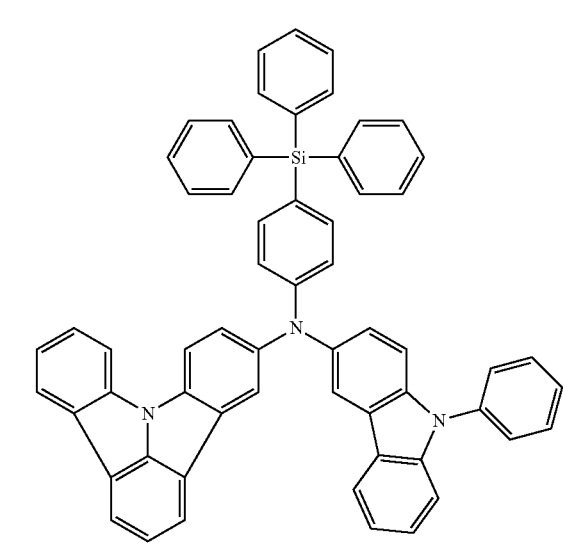
136
[Formula 10]
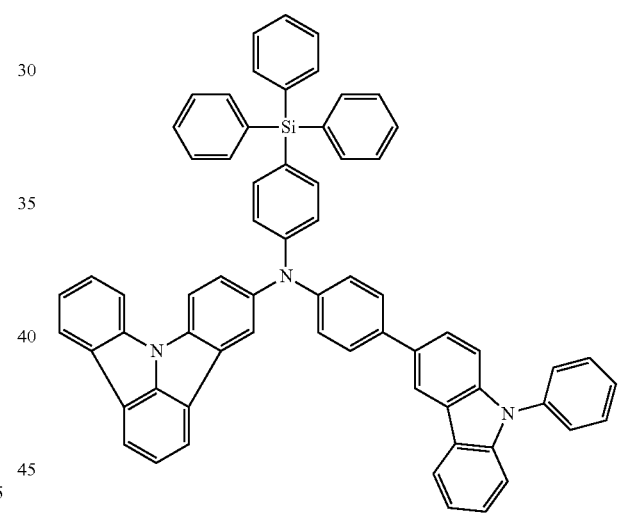
137
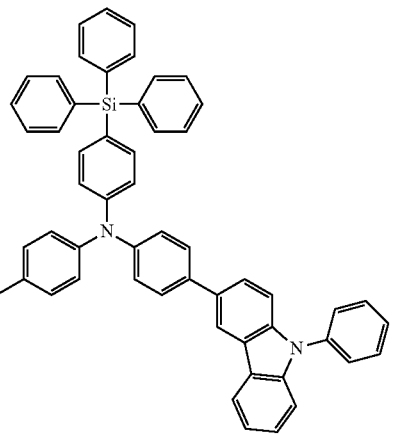
138

139
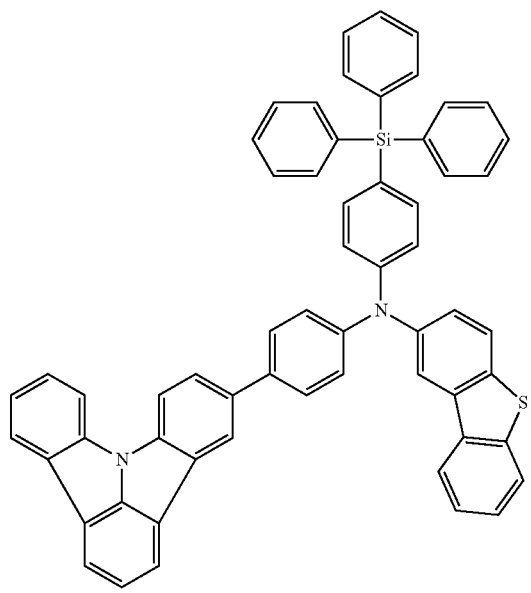
140
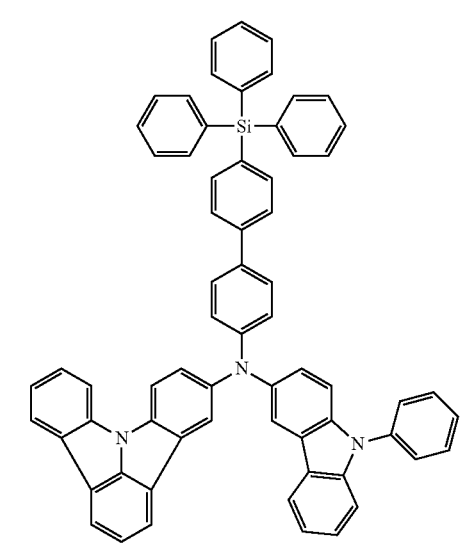
141
142
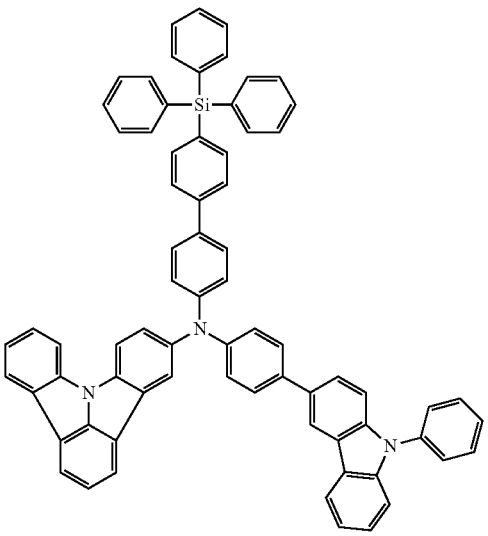
143
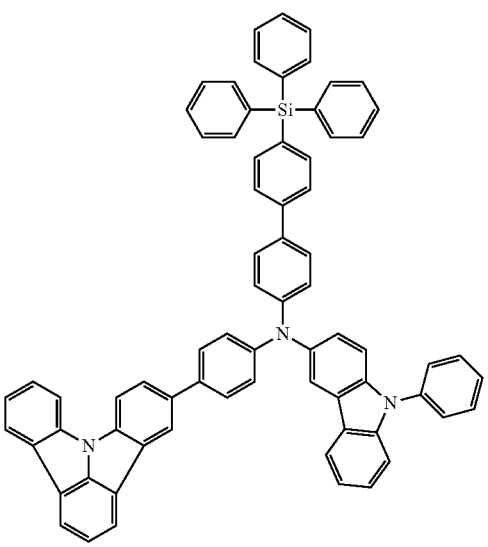
144
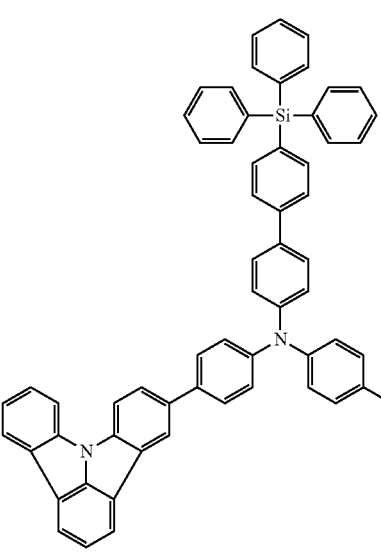

18. The device as claimed in claim 4, wherein the compound represented by Formula 1 includes one or more compounds represented in the following Formula 11 and Formula 12:
[Formula 11]
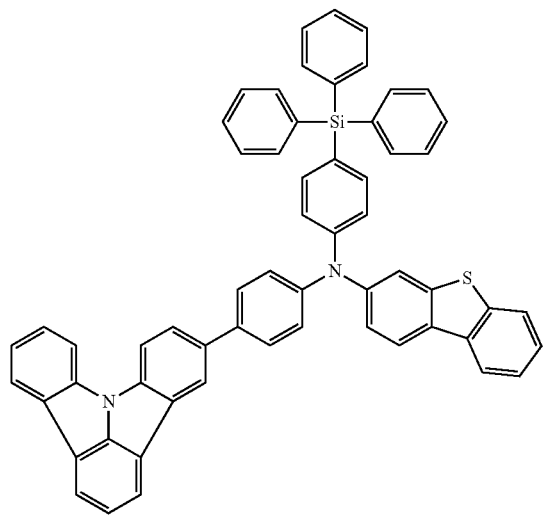
145
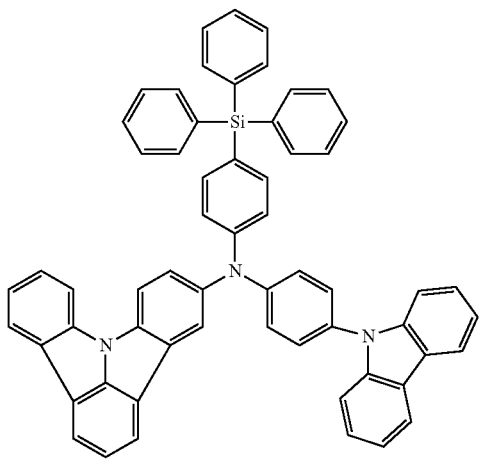
146
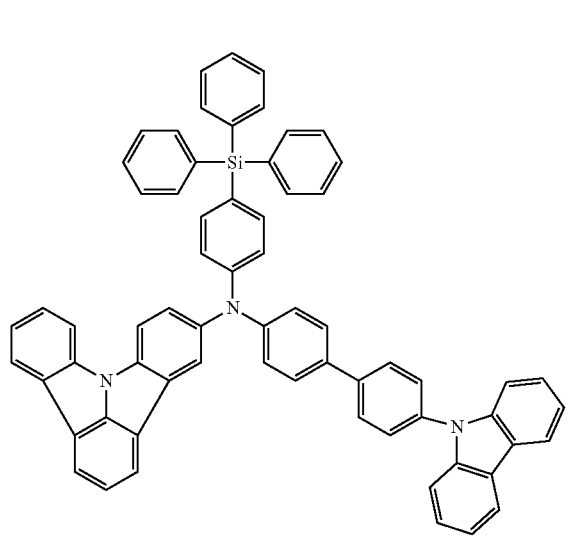
147
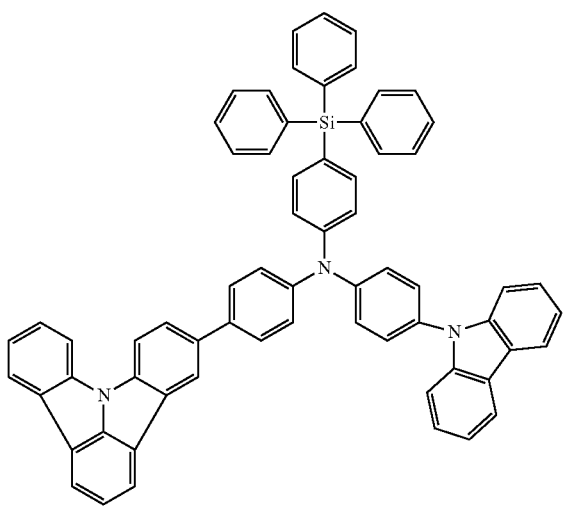
148

149
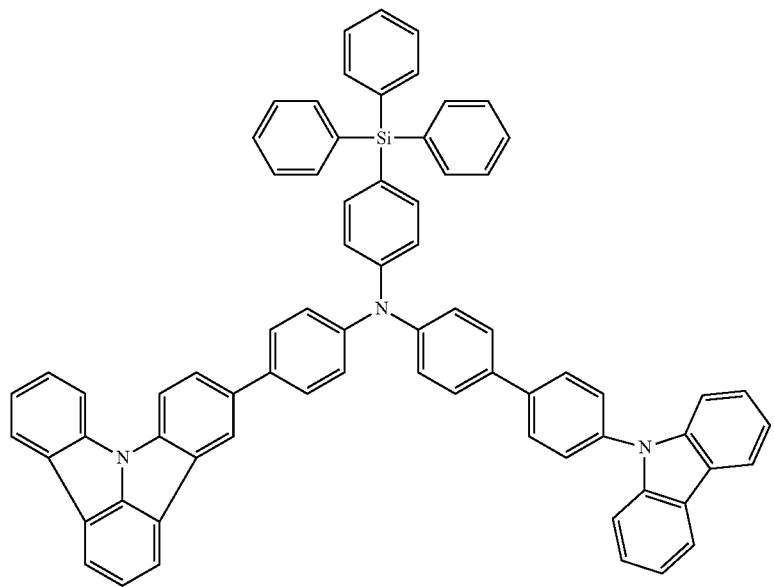
150
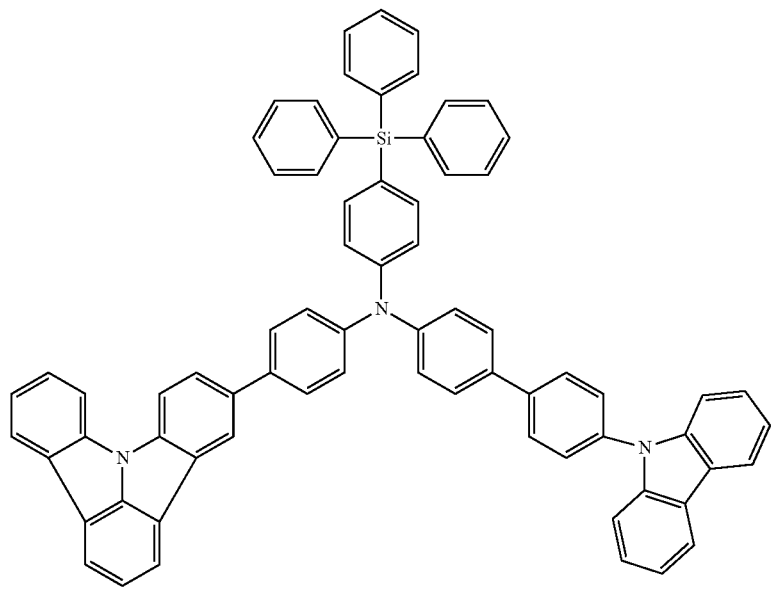

-continued
151 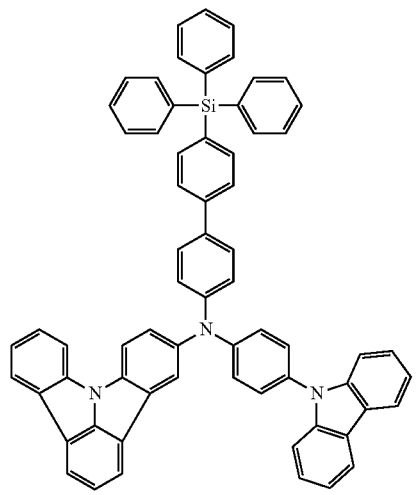
152 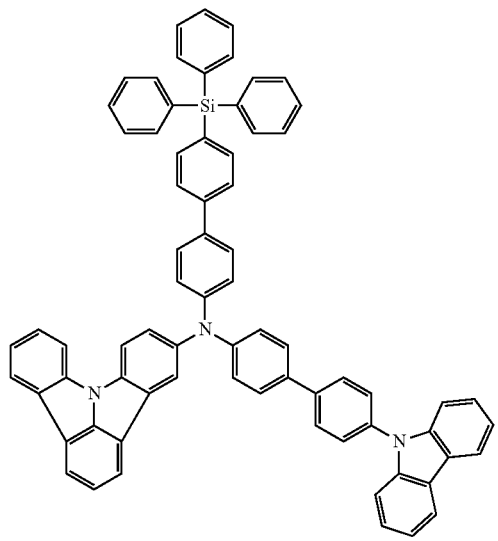
[Formula 12]
153 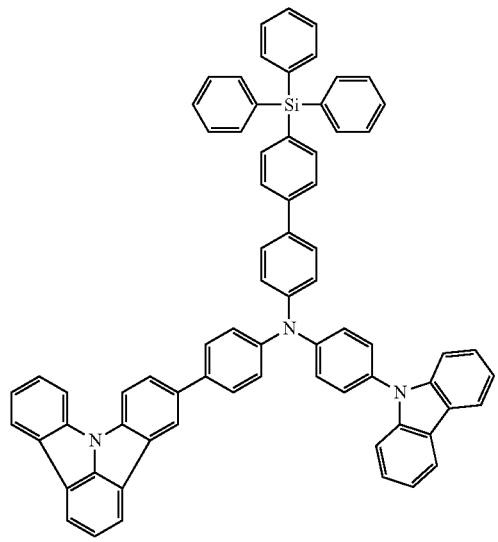
154 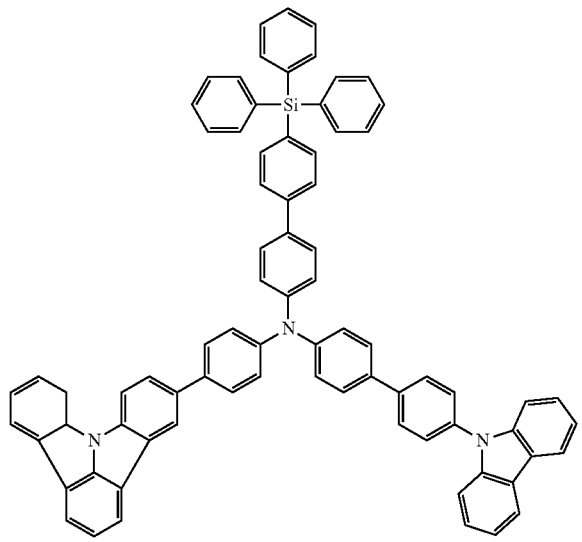

-continued
155
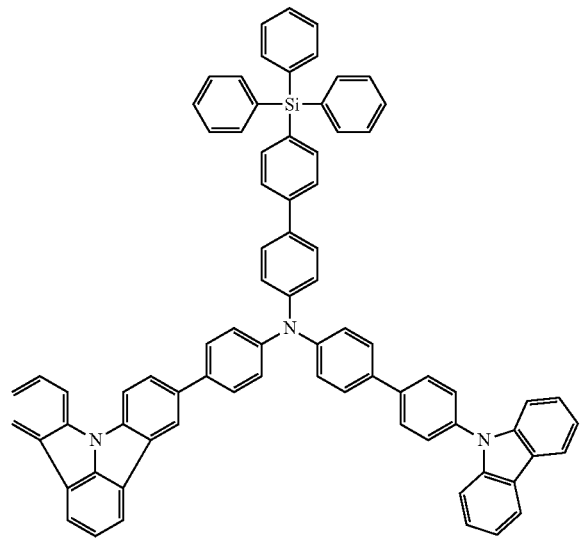
156
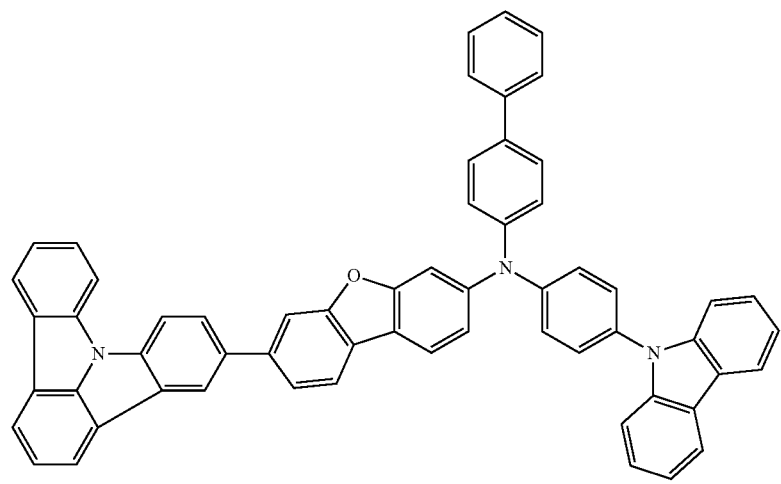
157
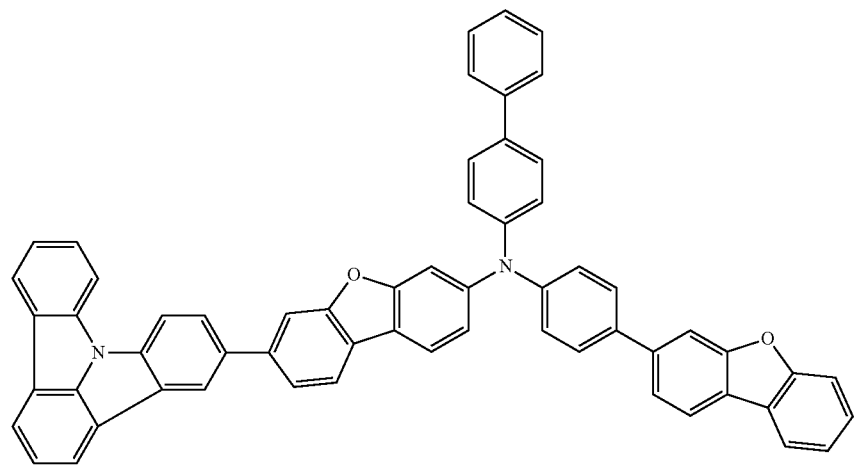

-continued
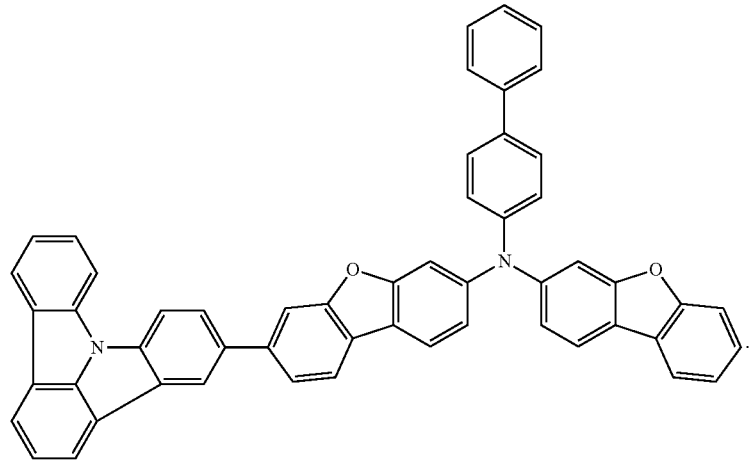
158
19. The device as claimed in claim 4, wherein the compound represented by Formula 1 includes one or more compounds represented in the following Formula 13 and Formula 14:
[Formula 13]
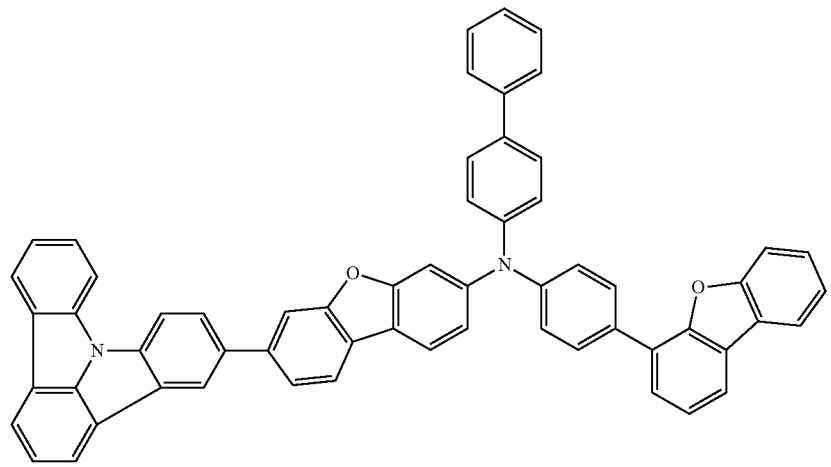
159

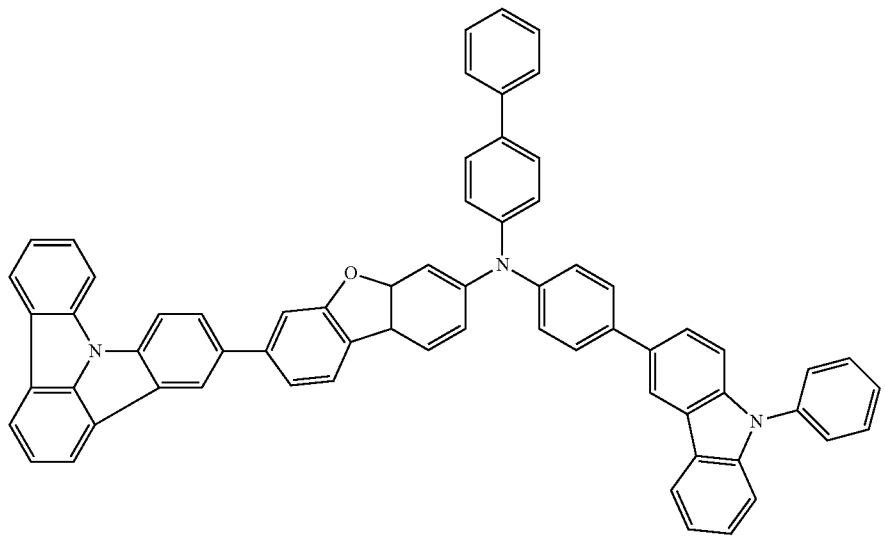
160
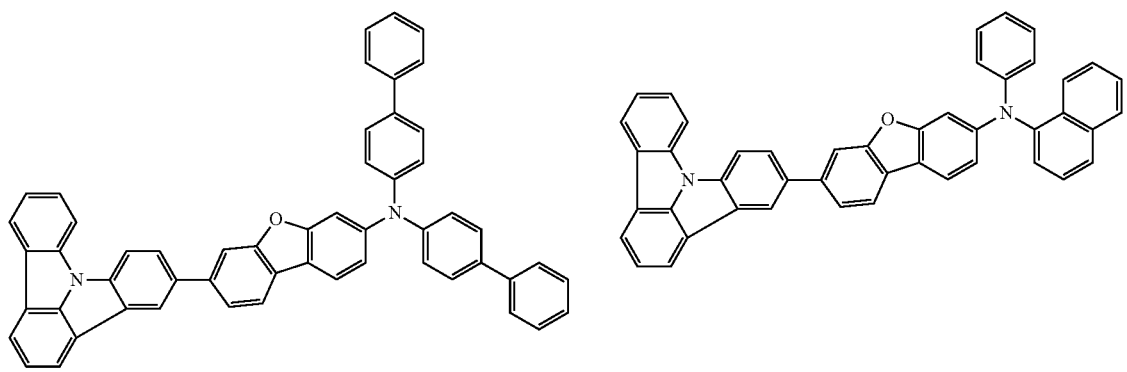
161 162
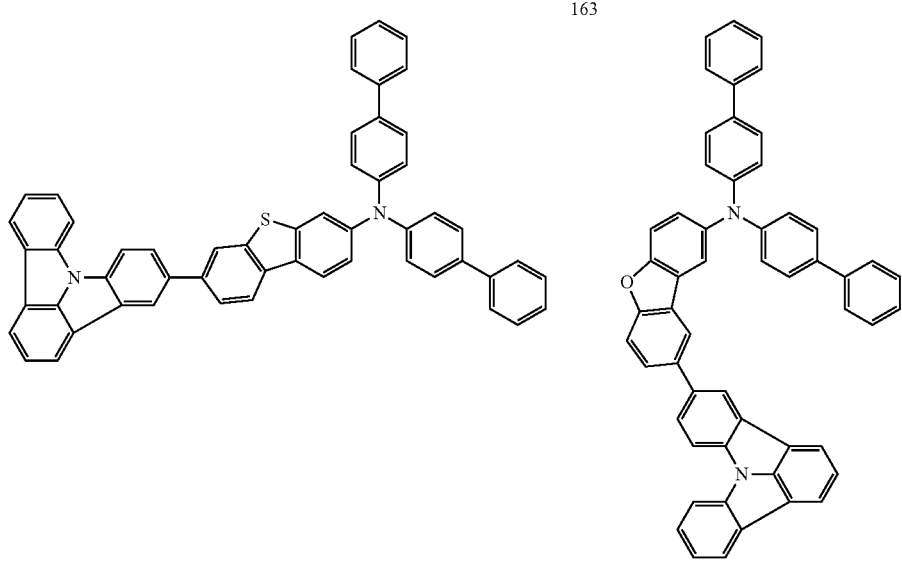
163 164

[Formula 14]
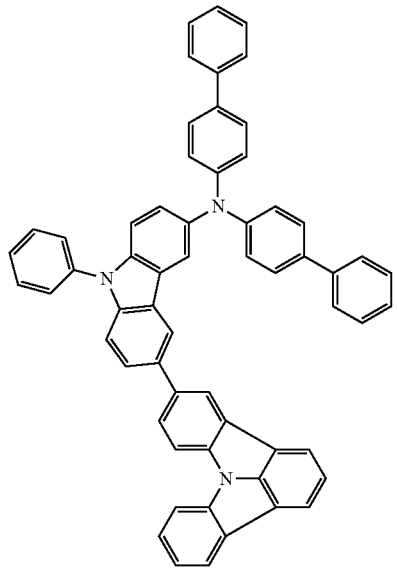
165
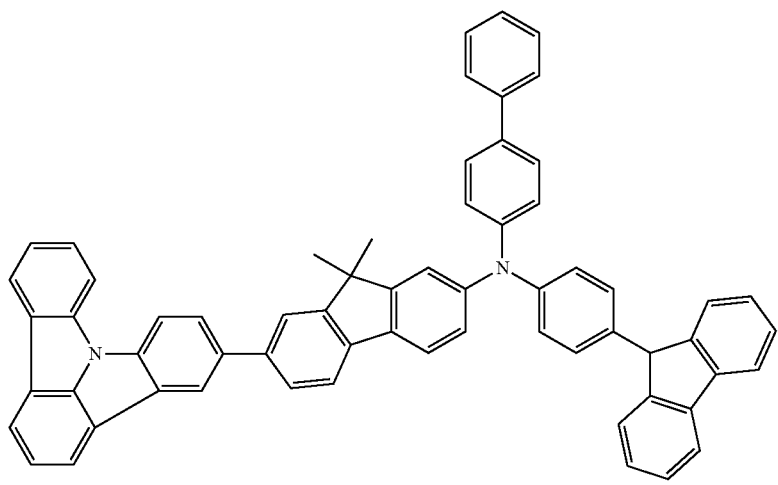
166
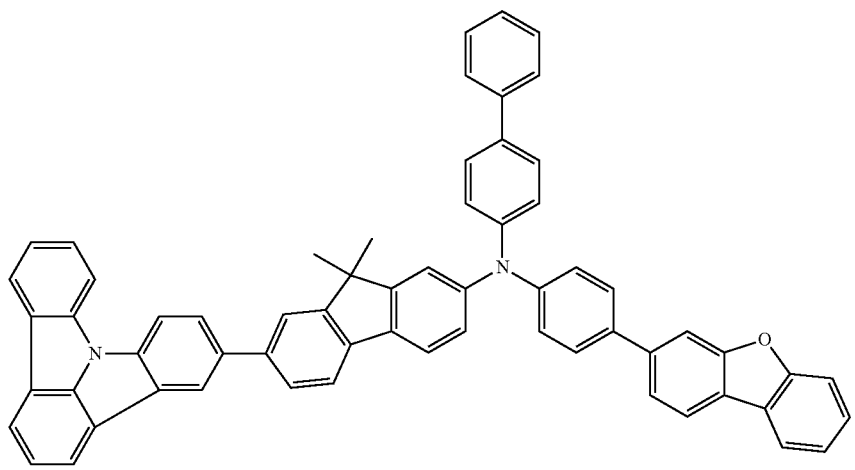
167

-continued
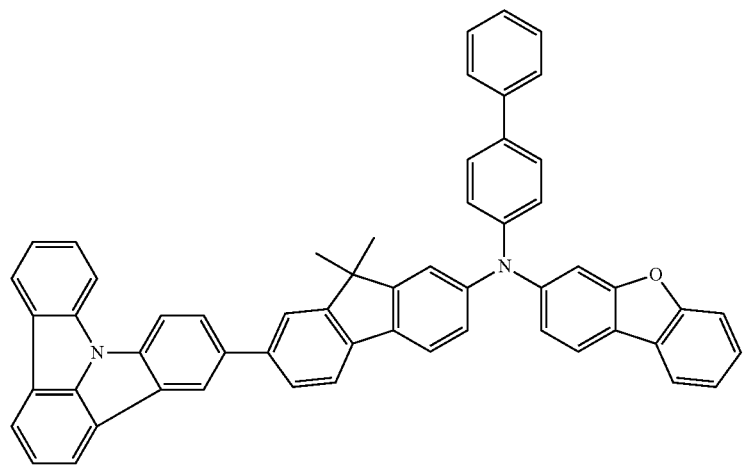
168
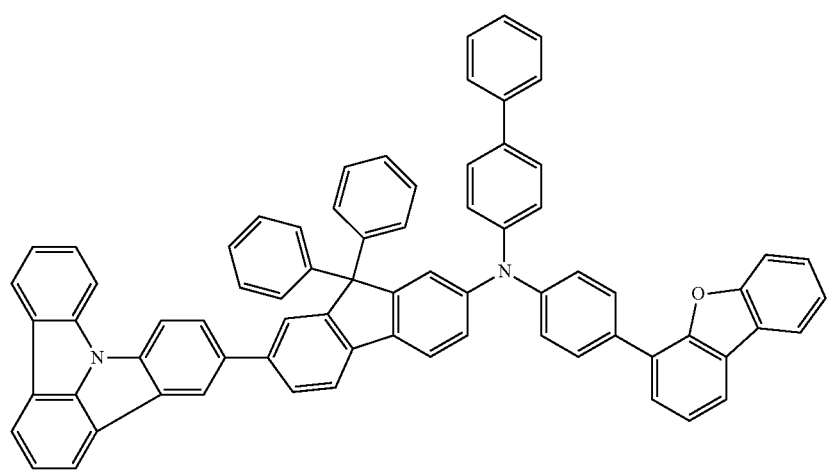
169

-continued
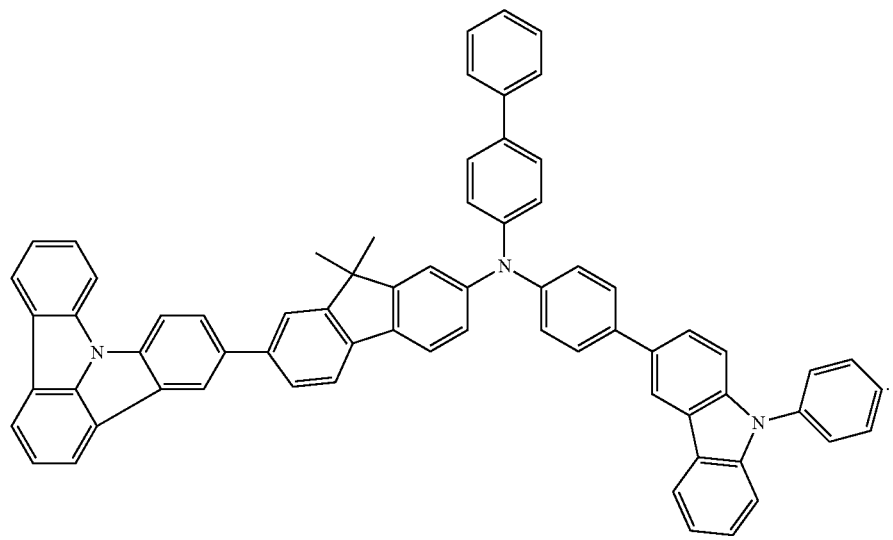
170
* * * * *